(12) United States Patent
Monsonego et al.

(10) Patent No.: US 12,098,202 B2
(45) Date of Patent: Sep. 24, 2024

(54) NON-CYTOTOXIC MODIFIED CELLS AND USE THEREOF

(71) Applicant: THE NATIONAL INSTITUTE FOR BIOTECHNOLOGY IN THE NEGEV LTD., Beer Sheva (IL)

(72) Inventors: Alon Monsonego, Moshav Nir Banim (IL); Angel Porgador, Lehavim (IL); Roee Atlas, Givataim (IL)

(73) Assignee: THE NATIONAL INSTITUTE FOR BIOTECHNOLOGY IN THE NEGEV LTD., Beer Sheva (IL)

( * ) Notice: Subject to any disclaimer, the term of this patent is extended or adjusted under 35 U.S.C. 154(b) by 205 days.

(21) Appl. No.: 16/340,196

(22) PCT Filed: Oct. 10, 2017

(86) PCT No.: PCT/IL2017/051133
§ 371 (c)(1),
(2) Date: Apr. 8, 2019

(87) PCT Pub. No.: WO2018/069927
PCT Pub. Date: Apr. 19, 2018

(65) Prior Publication Data
US 2019/0233516 A1    Aug. 1, 2019

Related U.S. Application Data

(60) Provisional application No. 62/406,005, filed on Oct. 10, 2016.

(51) Int. Cl.
| | |
|---|---|
| C07K 16/28 | (2006.01) |
| A61K 35/15 | (2015.01) |
| A61K 35/17 | (2015.01) |
| A61K 48/00 | (2006.01) |
| A61P 3/00 | (2006.01) |
| A61P 9/00 | (2006.01) |
| A61P 25/28 | (2006.01) |
| A61P 35/00 | (2006.01) |
| C07K 14/705 | (2006.01) |
| C07K 14/725 | (2006.01) |
| C07K 16/18 | (2006.01) |
| C12N 5/0783 | (2010.01) |

(52) U.S. Cl.
CPC .......... *C07K 16/2809* (2013.01); *A61K 35/15* (2013.01); *A61K 35/17* (2013.01); *A61K 48/00* (2013.01); *A61P 3/00* (2018.01); *A61P 9/00* (2018.01); *A61P 25/28* (2018.01); *A61P 35/00* (2018.01); *C07K 14/7051* (2013.01); *C07K 14/70532* (2013.01); *C07K 16/18* (2013.01); *C07K 16/2818* (2013.01); *C12N 5/0636* (2013.01); *C12N 5/0638* (2013.01); *C12N 5/0646* (2013.01); *C07K 2317/74* (2013.01); *C07K 2317/75* (2013.01); *C07K 2319/03* (2013.01); *C07K 2319/41* (2013.01); *C07K 2319/60* (2013.01); *C12N 2501/25* (2013.01); *C12N 2501/335* (2013.01); *C12N 2501/515* (2013.01); *C12N 2502/30* (2013.01); *C12N 2510/00* (2013.01)

(58) Field of Classification Search
CPC ............ C07K 16/2809; C07K 14/7051; C07K 14/70532; C07K 16/18; C07K 16/2818; A61P 25/28; A61P 3/00; A61P 9/00; A61P 35/00; A61K 35/15; A61K 35/17; A61K 48/00; C12N 5/0636; C12N 5/0638; C12N 5/0646
See application file for complete search history.

(56) References Cited

U.S. PATENT DOCUMENTS

| | | |
|---|---|---|
| 5,843,780 A | 12/1998 | Thomson |
| 6,200,806 B1 | 3/2001 | Thomson |
| 7,029,913 B2 | 4/2006 | Thomson |
| 7,034,121 B2 | 4/2006 | Carreno et al. |
| 7,109,003 B2 | 9/2006 | Hanson et al. |
| 7,153,684 B1 | 12/2006 | Hogan |
| 7,427,665 B2 | 9/2008 | Bowdish et al. |
| 7,452,535 B2 | 11/2008 | Davis et al. |
| 7,459,156 B2 | 12/2008 | Clary et al. |

(Continued)

FOREIGN PATENT DOCUMENTS

| | | |
|---|---|---|
| EP | 2844742 A1 | 3/2015 |
| JP | WO2007142241 A1 | 10/2009 |

(Continued)

OTHER PUBLICATIONS

Zhao et al. "A Herceptin-Based Chimeric Antigen Receptor with Modified Signaling Domains Leads to Enhanced Survival of Transduced T Lymphocytes and Antitumor Activity", J Immunol. Nov. 1, 2009; 183(9): 5563-5574. (Year: 2009).*

(Continued)

*Primary Examiner* — Amy E Juedes
*Assistant Examiner* — Peter Johansen
(74) *Attorney, Agent, or Firm* — The Roy Gross Law Firm, LLC; Roy Gross

(57) ABSTRACT

Modified cells comprising a transmembrane polypeptide comprising at least one extracellular target receptor-binding domain, a transmembrane domain and an intracellular domain, wherein the intracellular domain is not capable of transducing any signal are provided. Methods of inducing or inhibiting signaling by a target receptor in a target cell comprising contacting the target cell with a modified cell of the invention are also provided.

19 Claims, 10 Drawing Sheets

Specification includes a Sequence Listing.

(56) References Cited

U.S. PATENT DOCUMENTS

| | | | |
|---|---|---|---|
| 7,488,802 | B2 | 2/2009 | Collins et al. |
| 7,592,007 | B2 | 9/2009 | Gribben et al. |
| 7,595,048 | B2 | 9/2009 | Honjo et al. |
| 7,605,238 | B2 | 10/2009 | Korman et al. |
| 7,722,868 | B2 | 5/2010 | Freeman et al. |
| 7,750,122 | B2 | 7/2010 | Cho et al. |
| 7,943,743 | B2 | 5/2011 | Korman et al. |
| 8,008,449 | B2 | 8/2011 | Korman et al. |
| 8,501,693 | B2 | 8/2013 | Kim et al. |
| 8,617,546 | B2 | 12/2013 | Kang et al. |
| 8,642,035 | B2 | 2/2014 | Luehrsen |
| 9,028,820 | B2 | 5/2015 | Hofbauer et al. |
| 9,181,342 | B2 | 11/2015 | Davis |
| 9,328,154 | B2 | 5/2016 | Chilkoti |
| 9,358,287 | B2 | 6/2016 | Harp et al. |
| 10,273,300 | B2 * | 4/2019 | Bedoya ................ C12N 9/1276 |
| 2009/0047263 | A1 | 2/2009 | Yamanaka et al. |
| 2009/0068742 | A1 | 3/2009 | Yamanaka |
| 2009/0191159 | A1 | 7/2009 | Sakurada et al. |
| 2009/0227032 | A1 | 9/2009 | Yamanaka et al. |
| 2009/0246875 | A1 | 10/2009 | Yamanaka et al. |
| 2009/0304646 | A1 | 12/2009 | Sakurada et al. |
| 2010/0135974 | A1 * | 6/2010 | Eshhar ................ A61K 39/4631 435/375 |
| 2011/0097326 | A1 * | 4/2011 | Luehrsen ........... C07K 16/2863 530/389.1 |
| 2012/0302466 | A1 | 11/2012 | Sentman et al. |
| 2017/0151281 | A1 * | 6/2017 | Wagner ................ C07K 16/30 |

FOREIGN PATENT DOCUMENTS

| | | | | |
|---|---|---|---|---|
| JP | 2015516818 | A | 6/2015 | |
| WO | 9920741 | A1 | 4/1999 | |
| WO | 0151616 | A2 | 7/2001 | |
| WO | 03020920 | A1 | 3/2003 | |
| WO | 2013166051 | A1 | 11/2013 | |
| WO | WO-2015142675 | A2 * | 9/2015 | ......... A61K 38/2086 |
| WO | 2016014565 | A2 | 1/2016 | |
| WO | WO-2017218850 | A1 * | 12/2017 | ............. A61K 35/17 |

OTHER PUBLICATIONS

Baselga et al. "Novel anticancer targets: revisiting ERBB2 and discovering ERBB3", Nat Rev Cancer. Jul. 2009;9(7):463-75 (Year: 2009).*

Roy et al., "Beyond trastuzumab: small molecule tyrosine kinase inhibitors in HER-2-positive breast cancer", Oncologist. Nov. 2009; 14(11):1061-9 (Year: 2009).*

Chen et al. "Autocrine activity of BDNF induced by the STAT3 signaling pathway causes prolonged TrkB activation and promotes human non-small-cell lung cancer proliferation", Sci Rep. Jul. 26, 2016;6:30404. (Year: 2016).*

Jensen et al. "Design and implementation of adoptive therapy with chimeric antigen receptor-modified T cells", Immunol Rev. Jan. 2014; 257(1): 127-144 (Year: 2014).*

Essand et al. "Genetically engineered T cells for the treatment of cancer", J Intern Med. Feb. 2013; 273(2): 166-181 (Year: 2013).*

Kotteas et al. "Immunotherapy for pancreatic cancer", Journal of Cancer Research & Clinical Oncology, 142.8: 1795-1805. (Year: 2016).*

Li-Lian et al. "Molecular Mechanisms and Potential Therapeutic Reversal of Pancreatic Cancer-Induced Immune Evasion", Cancers 12.7: 1872 (Year: 2020).*

MacDonald et al. "Alloantigen-specific regulatory T cells generated with a chimeric antigen receptor", J Clin Invest. Apr. 1, 2016;126(4):1413-24 (Year: 2016).*

Combadière et al. "Qualitative and quantitative contributions of the T cell receptor zeta chain to mature T cell apoptosis", J Exp Med. May 1, 1996;183(5):2109-17. (Year: 1996).*

Velcheti et al. "Basic Overview of Current Immunotherapy Approaches in Cancer", Am Soc Clin Oncol Educ Book. 2016;35:298-308 (Year: 2016).*

Chen at al. "Research on drug resistance mechanism of trastuzumab caused by activation of the PI3K/Akt signaling pathway", Contemp Oncol (Pozn). 2013;17(4):363-9. (Year: 2013).*

Yang et al. "CD4 CAR T Cells Mediate CD8-like Cytotoxic Anti-Leukemic Effects Resulting in Leukemic Clearance and Are Less Susceptible to Attenuation By Endogenous TCR Activation Than CD8 Car T Cells", Blood (2015) 126(23):100 (Year: 2015).*

Hombach et al. "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule", J Immunol. Dec. 1, 2001;167(11):6123-31 (Year: 2001).*

Lanitis et al. "Chimeric antigen receptor T Cells with dissociated signaling domains exhibit focused antitumor activity with reduced potential for toxicity in vivo", Cancer Immunol Res. Jul. 2013;1(1):43-53 (Year: 2013).*

Sunder-Plassmann et al. "Functional analysis of immunoreceptor tyrosine-based activation motif (ITAM)-mediated signal transduction: the two YxxL segments within a single CD3zeta-ITAM are functionally distinct", Eur J Immunol. Aug. 1997;27(8):2001-9 (Year: 1997).*

Han, E. Q. et al., Chimeric antigen receptor-engineered T cells for cancer immunotherapy: progress and challenges. Journal of Hematology & Oncology, 6(1), 47, 2013.

Hwang, S. et al., Reduced TCR signaling potential impairs negative selection but does not result in autoimmune disease. The Journal of Experimental Medicine, 209(10), 1781-1795, 2012.

Zhao, Y. et al., A Herceptin-Based Chimeric Antigen Receptor with Modified Signaling Domains Leads to Enhanced Survival of Transduced T Lymphocytes and Antitumor Activity. The Journal of Immunology, 183(9), 5563-5574, 2009.

Thomson et al., "Embryonic Stem Cell Lines Derived from Human Blastocysts", Science, vol. 282, 1145-1147, 1998.

Thomson et al., "Isolation of a primate embryonic stem cell line", Proc. Natl. Acad. Sci. vol. 92, pp. 7844-7848, 1995.

Thomson et al., "Pluripotent Cell Lines Derived from Common Marmoset (Callithrix jacchus) Blastocysts" Biology of Reproduction, vol. 55, pp. 254-259, 1996.

Shamblott et al., "Derivation of pluripotent stem cells from cultured human primordial germ cells", Proc. Natl. Acad. Sci. vol. 95, pp. 13726-13731, 1998.

Matsui, Y., et al., "Derivation of pluripotential embryonic stem cells from murine primordial germ cells in culture." Cell. Sep. 4, 1992;70(5):841-7.

Shamblott et al., "Human embryonic germ cell derivatives express a broad range of developmentally distinct markers and proliferate extensively in vitro." Proc. Natl. Acad. Sci. USA vol. 98, No. 1, 113-118, 2001.

Koshimizu et al., "Functional requirement of gp130-mediated signaling for growth and survival of mouse primordial germ cells in vitro and derivation of embryonic germ (EG) cells", Development 122, 1235-1242 (1996).

Daniel Abate-Daga et al., "CAR models: next-generation CAR modifications for enhanced T-cell function", Molecular Therapy—Oncolytics (2016) 3, 16014.

International Search Report PCT/IL2017/051133 Completed Jan. 16, 2018; Mailed Jan. 18, 2018 4 pages.

Written Opinion of the International Searching Authority PCT/IL2017/051133 Mailed Jan. 18, 2018 6 pages.

* cited by examiner

SEQUENCE LISTING

```
<160> NUMBER OF SEQ ID NOS: 34

<210> SEQ ID NO 1
<211> LENGTH: 22
<212> TYPE: PRT
<213> ORGANISM: Homo sapiens

<400> SEQUENCE: 1

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 2
<211> LENGTH: 23
<212> TYPE: PRT
<213> ORGANISM: Artificial
<220> FEATURE:
<223> OTHER INFORMATION: Synthetic

<400> SEQUENCE: 2

Met Asp Met Arg Val Pro Ala Gln Leu Leu Gly Leu Leu Leu Leu Trp
1               5                   10                  15

Leu Ser Gly Ala Arg Cys Gln
            20

<210> SEQ ID NO 3
<211> LENGTH: 27
<212> TYPE: PRT
<213> ORGANISM: Homo sapiens

<400> SEQUENCE: 3

Met Ala Thr Gly Ser Arg Thr Ser Leu Leu Leu Ala Phe Gly Leu Leu
1               5                   10                  15

Cys Leu Pro Trp Leu Gln Glu Gly Ser Gln Ala
            20                  25

<210> SEQ ID NO 4
<211> LENGTH: 18
<212> TYPE: PRT
<213> ORGANISM: Artificial
<220> FEATURE:
<223> OTHER INFORMATION: Synthetic

<400> SEQUENCE: 4

Gly Gly Ser Ser Arg Ser Ser Ser Gly Gly Gly Gly Ser Gly Gly
1               5                   10                  15

Gly Gly

<210> SEQ ID NO 5
<211> LENGTH: 20
<212> TYPE: PRT
<213> ORGANISM: Artificial
<220> FEATURE:
```

<223> OTHER INFORMATION: Synthetic

<400> SEQUENCE: 5

Gly Gly Gly Gly Ser Gly Gly Gly Ser Gly Gly Gly Ser Gly
1               5                   10                  15

Gly Gly Gly Ser
            20

<210> SEQ ID NO 6
<211> LENGTH: 10
<212> TYPE: PRT
<213> ORGANISM: Artificial
<220> FEATURE:
<223> OTHER INFORMATION: Synthetic

<400> SEQUENCE: 6

Glu Gln Lys Leu Ile Ser Glu Glu Asp Leu
1               5                   10

<210> SEQ ID NO 7
<211> LENGTH: 62
<212> TYPE: PRT
<213> ORGANISM: Homo sapiens

<400> SEQUENCE: 7

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Ser
        35                  40                  45

Arg Pro Ala Ala Gly Gly Ala Val His Thr Arg Gly Leu Asp
    50                  55                  60

<210> SEQ ID NO 8
<211> LENGTH: 134
<212> TYPE: PRT
<213> ORGANISM: Mus musculus

<400> SEQUENCE: 8

Leu Cys Tyr Leu Leu Asp Gly Ile Leu Phe Ile Tyr Gly Val Ile Ile
1               5                   10                  15

Thr Ala Leu Tyr Leu Arg Ala Lys Phe Ser Arg Ser Ala Glu Thr Ala
            20                  25                  30

Ala Asn Leu Gln Asp Pro Asn Gln Leu Tyr Asn Glu Leu Asn Leu Gly
        35                  40                  45

Arg Arg Glu Glu Tyr Asp Val Leu Glu Lys Lys Arg Ala Arg Asp Pro
    50                  55                  60

Glu Met Gly Gly Lys Gln Gln Arg Arg Arg Asn Pro Gln Glu Gly Val
65              70                  75                  80

Tyr Asn Ala Leu Gln Lys Asp Lys Met Ala Glu Ala Tyr Ser Glu Ile
                85                  90                  95

Gly Thr Lys Gly Glu Arg Arg Arg Gly Lys Gly His Asp Gly Leu Tyr
            100                 105                 110

Gln Gly Leu Ser Thr Ala Thr Lys Asp Thr Tyr Asp Ala Leu His Met
        115                 120                 125

Gln Thr Leu Ala Pro Arg
    130

<210> SEQ ID NO 9
<211> LENGTH: 134
<212> TYPE: PRT
<213> ORGANISM: Artificial
<220> FEATURE:
<223> OTHER INFORMATION: Synthetic

<400> SEQUENCE: 9

```
Leu Cys Tyr Leu Leu Asp Gly Ile Leu Phe Ile Tyr Gly Val Ile Ile
1               5                   10                  15

Thr Ala Leu Tyr Leu Arg Ala Lys Phe Ser Arg Ser Ala Glu Thr Ala
            20                  25                  30

Ala Asn Leu Gln Asp Pro Asn Gln Leu Phe Asn Glu Leu Asn Leu Gly
        35                  40                  45

Arg Arg Glu Glu Phe Asp Val Leu Glu Lys Lys Arg Ala Arg Asp Pro
    50                  55                  60

Glu Met Gly Gly Lys Gln Gln Arg Arg Arg Asn Pro Gln Glu Gly Val
65                  70                  75                  80

Phe Asn Ala Leu Gln Lys Asp Lys Met Ala Glu Ala Phe Ser Glu Ile
                85                  90                  95

Gly Thr Lys Gly Glu Arg Arg Arg Gly Lys Gly His Asp Gly Leu Phe
            100                 105                 110

Gln Gly Leu Ser Thr Ala Thr Lys Asp Thr Phe Asp Ala Leu His Met
        115                 120                 125

Gln Thr Leu Ala Pro Arg
    130
```

<210> SEQ ID NO 10
<211> LENGTH: 114
<212> TYPE: PRT
<213> ORGANISM: Homo sapiens

<400> SEQUENCE: 10

```
Asp Val Val Met Thr Gln Leu Pro Leu Ser Leu Pro Val Ile Leu Gly
1               5                   10                  15

Asp Gln Ala Ser Ile Ser Cys Arg Ser Ser Gln Ser Leu Ile His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

Arg Ala
```

<210> SEQ ID NO 11
<211> LENGTH: 119
<212> TYPE: PRT
<213> ORGANISM: Homo sapiens

<400> SEQUENCE: 11

```
Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Ser Tyr
```

```
                    20                  25                  30

Asp Ile Asn Trp Val Lys Gln Arg Pro Gly Gln Gly Leu Glu Trp Ile
                35                  40                  45

Gly Trp Ile Tyr Pro Arg Asp Gly Ser Ile Lys Phe Asn Glu Lys Phe
            50                  55                  60

Lys Gly Lys Ala Thr Leu Thr Val Asp Thr Ser Ser Thr Ala Tyr
65                  70                  75                  80

Met Glu Leu His Ser Leu Thr Ser Glu Asp Ser Ala Ala Tyr Phe Cys
                85                  90                  95

Ala Arg Arg Gly Arg Leu Leu Leu Tyr Gly Phe Ala Tyr Trp Gly Gln
                100                 105                 110

Gly Thr Leu Val Thr Val Ser
            115

<210> SEQ ID NO 12
<211> LENGTH: 114
<212> TYPE: PRT
<213> ORGANISM: Homo sapiens

<400> SEQUENCE: 12

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Asn Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Tyr Thr Phe Gly Gly Gly Thr Lys Leu Glu Ile Lys
                100                 105                 110

Arg Ala

<210> SEQ ID NO 13
<211> LENGTH: 117
<212> TYPE: PRT
<213> ORGANISM: Homo sapiens

<400> SEQUENCE: 13

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
                20                  25                  30

Glu Met His Trp Val Lys Gln Thr Pro Val His Gly Leu Glu Trp Ile
                35                  40                  45

Gly Thr Ile Asp Pro Glu Thr Ala Gly Thr Ala Tyr Asn Asn Gln Lys
            50                  55                  60

Phe Lys Gly Lys Ala Ile Leu Thr Ala Gly Lys Ser Ser Ser Thr Ala
65                  70                  75                  80

Tyr Met Glu Leu Arg Ser Leu Thr Ser Glu Asp Ser Ala Val Tyr Tyr
                85                  90                  95

Cys Thr Gly Val Thr Thr Trp Phe Ala Tyr Trp Gly Gln Gly Thr Leu
                100                 105                 110
```

Val Thr Val Ser Ala
        115

<210> SEQ ID NO 14
<211> LENGTH: 108
<212> TYPE: PRT
<213> ORGANISM: Homo sapiens

<400> SEQUENCE: 14

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Val Thr Tyr Met
            20                  25                  30

His Trp Tyr Gln Gln Arg Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Gly Asn Asn Pro Gln Tyr
                85                  90                  95

Thr Phe Gly Gly Gly Thr Arg Leu Glu Ile Lys Arg
            100                 105

<210> SEQ ID NO 15
<211> LENGTH: 120
<212> TYPE: PRT
<213> ORGANISM: Homo sapiens

<400> SEQUENCE: 15

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Thr Gly Val Gly Trp Ile Arg Gln Pro Ser Gly Lys Gly Leu Glu
        35                  40                  45

Trp Leu Ser His Ile Trp Trp Asp Val Lys Arg Tyr Asn Pro Ala
    50                  55                  60

Leu Lys Ser Arg Leu Thr Ile Ser Arg Asp Thr Ser Tyr Ser Gln Val
65                  70                  75                  80

Phe Leu Arg Ile Ala Ser Val Asp Thr Ala Asp Thr Ala Thr Tyr Tyr
                85                  90                  95

Cys Ala Arg Ile Leu Asp Gly Thr Gly Pro Met Asp Tyr Trp Gly Gln
            100                 105                 110

Gly Thr Ser Val Thr Val Ser Ser
        115                 120

<210> SEQ ID NO 16
<211> LENGTH: 217
<212> TYPE: PRT
<213> ORGANISM: Homo sapiens

<400> SEQUENCE: 16

Glu Gly Ser Ala Asp Tyr Lys Asp His Asp Gly Asp Tyr Lys Asp His
1               5                   10                  15

Asp Ile Asp Tyr Lys Asp Asp Asp Lys Phe Pro Thr Ile Pro Leu
            20                  25                  30

```
Ser Arg Leu Phe Asp Asn Ala Met Leu Arg Ala His Arg Leu His Gln
        35                  40                  45

Leu Ala Phe Asp Thr Tyr Gln Glu Phe Glu Ala Tyr Ile Pro Lys
 50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
        210                 215

<210> SEQ ID NO 17
<211> LENGTH: 460
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (253)..(254)
<223> OTHER INFORMATION: Xaa can be any naturally occurring amino acid

<400> SEQUENCE: 17

Asp Val Val Met Thr Gln Leu Pro Leu Ser Leu Pro Val Ile Leu Gly
 1               5                  10                  15

Asp Gln Ala Ser Ile Ser Cys Arg Ser Ser Gln Ser Leu Ile His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
            100                 105                 110

Arg Ala Gly Gly Ser Ser Arg Ser Ser Ser Gly Gly Gly Ser
        115                 120                 125

Gly Gly Gly Gly Gln Val Gln Leu Gln Gln Ser Gly Pro Glu Leu Val
        130                 135                 140

Lys Pro Gly Ala Ser Val Lys Leu Ser Cys Lys Ala Ser Gly Tyr Thr
145                 150                 155                 160
```

```
Phe Thr Ser Tyr Asp Ile Asn Trp Val Lys Gln Arg Pro Gln Gly
            165                 170                 175

Leu Glu Trp Ile Gly Trp Ile Tyr Pro Arg Asp Gly Ser Ile Lys Phe
        180                 185                 190

Asn Glu Lys Phe Lys Gly Lys Ala Thr Leu Thr Val Asp Thr Ser Ser
        195                 200                 205

Ser Thr Ala Tyr Met Glu Leu His Ser Leu Thr Ser Glu Asp Ser Ala
    210                 215                 220

Ala Tyr Phe Cys Ala Arg Arg Gly Arg Leu Leu Leu Tyr Gly Phe Ala
225                 230                 235                 240

Tyr Trp Gly Gln Gly Thr Leu Val Thr Val Ser Ala Xaa Xaa Glu Gln
                245                 250                 255

Lys Leu Ile Ser Glu Glu Asp Leu Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
        290                 295                 300

Leu Ser Leu Arg Pro Glu Ala Ser Arg Pro Ala Ala Gly Gly Ala Val
305                 310                 315                 320

His Thr Arg Gly Leu Asp Leu Cys Tyr Leu Leu Asp Gly Ile Leu Phe
                325                 330                 335

Ile Tyr Gly Val Ile Ile Thr Ala Leu Tyr Leu Arg Ala Lys Phe Ser
            340                 345                 350

Arg Ser Ala Glu Thr Ala Ala Asn Leu Gln Asp Pro Asn Gln Leu Tyr
        355                 360                 365

Asn Glu Leu Asn Leu Gly Arg Arg Glu Glu Tyr Asp Val Leu Glu Lys
    370                 375                 380

Lys Arg Ala Arg Asp Pro Glu Met Gly Gly Lys Gln Arg Arg Arg
385                 390                 395                 400

Asn Pro Gln Glu Gly Val Tyr Asn Ala Leu Gln Lys Asp Lys Met Ala
                405                 410                 415

Glu Ala Tyr Ser Glu Ile Gly Thr Lys Gly Glu Arg Arg Arg Gly Lys
            420                 425                 430

Gly His Asp Gly Leu Tyr Gln Gly Leu Ser Thr Ala Thr Lys Asp Thr
        435                 440                 445

Tyr Asp Ala Leu His Met Gln Thr Leu Ala Pro Arg
    450                 455                 460

<210> SEQ ID NO 18
<211> LENGTH: 460
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (253)..(254)
<223> OTHER INFORMATION: Xaa can be any naturally occurring amino acid

<400> SEQUENCE: 18

Asp Val Val Met Thr Gln Leu Pro Leu Ser Leu Pro Val Ile Leu Gly
1               5                   10                  15

Asp Gln Ala Ser Ile Ser Cys Arg Ser Ser Gln Ser Leu Ile His Ser
            20                  25                  30

Asn Gly Asn Thr Tyr Leu His Trp Tyr Leu Gln Lys Pro Gly Gln Ser
```

```
                35                  40                  45
Pro Lys Leu Leu Ile Tyr Lys Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Phe Cys Ser Gln Ser
                 85                  90                  95
Thr His Val Pro Phe Thr Phe Gly Ser Gly Thr Lys Leu Glu Ile Lys
                100                 105                 110
Arg Ala Gly Gly Ser Ser Arg Ser Ser Ser Gly Gly Gly Gly Ser
            115                 120                 125
Gly Gly Gly Gly Gln Val Gln Leu Gln Gln Ser Gly Pro Glu Leu Val
130                 135                 140
Lys Pro Gly Ala Ser Val Lys Leu Ser Cys Lys Ala Ser Gly Tyr Thr
145                 150                 155                 160
Phe Thr Ser Tyr Asp Ile Asn Trp Val Lys Gln Arg Pro Gly Gln Gly
                165                 170                 175
Leu Glu Trp Ile Gly Trp Ile Tyr Pro Arg Asp Gly Ser Ile Lys Phe
            180                 185                 190
Asn Glu Lys Phe Lys Gly Lys Ala Thr Leu Thr Val Asp Thr Ser Ser
            195                 200                 205
Ser Thr Ala Tyr Met Glu Leu His Ser Leu Thr Ser Glu Asp Ser Ala
210                 215                 220
Ala Tyr Phe Cys Ala Arg Arg Gly Arg Leu Leu Leu Tyr Gly Phe Ala
225                 230                 235                 240
Tyr Trp Gly Gln Gly Thr Leu Val Thr Val Ser Ala Xaa Xaa Glu Gln
                245                 250                 255
Lys Leu Ile Ser Glu Glu Asp Leu Ala Leu Ser Asn Ser Ile Met Tyr
            260                 265                 270
Phe Ser His Phe Val Pro Val Phe Leu Pro Ala Lys Pro Thr Thr Thr
            275                 280                 285
Pro Ala Pro Arg Pro Pro Thr Pro Ala Pro Thr Ile Ala Ser Gln Pro
290                 295                 300
Leu Ser Leu Arg Pro Glu Ala Ser Arg Pro Ala Ala Gly Gly Ala Val
305                 310                 315                 320
His Thr Arg Gly Leu Asp Leu Cys Tyr Leu Leu Asp Gly Ile Leu Phe
                325                 330                 335
Ile Tyr Gly Val Ile Ile Thr Ala Leu Tyr Leu Arg Ala Lys Phe Ser
            340                 345                 350
Arg Ser Ala Glu Thr Ala Ala Asn Leu Gln Asp Pro Asn Gln Leu Phe
            355                 360                 365
Asn Glu Leu Asn Leu Gly Arg Arg Glu Glu Phe Asp Val Leu Glu Lys
            370                 375                 380
Lys Arg Ala Arg Asp Pro Glu Met Gly Gly Lys Gln Gln Arg Arg Arg
385                 390                 395                 400
Asn Pro Gln Glu Gly Val Phe Asn Ala Leu Gln Lys Asp Lys Met Ala
                405                 410                 415
Glu Ala Phe Ser Glu Ile Gly Thr Lys Gly Arg Arg Arg Gly Lys
            420                 425                 430
Gly His Asp Gly Leu Phe Gln Gly Leu Ser Thr Ala Thr Lys Asp Thr
            435                 440                 445
Phe Asp Ala Leu His Met Gln Thr Leu Ala Pro Arg
450                 455                 460
```

<210> SEQ ID NO 19
<211> LENGTH: 704
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (250)..(251)
<223> OTHER INFORMATION: Xaa can be any naturally occurring amino acid

<400> SEQUENCE: 19

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Tyr Thr Phe Gly Gly Gly Thr Lys Leu Glu Ile Lys
            100                 105                 110

Arg Ala Gly Gly Ser Ser Arg Ser Ser Ser Gly Gly Gly Gly Ser
        115                 120                 125

Gly Gly Gly Gly Gln Val Gln Leu Gln Gln Ser Gly Ala Glu Leu Val
130                 135                 140

Arg Pro Gly Ala Ser Val Thr Leu Ser Cys Lys Ala Ser Gly Tyr Thr
145                 150                 155                 160

Phe Thr Asp Tyr Glu Met His Trp Val Lys Gln Thr Pro Val His Gly
                165                 170                 175

Leu Glu Trp Ile Gly Thr Ile Asp Pro Glu Thr Ala Gly Thr Ala Tyr
            180                 185                 190

Asn Asn Gln Lys Phe Lys Gly Lys Ala Ile Leu Thr Ala Gly Lys Ser
        195                 200                 205

Ser Ser Thr Ala Tyr Met Glu Leu Arg Ser Leu Thr Ser Glu Asp Ser
    210                 215                 220

Ala Val Tyr Tyr Cys Thr Gly Val Thr Thr Trp Phe Ala Tyr Trp Gly
225                 230                 235                 240

Gln Gly Thr Leu Val Thr Val Ser Ala Xaa Xaa Ala Leu Ser Asn Ser
                245                 250                 255

Ile Met Tyr Phe Ser His Phe Val Pro Val Phe Leu Pro Ala Lys Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Ser Arg Pro Ala Ala Gly
    290                 295                 300

Gly Ala Val His Thr Arg Gly Leu Asp Leu Cys Tyr Leu Leu Asp Gly
305                 310                 315                 320

Ile Leu Phe Ile Tyr Gly Val Ile Ile Thr Ala Leu Tyr Leu Arg Ala
                325                 330                 335

Lys Phe Ser Arg Ser Ala Glu Thr Ala Ala Asn Leu Gln Asp Pro Asn 340                 345                 350
Gln Leu Tyr Asn Glu Leu Asn Leu Gly Arg Glu Glu Tyr Asp Val
            355                 360                 365

Leu Glu Lys Lys Arg Ala Arg Asp Pro Glu Met Gly Gly Lys Gln Gln
370                 375                 380

Arg Arg Arg Asn Pro Gln Glu Gly Val Tyr Asn Ala Leu Gln Lys Asp
385                 390                 395                 400

Lys Met Ala Glu Ala Tyr Ser Glu Ile Gly Thr Lys Gly Glu Arg Arg
                405                 410                 415

Arg Gly Lys Gly His Asp Gly Leu Tyr Gln Gly Leu Ser Thr Ala Thr
            420                 425                 430

Lys Asp Thr Tyr Asp Ala Leu His Met Gln Thr Leu Ala Pro Arg Glu
        435                 440                 445

Gly Arg Gly Ser Leu Leu Thr Cys Gly Asp Val Glu Glu Asn Pro Gly
    450                 455                 460

Pro Met Val Ser Lys Gly Glu Glu Leu Phe Thr Gly Val Val Pro Ile
465                 470                 475                 480

Leu Val Glu Leu Asp Gly Asp Val Asn Gly His Lys Phe Ser Val Ser
                485                 490                 495

Gly Glu Gly Glu Gly Asp Ala Thr Tyr Gly Lys Leu Thr Leu Lys Phe
            500                 505                 510

Ile Cys Thr Thr Gly Lys Leu Pro Val Pro Trp Pro Thr Leu Val Thr
        515                 520                 525

Thr Leu Thr Tyr Gly Val Gln Cys Phe Ser Arg Tyr Pro Asp His Met
    530                 535                 540

Lys Gln His Asp Phe Phe Lys Ser Ala Met Pro Glu Gly Tyr Val Gln
545                 550                 555                 560

Glu Arg Thr Ile Phe Phe Lys Asp Asp Gly Asn Tyr Lys Thr Arg Ala
                565                 570                 575

Glu Val Lys Phe Glu Gly Asp Thr Leu Val Asn Arg Ile Glu Leu Lys
            580                 585                 590

Gly Ile Asp Phe Lys Glu Asp Gly Asn Ile Leu Gly His Lys Leu Glu
        595                 600                 605

Tyr Asn Tyr Asn Ser His Asn Val Tyr Ile Met Ala Asp Lys Gln Lys
    610                 615                 620

Asn Gly Ile Lys Val Asn Phe Lys Ile Arg His Asn Ile Glu Asp Gly
625                 630                 635                 640

Ser Val Gln Leu Ala Asp His Tyr Gln Gln Asn Thr Pro Ile Gly Asp
                645                 650                 655

Gly Pro Val Leu Leu Pro Asp Asn His Tyr Leu Ser Thr Gln Ser Ala
            660                 665                 670

Leu Ser Lys Asp Pro Asn Glu Lys Arg Asp His Met Val Leu Leu Glu
        675                 680                 685

Phe Val Thr Ala Ala Gly Ile Thr Leu Gly Met Asp Glu Leu Tyr Lys
    690                 695                 700

<210> SEQ ID NO 20
<211> LENGTH: 704
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (250)..(251)
<223> OTHER INFORMATION: Xaa can be any naturally occurring amino acid

<400> SEQUENCE: 20

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Tyr Thr Phe Gly Gly Gly Thr Lys Leu Glu Ile Lys
            100                 105                 110

Arg Ala Gly Gly Ser Ser Arg Ser Ser Ser Gly Gly Gly Gly Ser
        115                 120                 125

Gly Gly Gly Gly Gln Val Gln Leu Gln Gln Ser Gly Ala Glu Leu Val
130                 135                 140

Arg Pro Gly Ala Ser Val Thr Leu Ser Cys Lys Ala Ser Gly Tyr Thr
145                 150                 155                 160

Phe Thr Asp Tyr Glu Met His Trp Val Lys Gln Thr Pro Val His Gly
                165                 170                 175

Leu Glu Trp Ile Gly Thr Ile Asp Pro Glu Thr Ala Gly Thr Ala Tyr
            180                 185                 190

Asn Asn Gln Lys Phe Lys Gly Lys Ala Ile Leu Thr Ala Gly Lys Ser
        195                 200                 205

Ser Ser Thr Ala Tyr Met Glu Leu Arg Ser Leu Thr Ser Glu Asp Ser
    210                 215                 220

Ala Val Tyr Tyr Cys Thr Gly Val Thr Thr Trp Phe Ala Tyr Trp Gly
225                 230                 235                 240

Gln Gly Thr Leu Val Thr Val Ser Ala Xaa Xaa Ala Leu Ser Asn Ser
                245                 250                 255

Ile Met Tyr Phe Ser His Phe Val Pro Val Phe Leu Pro Ala Lys Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Ser Arg Pro Ala Ala Gly
    290                 295                 300

Gly Ala Val His Thr Arg Gly Leu Asp Leu Cys Tyr Leu Leu Asp Gly
305                 310                 315                 320

Ile Leu Phe Ile Tyr Gly Val Ile Ile Thr Ala Leu Tyr Leu Arg Ala
                325                 330                 335

Lys Phe Ser Arg Ser Ala Glu Thr Ala Ala Asn Leu Gln Asp Pro Asn
            340                 345                 350

Gln Leu Phe Asn Glu Leu Asn Leu Gly Arg Arg Glu Glu Phe Asp Val
        355                 360                 365

Leu Glu Lys Lys Arg Ala Arg Asp Pro Glu Met Gly Gly Lys Gln Gln
    370                 375                 380

Arg Arg Arg Asn Pro Gln Glu Gly Val Phe Asn Ala Leu Gln Lys Asp
385                 390                 395                 400

Lys Met Ala Glu Ala Phe Ser Glu Ile Gly Thr Lys Gly Glu Arg Arg
```

```
            405                 410                 415
Arg Gly Lys Gly His Asp Gly Leu Phe Gln Gly Leu Ser Thr Ala Thr
        420                 425                 430

Lys Asp Thr Phe Asp Ala Leu His Met Gln Thr Leu Ala Pro Arg Glu
        435                 440                 445

Gly Arg Gly Ser Leu Leu Thr Cys Gly Asp Val Glu Glu Asn Pro Gly
        450                 455                 460

Pro Met Val Ser Lys Gly Glu Leu Phe Thr Gly Val Val Pro Ile
465             470                 475                 480

Leu Val Glu Leu Asp Gly Asp Val Asn Gly His Lys Phe Ser Val Ser
                485                 490                 495

Gly Glu Gly Glu Gly Asp Ala Thr Tyr Gly Lys Leu Thr Leu Lys Phe
                500                 505                 510

Ile Cys Thr Thr Gly Lys Leu Pro Val Pro Trp Pro Thr Leu Val Thr
                515                 520                 525

Thr Leu Thr Tyr Gly Val Gln Cys Phe Ser Arg Tyr Pro Asp His Met
        530                 535                 540

Lys Gln His Asp Phe Phe Lys Ser Ala Met Pro Glu Gly Tyr Val Gln
545             550                 555                 560

Glu Arg Thr Ile Phe Phe Lys Asp Asp Gly Asn Tyr Lys Thr Arg Ala
                565                 570                 575

Glu Val Lys Phe Glu Gly Asp Thr Leu Val Asn Arg Ile Glu Leu Lys
                580                 585                 590

Gly Ile Asp Phe Lys Glu Asp Gly Asn Ile Leu Gly His Lys Leu Glu
                595                 600                 605

Tyr Asn Tyr Asn Ser His Asn Val Tyr Ile Met Ala Asp Lys Gln Lys
        610                 615                 620

Asn Gly Ile Lys Val Asn Phe Lys Ile Arg His Asn Ile Glu Asp Gly
625             630                 635                 640

Ser Val Gln Leu Ala Asp His Tyr Gln Gln Asn Thr Pro Ile Gly Asp
                645                 650                 655

Gly Pro Val Leu Leu Pro Asp Asn His Tyr Leu Ser Thr Gln Ser Ala
                660                 665                 670

Leu Ser Lys Asp Pro Asn Glu Lys Arg Asp His Met Val Leu Leu Glu
                675                 680                 685

Phe Val Thr Ala Ala Gly Ile Thr Leu Gly Met Asp Glu Leu Tyr Lys
        690                 695                 700

<210> SEQ ID NO 21
<211> LENGTH: 455
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (248)..(249)
<223> OTHER INFORMATION: Xaa can be any naturally occurring amino acid

<400> SEQUENCE: 21

Ile Val Leu Thr Gln Ser Pro Ala Ile Met Ser Ala Ser Pro Gly Glu
1               5                   10                  15

Lys Val Thr Met Thr Cys Ser Ala Ser Ser Arg Val Thr Tyr Met His
                20                  25                  30

Trp Tyr Gln Gln Arg Ser Gly Thr Ser Pro Lys Arg Trp Ile Tyr Asp
                35                  40                  45
```

-continued

```
Thr Ser Lys Leu Ala Ser Gly Val Pro Ala Arg Phe Ser Gly Ser Gly
 50                  55                  60
Ser Gly Thr Ser Tyr Ser Leu Thr Ile Ser Ser Met Glu Ala Glu Asp
 65                  70                  75                  80
Ala Ala Thr Tyr Tyr Cys Gln Gln Trp Gly Asn Asn Pro Gln Tyr Thr
                 85                  90                  95
Phe Gly Gly Gly Thr Arg Leu Glu Ile Lys Arg Gly Gly Gly Gly Ser
            100                 105                 110
Gly Gly Gly Gly Ser Gly Gly Gly Ser Gly Gly Gly Gly Ser Gln
            115                 120                 125
Val Thr Leu Lys Glu Ser Gly Pro Gly Ile Leu Gln Pro Ser Gln Thr
130                 135                 140
Leu Ser Leu Thr Cys Ser Phe Ser Gly Phe Ser Leu Ser Thr Ser Gly
145                 150                 155                 160
Thr Gly Val Gly Trp Ile Arg Gln Pro Ser Gly Lys Gly Leu Glu Trp
                165                 170                 175
Leu Ser His Ile Trp Trp Asp Asp Val Lys Arg Tyr Asn Pro Ala Leu
            180                 185                 190
Lys Ser Arg Leu Thr Ile Ser Arg Asp Thr Ser Tyr Ser Gln Val Phe
        195                 200                 205
Leu Arg Ile Ala Ser Val Asp Thr Ala Asp Thr Ala Thr Tyr Tyr Cys
210                 215                 220
Ala Arg Ile Leu Asp Gly Thr Gly Pro Met Asp Tyr Trp Gly Gln Gly
225                 230                 235                 240
Thr Ser Val Thr Val Ser Ser Xaa Xaa Glu Gln Lys Leu Ile Ser Glu
                245                 250                 255
Glu Asp Leu Ala Leu Ser Asn Ser Ile Met Tyr Phe Ser His Phe Val
            260                 265                 270
Pro Val Phe Leu Pro Ala Lys Pro Thr Thr Thr Pro Ala Pro Arg Pro
        275                 280                 285
Pro Thr Pro Ala Pro Thr Ile Ala Ser Gln Pro Leu Ser Leu Arg Pro
290                 295                 300
Glu Ala Ser Arg Pro Ala Ala Gly Gly Ala Val His Thr Arg Gly Leu
305                 310                 315                 320
Asp Leu Cys Tyr Leu Leu Asp Gly Ile Leu Phe Ile Tyr Gly Val Ile
                325                 330                 335
Ile Thr Ala Leu Tyr Leu Arg Ala Lys Phe Ser Arg Ser Ala Glu Thr
            340                 345                 350
Ala Ala Asn Leu Gln Asp Pro Asn Gln Leu Tyr Asn Glu Leu Asn Leu
        355                 360                 365
Gly Arg Arg Glu Glu Tyr Asp Val Leu Glu Lys Lys Arg Ala Arg Asp
370                 375                 380
Pro Glu Met Gly Gly Lys Gln Gln Arg Arg Arg Asn Pro Gln Glu Gly
385                 390                 395                 400
Val Tyr Asn Ala Leu Gln Lys Asp Lys Met Ala Glu Ala Tyr Ser Glu
                405                 410                 415
Ile Gly Thr Lys Gly Glu Arg Arg Arg Gly Lys Gly His Asp Gly Leu
            420                 425                 430
Tyr Gln Gly Leu Ser Thr Ala Thr Lys Asp Thr Tyr Asp Ala Leu His
        435                 440                 445
Met Gln Thr Leu Ala Pro Arg
450                 455
```

```
<210> SEQ ID NO 22
<211> LENGTH: 455
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (248)..(249)
<223> OTHER INFORMATION: Xaa can be any naturally occurring amino acid

<400> SEQUENCE: 22

Ile Val Leu Thr Gln Ser Pro Ala Ile Met Ser Ala Ser Pro Gly Glu
1               5                   10                  15

Lys Val Thr Met Thr Cys Ser Ala Ser Ser Arg Val Thr Tyr Met His
            20                  25                  30

Trp Tyr Gln Gln Arg Ser Gly Thr Ser Pro Lys Arg Trp Ile Tyr Asp
        35                  40                  45

Thr Ser Lys Leu Ala Ser Gly Val Pro Ala Arg Phe Ser Gly Ser Gly
    50                  55                  60

Ser Gly Thr Ser Tyr Ser Leu Thr Ile Ser Ser Met Glu Ala Glu Asp
65                  70                  75                  80

Ala Ala Thr Tyr Tyr Cys Gln Gln Trp Gly Asn Asn Pro Gln Tyr Thr
                85                  90                  95

Phe Gly Gly Gly Thr Arg Leu Glu Ile Lys Arg Gly Gly Gly Gly Ser
            100                 105                 110

Gly Gly Gly Gly Ser Gly Gly Gly Ser Gly Gly Gly Gly Ser Gln
        115                 120                 125

Val Thr Leu Lys Glu Ser Gly Pro Gly Ile Leu Gln Pro Ser Gln Thr
    130                 135                 140

Leu Ser Leu Thr Cys Ser Phe Ser Gly Phe Ser Leu Ser Thr Ser Gly
145                 150                 155                 160

Thr Gly Val Gly Trp Ile Arg Gln Pro Ser Gly Lys Gly Leu Glu Trp
                165                 170                 175

Leu Ser His Ile Trp Trp Asp Asp Val Lys Arg Tyr Asn Pro Ala Leu
            180                 185                 190

Lys Ser Arg Leu Thr Ile Ser Arg Asp Thr Ser Tyr Ser Gln Val Phe
        195                 200                 205

Leu Arg Ile Ala Ser Val Asp Thr Ala Asp Thr Ala Thr Tyr Tyr Cys
    210                 215                 220

Ala Arg Ile Leu Asp Gly Thr Gly Pro Met Asp Tyr Trp Gly Gln Gly
225                 230                 235                 240

Thr Ser Val Thr Val Ser Ser Xaa Xaa Glu Gln Lys Leu Ile Ser Glu
                245                 250                 255

Glu Asp Leu Ala Leu Ser Asn Ser Ile Met Tyr Phe Ser His Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Ser Arg Pro Ala Ala Gly Gly Ala Val His Thr Arg Gly Leu
305                 310                 315                 320

Asp Leu Cys Tyr Leu Leu Asp Gly Ile Leu Phe Ile Tyr Gly Val Ile
                325                 330                 335

Ile Thr Ala Leu Tyr Leu Arg Ala Lys Phe Ser Arg Ser Ala Glu Thr
            340                 345                 350
```

```
Ala Ala Asn Leu Gln Asp Pro Asn Gln Leu Phe Asn Glu Leu Asn Leu
            355                 360                 365

Gly Arg Arg Glu Glu Phe Asp Val Leu Glu Lys Lys Arg Ala Arg Asp
370                 375                 380

Pro Glu Met Gly Gly Lys Gln Gln Arg Arg Arg Asn Pro Gln Glu Gly
385                 390                 395                 400

Val Phe Asn Ala Leu Gln Lys Asp Lys Met Ala Glu Ala Phe Ser Glu
            405                 410                 415

Ile Gly Thr Lys Gly Glu Arg Arg Gly Lys Gly His Asp Gly Leu
            420                 425                 430

Phe Gln Gly Leu Ser Thr Ala Thr Lys Asp Thr Phe Asp Ala Leu His
            435                 440                 445

Met Gln Thr Leu Ala Pro Arg
450                 455

<210> SEQ ID NO 23
<211> LENGTH: 425
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (218)..(219)
<223> OTHER INFORMATION: Xaa can be any naturally occurring amino acid

<400> SEQUENCE: 23

Glu Gly Ser Ala Asp Tyr Lys Asp His Asp Gly Asp Tyr Lys Asp His
1               5                   10                  15

Asp Ile Asp Tyr Lys Asp Asp Asp Lys Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Xaa Xaa Glu Gln Lys Leu Ile
    210                 215                 220

Ser Glu Glu Asp Leu Ala Leu Ser Asn Ser Ile Met Tyr Phe Ser His
225                 230                 235                 240
```

```
Phe Val Pro Val Phe Leu Pro Ala Lys Pro Thr Thr Thr Pro Ala Pro
                245                 250                 255

Arg Pro Pro Thr Pro Ala Pro Thr Ile Ala Ser Gln Pro Leu Ser Leu
            260                 265                 270

Arg Pro Glu Ala Ser Arg Pro Ala Ala Gly Gly Ala Val His Thr Arg
            275                 280                 285

Gly Leu Asp Leu Cys Tyr Leu Leu Asp Gly Ile Leu Phe Ile Tyr Gly
            290                 295                 300

Val Ile Ile Thr Ala Leu Tyr Leu Arg Ala Lys Phe Ser Arg Ser Ala
305                 310                 315                 320

Glu Thr Ala Ala Asn Leu Gln Asp Pro Asn Gln Leu Tyr Asn Glu Leu
                325                 330                 335

Asn Leu Gly Arg Arg Glu Glu Tyr Asp Val Leu Glu Lys Lys Arg Ala
                340                 345                 350

Arg Asp Pro Glu Met Gly Gly Lys Gln Gln Arg Arg Arg Asn Pro Gln
            355                 360                 365

Glu Gly Val Tyr Asn Ala Leu Gln Lys Asp Lys Met Ala Glu Ala Tyr
            370                 375                 380

Ser Glu Ile Gly Thr Lys Gly Glu Arg Arg Arg Gly Lys Gly His Asp
385                 390                 395                 400

Gly Leu Tyr Gln Gly Leu Ser Thr Ala Thr Lys Asp Thr Tyr Asp Ala
                405                 410                 415

Leu His Met Gln Thr Leu Ala Pro Arg
                420                 425

<210> SEQ ID NO 24
<211> LENGTH: 425
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (218)..(219)
<223> OTHER INFORMATION: Xaa can be any naturally occurring amino acid

<400> SEQUENCE: 24

Glu Gly Ser Ala Asp Tyr Lys Asp His Asp Gly Asp Tyr Lys Asp His
1               5                   10                  15

Asp Ile Asp Tyr Lys Asp Asp Asp Lys Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
            130                 135                 140

Glu Gly Ile Gln Thr Leu Met Gly Arg Leu Glu Asp Gly Ser Pro Arg
```

```
                145                 150                 155                 160
Thr Gly Gln Ile Phe Lys Gln Thr Tyr Ser Lys Phe Asp Thr Asn Ser
                    165                 170                 175

His Asn Asp Asp Ala Leu Leu Lys Asn Tyr Gly Leu Leu Tyr Cys Phe
                    180                 185                 190

Arg Lys Asp Met Asp Lys Val Glu Thr Phe Leu Arg Ile Val Gln Cys
                    195                 200                 205

Arg Ser Val Glu Gly Ser Cys Gly Phe Xaa Xaa Glu Gln Lys Leu Ile
        210                 215                 220

Ser Glu Glu Asp Leu Ala Leu Ser Asn Ser Ile Met Tyr Phe Ser His
225                 230                 235                 240

Phe Val Pro Val Phe Leu Pro Ala Lys Pro Thr Thr Thr Pro Ala Pro
                    245                 250                 255

Arg Pro Pro Thr Pro Ala Pro Thr Ile Ala Ser Gln Pro Leu Ser Leu
                    260                 265                 270

Arg Pro Glu Ala Ser Arg Pro Ala Ala Gly Gly Ala Val His Thr Arg
                    275                 280                 285

Gly Leu Asp Leu Cys Tyr Leu Leu Asp Gly Ile Leu Phe Ile Tyr Gly
            290                 295                 300

Val Ile Ile Thr Ala Leu Tyr Leu Arg Ala Lys Phe Ser Arg Ser Ala
305                 310                 315                 320

Glu Thr Ala Ala Asn Leu Gln Asp Pro Asn Gln Leu Phe Asn Glu Leu
                    325                 330                 335

Asn Leu Gly Arg Arg Glu Glu Phe Asp Val Leu Glu Lys Lys Arg Ala
                    340                 345                 350

Arg Asp Pro Glu Met Gly Gly Lys Gln Gln Arg Arg Arg Asn Pro Gln
                    355                 360                 365

Glu Gly Val Phe Asn Ala Leu Gln Lys Asp Lys Met Ala Glu Ala Phe
            370                 375                 380

Ser Glu Ile Gly Thr Lys Gly Glu Arg Arg Gly Lys Gly His Asp
385                 390                 395                 400

Gly Leu Phe Gln Gly Leu Ser Thr Ala Thr Lys Asp Thr Phe Asp Ala
                    405                 410                 415

Leu His Met Gln Thr Leu Ala Pro Arg
                    420                 425

<210> SEQ ID NO 25
<211> LENGTH: 218
<212> TYPE: PRT
<213> ORGANISM: Homo sapiens

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                    20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95
```

```
Asp Leu Pro Leu Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
            210                 215

<210> SEQ ID NO 26
<211> LENGTH: 447
<212> TYPE: PRT
<213> ORGANISM: Homo sapiens

<400> SEQUENCE: 26

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 27
<211> LENGTH: 891
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (684)..(685)
<223> OTHER INFORMATION: Xaa can be any naturally occurring amino acid

<400> SEQUENCE: 27

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
```

```
                    -continued 145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Lys Thr Tyr Thr Cys Asn Val Asp His Lys
                195                 200                 205
Pro Ser Asn Thr Lys Val Asp Lys Arg Val Glu Ser Lys Tyr Gly Pro
210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
                260                 265                 270
Val Gln Phe Asn Trp Tyr Val Asp Gly Val Glu Val His Asn Ala Lys
                275                 280                 285
Thr Lys Pro Arg Glu Glu Gln Phe Asn Ser Thr Tyr Arg Val Val Ser
                290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Gln Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
                370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly Lys Gly
                435                 440                 445
Gly Ser Ser Arg Ser Ser Ser Gly Gly Gly Ser Gly Gly Gly
450                 455                 460
Gly Glu Ile Val Leu Thr Gln Ser Pro Ala Thr Leu Ser Leu Ser Pro
465                 470                 475                 480
Gly Glu Arg Ala Thr Leu Ser Cys Arg Ala Ser Lys Gly Val Ser Thr
                485                 490                 495
Ser Gly Tyr Ser Tyr Leu His Trp Tyr Gln Gln Lys Pro Gly Gln Ala
                500                 505                 510
Pro Arg Leu Leu Ile Tyr Leu Ala Ser Tyr Leu Glu Ser Gly Val Pro
                515                 520                 525
Ala Arg Phe Ser Gly Ser Gly Ser Gly Thr Asp Phe Thr Leu Thr Ile
                530                 535                 540
Ser Ser Leu Glu Pro Glu Asp Phe Ala Val Tyr Tyr Cys Gln His Ser
545                 550                 555                 560
Arg Asp Leu Pro Leu Thr Phe Gly Gly Gly Thr Lys Val Glu Ile Lys
                565                 570                 575
```

```
Arg Thr Val Ala Ala Pro Ser Val Phe Ile Phe Pro Pro Ser Asp Glu
            580                 585                 590

Gln Leu Lys Ser Gly Thr Ala Ser Val Val Cys Leu Leu Asn Asn Phe
        595                 600                 605

Tyr Pro Arg Glu Ala Lys Val Gln Trp Lys Val Asp Asn Ala Leu Gln
    610                 615                 620

Ser Gly Asn Ser Gln Glu Ser Val Thr Glu Gln Asp Ser Lys Asp Ser
625                 630                 635                 640

Thr Tyr Ser Leu Ser Ser Thr Leu Thr Leu Ser Lys Ala Asp Tyr Glu
                645                 650                 655

Lys His Lys Val Tyr Ala Cys Glu Val Thr His Gln Gly Leu Ser Ser
            660                 665                 670

Pro Val Thr Lys Ser Phe Asn Arg Gly Glu Cys Xaa Xaa Glu Gln Lys
        675                 680                 685

Leu Ile Ser Glu Glu Asp Leu Ala Leu Ser Asn Ser Ile Met Tyr Phe
    690                 695                 700

Ser His Phe Val Pro Val Phe Leu Pro Ala Lys Pro Thr Thr Thr Pro
705                 710                 715                 720

Ala Pro Arg Pro Pro Thr Pro Ala Pro Thr Ile Ala Ser Gln Pro Leu
                725                 730                 735

Ser Leu Arg Pro Glu Ala Ser Arg Pro Ala Ala Gly Gly Ala Val His
            740                 745                 750

Thr Arg Gly Leu Asp Leu Cys Tyr Leu Leu Asp Gly Ile Leu Phe Ile
        755                 760                 765

Tyr Gly Val Ile Ile Thr Ala Leu Tyr Leu Arg Ala Lys Phe Ser Arg
    770                 775                 780

Ser Ala Glu Thr Ala Ala Asn Leu Gln Asp Pro Asn Gln Leu Tyr Asn
785                 790                 795                 800

Glu Leu Asn Leu Gly Arg Arg Glu Glu Tyr Asp Val Leu Glu Lys Lys
                805                 810                 815

Arg Ala Arg Asp Pro Glu Met Gly Gly Lys Gln Gln Arg Arg Arg Asn
            820                 825                 830

Pro Gln Glu Gly Val Tyr Asn Ala Leu Gln Lys Asp Lys Met Ala Glu
        835                 840                 845

Ala Tyr Ser Glu Ile Gly Thr Lys Gly Glu Arg Arg Arg Gly Lys Gly
    850                 855                 860

His Asp Gly Leu Tyr Gln Gly Leu Ser Thr Ala Thr Lys Asp Thr Tyr
865                 870                 875                 880

Asp Ala Leu His Met Gln Thr Leu Ala Pro Arg
                885                 890

<210> SEQ ID NO 28
<211> LENGTH: 891
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (684)..(685)
<223> OTHER INFORMATION: Xaa can be any naturally occurring amino acid

<400> SEQUENCE: 28

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
```

```
                20                  25                  30
Tyr Met Tyr Trp Val Arg Gln Ala Pro Gly Gln Gly Leu Glu Trp Met
                35                  40                  45
Gly Gly Ile Asn Pro Ser Asn Gly Gly Thr Asn Phe Asn Glu Lys Phe
            50                  55                  60
Lys Asn Arg Val Thr Leu Thr Thr Asp Ser Thr Thr Thr Ala Tyr
 65                  70                  75                  80
Met Glu Leu Lys Ser Leu Gln Phe Asp Asp Thr Ala Val Tyr Tyr Cys
                85                  90                  95
Ala Arg Arg Asp Tyr Arg Phe Asp Met Gly Phe Asp Tyr Trp Gly Gln
                100                 105                 110
Gly Thr Thr Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Lys Thr Tyr Thr Cys Asn Val Asp His Lys
                195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
                260                 265                 270
Val Gln Phe Asn Trp Tyr Val Asp Gly Val Glu Val His Asn Ala Lys
            275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Gln Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly Lys Gly
            435                 440                 445
```

```
Gly Ser Ser Arg Ser Ser Ser Gly Gly Gly Ser Gly Gly Gly
    450                 455                 460
Gly Glu Ile Val Leu Thr Gln Ser Pro Ala Thr Leu Ser Leu Ser Pro
465                 470                 475                 480
Gly Glu Arg Ala Thr Leu Ser Cys Arg Ala Ser Lys Gly Val Ser Thr
                485                 490                 495
Ser Gly Tyr Ser Tyr Leu His Trp Tyr Gln Gln Lys Pro Gly Gln Ala
            500                 505                 510
Pro Arg Leu Leu Ile Tyr Leu Ala Ser Tyr Leu Glu Ser Gly Val Pro
        515                 520                 525
Ala Arg Phe Ser Gly Ser Gly Ser Gly Thr Asp Phe Thr Leu Thr Ile
    530                 535                 540
Ser Ser Leu Glu Pro Glu Asp Phe Ala Val Tyr Tyr Cys Gln His Ser
545                 550                 555                 560
Arg Asp Leu Pro Leu Thr Phe Gly Gly Gly Thr Lys Val Glu Ile Lys
                565                 570                 575
Arg Thr Val Ala Ala Pro Ser Val Phe Ile Phe Pro Pro Ser Asp Glu
            580                 585                 590
Gln Leu Lys Ser Gly Thr Ala Ser Val Val Cys Leu Leu Asn Asn Phe
        595                 600                 605
Tyr Pro Arg Glu Ala Lys Val Gln Trp Lys Val Asp Asn Ala Leu Gln
    610                 615                 620
Ser Gly Asn Ser Gln Glu Ser Val Thr Glu Gln Asp Ser Lys Asp Ser
625                 630                 635                 640
Thr Tyr Ser Leu Ser Ser Thr Leu Thr Leu Ser Lys Ala Asp Tyr Glu
                645                 650                 655
Lys His Lys Val Tyr Ala Cys Glu Val Thr His Gln Gly Leu Ser Ser
            660                 665                 670
Pro Val Thr Lys Ser Phe Asn Arg Gly Glu Cys Xaa Xaa Glu Gln Lys
        675                 680                 685
Leu Ile Ser Glu Glu Asp Leu Ala Leu Ser Asn Ser Ile Met Tyr Phe
    690                 695                 700
Ser His Phe Val Pro Val Phe Leu Pro Ala Lys Pro Thr Thr Thr Pro
705                 710                 715                 720
Ala Pro Arg Pro Pro Thr Pro Ala Pro Thr Ile Ala Ser Gln Pro Leu
                725                 730                 735
Ser Leu Arg Pro Glu Ala Ser Arg Pro Ala Ala Gly Gly Ala Val His
            740                 745                 750
Thr Arg Gly Leu Asp Leu Cys Tyr Leu Leu Asp Gly Ile Leu Phe Ile
        755                 760                 765
Tyr Gly Val Ile Ile Thr Ala Leu Tyr Leu Arg Ala Lys Phe Ser Arg
    770                 775                 780
Ser Ala Glu Thr Ala Ala Asn Leu Gln Asp Pro Asn Gln Leu Phe Asn
785                 790                 795                 800
Glu Leu Asn Leu Gly Arg Arg Glu Glu Phe Asp Val Leu Glu Lys Lys
                805                 810                 815
Arg Ala Arg Asp Pro Glu Met Gly Gly Lys Gln Gln Arg Arg Arg Asn
            820                 825                 830
Pro Gln Glu Gly Val Phe Asn Ala Leu Gln Lys Asp Lys Met Ala Glu
        835                 840                 845
Ala Phe Ser Glu Ile Gly Thr Lys Gly Glu Arg Arg Arg Gly Lys Gly
    850                 855                 860
```

```
His Asp Gly Leu Phe Gln Gly Leu Ser Thr Ala Thr Lys Asp Thr Phe
865                 870                 875                 880

Asp Ala Leu His Met Gln Thr Leu Ala Pro Arg
                885                 890

<210> SEQ ID NO 29
<211> LENGTH: 21
<212> TYPE: PRT
<213> ORGANISM: Mus musculus

<400> SEQUENCE: 29

Leu Cys Tyr Leu Leu Asp Gly Ile Leu Phe Ile Tyr Gly Val Ile Ile
1               5                   10                  15

Thr Ala Leu Tyr Leu
                20

<210> SEQ ID NO 30
<211> LENGTH: 113
<212> TYPE: PRT
<213> ORGANISM: Mus musculus

<400> SEQUENCE: 30

Arg Ala Lys Phe Ser Arg Ser Ala Glu Thr Ala Ala Asn Leu Gln Asp
1               5                   10                  15

Pro Asn Gln Leu Tyr Asn Glu Leu Asn Leu Gly Arg Arg Glu Glu Tyr
                20                  25                  30

Asp Val Leu Glu Lys Lys Arg Ala Arg Asp Pro Glu Met Gly Gly Lys
            35                  40                  45

Gln Gln Arg Arg Arg Asn Pro Gln Glu Gly Val Tyr Asn Ala Leu Gln
    50                  55                  60

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Thr Leu Ala Pro
                100                 105                 110

Arg

<210> SEQ ID NO 31
<211> LENGTH: 113
<212> TYPE: PRT
<213> ORGANISM: Artificial
<220> FEATURE:
<223> OTHER INFORMATION: Synthetic

<400> SEQUENCE: 31

Arg Ala Lys Phe Ser Arg Ser Ala Glu Thr Ala Ala Asn Leu Gln Asp
1               5                   10                  15

Pro Asn Gln Leu Phe Asn Glu Leu Asn Leu Gly Arg Arg Glu Glu Phe
                20                  25                  30

Asp Val Leu Glu Lys Lys Arg Ala Arg Asp Pro Glu Met Gly Gly Lys
            35                  40                  45

Gln Gln Arg Arg Arg Asn Pro Gln Glu Gly Val Phe Asn Ala Leu Gln
    50                  55                  60

Lys Asp Lys Met Ala Glu Ala Phe Ser Glu Ile Gly Thr Lys Gly Glu
65                  70                  75                  80

Arg Arg Arg Gly Lys Gly His Asp Gly Leu Phe Gln Gly Leu Ser Thr
                85                  90                  95
```

Ala Thr Lys Asp Thr Phe Asp Ala Leu His Met Gln Thr Leu Ala Pro
            100                 105                 110
Arg

<210> SEQ ID NO 32
<211> LENGTH: 39
<212> TYPE: PRT
<213> ORGANISM: Homo sapiens

<400> SEQUENCE: 32

Lys Cys Phe Cys Lys His Arg Ser Cys Phe Arg Arg Asn Glu Ala Ser
1               5                   10                  15

Arg Glu Thr Asn Asn Ser Leu Thr Phe Gly Pro Glu Glu Leu Ala Leu
            20                  25                  30

Ala Glu Gln Thr Val Phe Leu
        35

<210> SEQ ID NO 33
<211> LENGTH: 239
<212> TYPE: PRT
<213> ORGANISM: Artificial
<220> FEATURE:
<223> OTHER INFORMATION: Synthetic

<400> SEQUENCE: 33

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 34

```
<211> LENGTH: 22
<212> TYPE: PRT
<213> ORGANISM: Homo sapiens

<400> SEQUENCE: 34

Met Ala Thr Gly Ser Arg Thr Ser Leu Leu Leu Ala Phe Gly Leu Leu
1               5                   10                  15

Cys Leu Pro Trp Leu Gln
            20
```

NON-CYTOTOXIC MODIFIED CELLS AND USE THEREOF

CROSS-REFERENCE TO RELATED APPLICATION

This application is a National Phase of PCT Patent Application No. PCT/IL2017/051133 having International filing date of Oct. 10, 2017, which claims the benefit of priority from U.S. Provisional Patent Application No. 62/406,005 filed on Oct. 10, 2016. The contents of the above applications are all incorporated by reference as if fully set forth herein in their entirety.

FIELD OF INVENTION

The present invention is directed to the field of cell therapy.

BACKGROUND OF THE INVENTION

There are many known antibodies, antibody fragments and ligands that can specifically bind various receptors and act as either agonists or antagonists. Such agonistic/antagonistic have been used for the treatment of various diseases. However, a major limitation for the use of such molecules is the complexity of targeting the molecule to a specific organ, tissue and/or specific cell type. It is difficult to transfer large molecules across the blood brain barrier, and to deep parenchymal areas as well. Further these molecules often have short half-life, high immunogenicity or never reach the intended target region at all.

Cellular delivery of these potential therapeutic molecules is one possible avenue that may circumvent many of these problems. However, such a solution relies on the ability of the cell to home to the desired treatment area or area of disease. Further, in order to perform an autologous or allogenic treatment that does not induce an immune response, it must be possible to culture and expand the primary cells outside of the body of the subject. Immune cells offer an unexplored avenue for the delivery of these therapeutic molecules, because current delivery methods would result in activation of the immune cell and thus localized inflammation at best and direct killing of the cell that is being treated at worst. A method of delivering therapeutic agonists and antagonists to diseased cells anywhere in the body, without harming those cells or increasing inflammation in the diseased area is greatly desired.

SUMMARY OF THE INVENTION

The present invention provides methods of modulating signaling by a target receptor in a target cell and methods of treating a subject suffering from a disease or disorder wherein the disease or disorder is associated with the target receptor.

According to a first aspect, there is provided a method of modulating signaling by a target receptor in a target cell, the method comprising contacting the target cell with a modified cell comprising a chimeric transmembrane polypeptide comprising at least one extracellular target receptor-binding domain, a transmembrane domain and an intracellular domain, wherein the intracellular domain does not transduce a signal, and wherein the modified cell serves as a ligand and thereby modulates signaling by a target receptor in a target cell.

According to another aspect, there is provided a method of treating a subject suffering from a disease or disorder, the method comprising:
  a. providing a cell capable of homing to the site of the disease or disorder;
  b. expressing in the cell a chimeric transmembrane polypeptide comprising at least one extracellular target receptor-binding domain, a transmembrane domain and an intracellular domain, wherein the intracellular domain is not capable of transducing any signal and wherein the target receptor is associated with the disease or disorder; and
  c. administering the cell expressing the chimeric transmembrane polypeptide to the subject;
thereby treating the subject suffering from a disease or disorder.

In some embodiments, the signaling by a target cell comprises a signaling cascade in the target cell. In some embodiments, the modulating comprises inducing or inhibiting. In some embodiments, inducing signaling comprises phosphorylation of a residue within a signaling domain of the target receptor. In some embodiments, inducing signaling comprises upregulation of a level of a downstream target of the target receptor. In some embodiments, inhibiting signaling comprises down-regulation of a level of a downstream target of said target receptor.

In some embodiments, the chimeric transmembrane polypeptide comprises an extracellular domain and intracellular domain that are from different proteins.

In some embodiments, the extracellular domain comprises an agonist or antagonist of said target receptor.

In some embodiments, the target receptor-binding domain comprises an immunoglobulin variable heavy chain domain (VH) and an immunoglobulin variable light chain domain (VL). In some embodiments, the VH and VL are connected by a peptide linker. In some embodiments, the linker comprises the amino acid sequence GGSSRSSSSGGGGSGGGG (SEQ ID NO: 4) or GGGGSGGGGSGGGGSGGGGS (SEQ ID NO: 5).

In some embodiments, the transmembrane domain is a single-pass transmembrane domain. In some embodiments, the transmembrane domain comprises a CD3 transmembrane domain. In some embodiments, the CD3 transmembrane domain comprises the sequence LCYLLDGILFIYGVIITALYL (SEQ ID NO: 29).

In some embodiments, the chimeric transmembrane polypeptide further comprises an extracellular and membrane proximal hinge region. In some embodiments, the hinge region comprises a CD-8 hinge region. In some embodiments, the CD-8 hinge region comprises the amino acid sequence ALSNSIMYFSHFVPVFLPAKPTTTPAPRPPT-PAPTIASQPLSLRPEASRPAAGGAV HTRGLD (SEQ ID NO: 7).

In some embodiments, the signal comprises phosphorylation of a residue within a signaling domain of said intracellular domain. In some embodiments, the signal induces activation of immune cell effector function. In some embodiments, the signal induces secretion of at least one cytokine from said modified cell. In some embodiments, the at least one cytokine is interleukin-2 (IL-2). In some embodiments, the signal induces activation of ZAP-70 kinase.

In some embodiments, the intracellular domain comprises an artificial amino acid sequence of sufficient length and charge to allow for detectable expression of the chimeric transmembrane polypeptide on a surface of the modified cell. In some embodiments, detection of the chimeric transmembrane polypeptide on a surface of the modified cell comprises FACS. In some embodiments, the intracellular domain comprises an artificial amino acid sequence of sufficient length and charge to allow for mobility of the chimeric transmembrane polypeptide within a membrane of said modified immune cell.

In some embodiments, the intracellular domain comprises an intracellular domain of any transmembrane protein other than CD3, CD28, OX-40 CD80, CD86 and a T-cell receptor (TCR). In some embodiments, the intracellular domain comprises CD3 Zeta chain mutated to be unable to transduce an activating signal.

In some embodiments, the CD3 Zeta chain comprises the amino acid sequence RAKFSRSAETAANLQDPNQLY-NELNLGRREEYDVLEKKRARDPEMGGKQQRR RNPQEGVYNALQKDKMAEAYSEI-GTKGERRRGKGHDGLYQGLSTATKDTYDA LHMQT-LAPR (SEQ ID NO: 30).

In some embodiments, at least one tyrosine of said CD3 Zeta chain is mutated, and the mutation renders the intracellular domain unable to transduce an activating signal. In some embodiments, the at least one tyrosine is mutated to a phenylalanine. In some embodiments, all tyrosines of said CD3 Zeta chain have been mutated. In some embodiments, all tyrosines are mutated to phenylalanines.

In some embodiments, the intracellular domain comprises the amino acid sequence RAKFSR-SAETAANLQDPNQLFNELNLGRREEFDVLEKK-RARDPEMGGKQQRR RNPQEGVFNALQKDK-MAEAFSEIGTKGERRRGKGHDGLFQGLSTATKDT-FDAL HMQTLAPR (SEQ ID NO: 31).

In some embodiments, the intracellular domain is not capable of transducing any signal that renders the modified cell harmful to the target cell. In some embodiments, the intracellular domain is inert.

In some embodiments, the chimeric transmembrane polypeptide further comprises a tag. In some embodiments, the tag is selected from a GFP tag and a Myc tag.

In some embodiments, the target receptor is associated with a disease or disorder. In some embodiments, the target receptor is selected from GHR, GLP1R, TrkB, and PD-1.

In some embodiments, the target receptor is TrkB and the anti-TrkB antigen binding domain comprises an amino acid sequence with at least 70% identity to a sequence provided in any one of SEQ ID NO: 10, SEQ ID NO: 11, SEQ ID NO: 12, or SEQ ID NO: 13. In some embodiments, the chimeric transmembrane polypeptide comprises an amino acid sequence as set forth in SEQ ID NO: 18, or SEQ ID NO:20.

In some embodiments, the target receptor is GLP1R and the anti-GLP1R antigen binding domain comprises an amino acid sequence with at least 70% identity to a sequence provided in any one of SEQ ID NO: 14, or SEQ ID NO: 15. In some embodiments, the chimeric transmembrane polypeptide has the amino acid sequence as set forth in SEQ ID NO: 22.

In some embodiments, the target receptor is GHR and said target receptor-binding domain comprises a growth hormone (GH). In some embodiments, the GH comprises an amino acid sequence with at least 70% identity to the sequence provided in SEQ ID NO: 16. In some embodiments, the chimeric transmembrane polypeptide has the amino acid sequence as set forth in SEQ ID NO: 24.

In some embodiments, the target receptor is PD-1 and the anti-PD-1 antigen binding domain comprises an amino acid sequence with at least 70% identity to the sequence provided in SEQ ID NO: 25 or SEQ ID NO: 26. In some embodiments, the chimeric transmembrane polypeptide has the amino acid sequence as set forth in SEQ ID NO: 28.

In some embodiments, the chimeric transmembrane polypeptide has at least 95% sequence identity to an amino acid sequence of any one of SEQ ID NOs: 18, 20, 22, 24 or 28 and is not capable of transducing a signal.

In some embodiments, the modified cell or provided cell is an immune cell. In some embodiments, the immune cell is selected from a T-cell, a natural killer (NK) cell, a B-cell, a myeloid cell, a macrophage, a monocyte, a neutrophil, an antigen presenting cell and a dendritic cell.

In some embodiments, the modified cell or provided cell is derived from a primary human cell from a human donor, and wherein said modified primary human cell is suitable for use in human therapy. In some embodiments, the provided cell is autologous to the subject. In some embodiments, the provided cell is allogenic to the subject.

In some embodiments, the target cell is in culture. In some embodiments, the target cell is in a subject.

In some embodiments, the providing comprises extracting a primary cell from said subject.

In some embodiments, the activation of said target receptor on a cell of the subject treats the disease or disorder, and the extracellular receptor-binding domain comprises an agonist of the target receptor. In some embodiments, the inhibition of the receptor on a cell of the subject treats the disease or disorder, and the extracellular receptor-binding domain comprises an antagonist of the target receptor.

In some embodiments, the target receptor is TrkB and the disease or disorder is a neurological disease or disorder. In some embodiments, the neurological disease or disorder is selected from: Alzheimer's disease, depression, memory loss, amyotrophic lateral sclerosis (ALS), epilepsy and brain cancer.

In some embodiments, the target receptor is GLP1R and the disease or disorder is a metabolic or cardiovascular disease or disorder. In some embodiments, the metabolic disease or disorder is selected from: diabetes, obesity, glycogen storage disease, Parkinson's disease and mitochondrial myopathy. In some embodiments, the cardiovascular disease or disorder is selected from: stroke, myocardial infarction, cardiac ischemia, and coronary artery disease.

In some embodiments, the target receptor is GHR and the disease or disorder is a growth disease or disorder. In some embodiments, the growth disease or disorder is selected from: acromegaly, growth hormone deficiency, cancer, Turner syndrome, and Prader-Willi syndrome.

In some embodiments, the target receptor is PD-1 and the disease or disorder is an immune disease or disorder or cancer. In some embodiments, the immune disease or disorder is selected from: lupus, rheumatoid arthritis, psoriasis, Graves' disease, immune-mediated inflammation, and celiac disease. In some embodiments, the disease or disorder is cancer and the target receptor-binding domain comprises a PD-1 antagonist.

According to another aspect, there is provided a pharmaceutical composition, comprising a modified cell comprising a chimeric transmembrane polypeptide comprising at least one extracellular target receptor-binding domain, a transmembrane domain and an intracellular domain, wherein the intracellular domain does not transduce a signal and a pharmaceutically acceptable carrier, excipient, or adjuvant.

In some embodiments, the compositions of the invention are for use in treating a disease or disorder associated with the target receptor. In some embodiments, the composition comprises at least 1 million modified cells.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
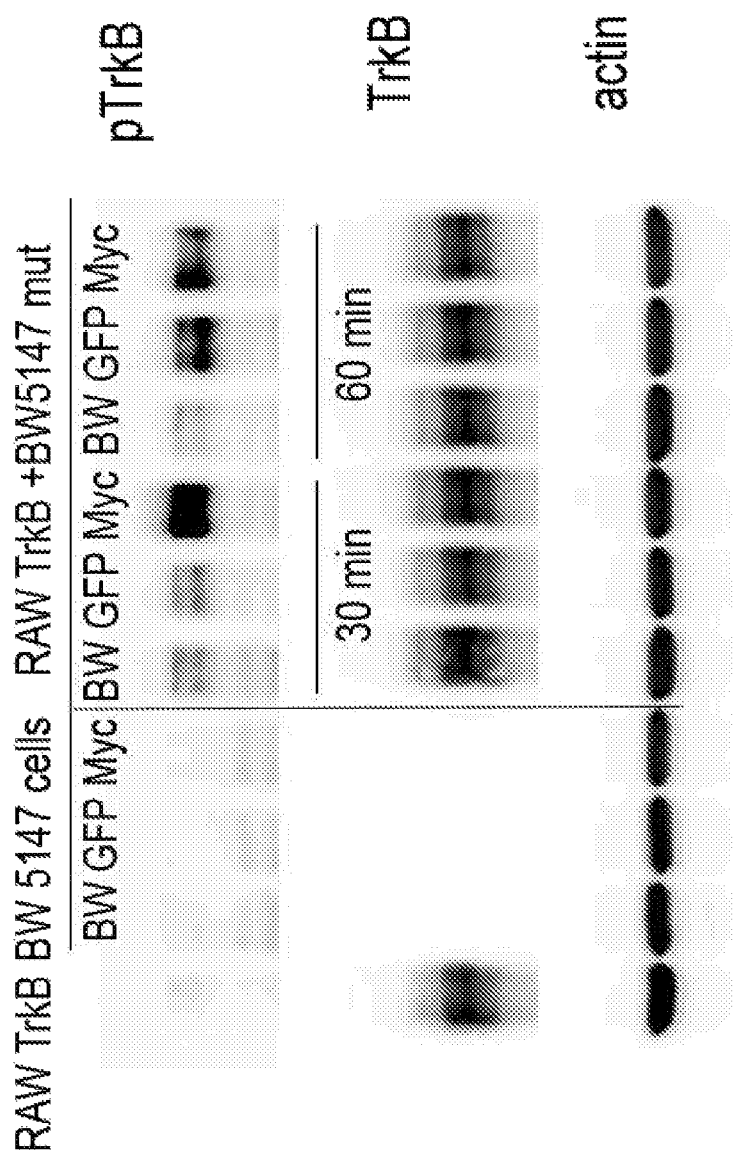
FIG. 1A is photographic exposure of western-blots detecting pTrkB, total TrkB and actin.

The present invention provides compositions and methods for treatment of diseases by modulation of the activity of a receptor on a target cell. The present invention exploits the ability of cells of the immune system to migrate within the body and to accumulate at specific niches within organs. Such immune cells are used as a delivery platform for a molecule of interest that is expressed and anchored to their membrane. The anchored therapeutic molecule is in the extracellular domain of a chimeric transmembrane polypeptide, which comprises an intracellular domain that is not capable of transducing an immune cell activating signal. In this way biding of the therapeutic molecule to its target receptor will modulate (e.g., activate or inactive) that target receptor, but not activate the immune cell itself.

By a first aspect, there is provided a method of modulating signaling by a target receptor in a target cell, the method comprising contacting the target cell with a modified cell comprising a chimeric transmembrane polypeptide comprising at least one extracellular target receptor-binding domain, a transmembrane domain and an intracellular domain, wherein the intracellular domain is not capable of transducing any signal, thereby modulating signaling by a target receptor in a target cell.

By another aspect, there is provided a method of modulating signaling by a target receptor in a target cell, the method comprising contacting the target cell with a modified immune cell comprising a chimeric transmembrane polypeptide comprising at least one extracellular target receptor-binding domain, a transmembrane domain and an intracellular domain, wherein the intracellular domain is not capable of transducing an immune cell activating signal, thereby modulating signaling by a target receptor in a target cell.

By another aspect, there is provided a method of treating a subject suffering from a disease or disorder, the method comprising:
  a. Providing an immune cell;
  b. expressing in said immune cell a chimeric transmembrane polypeptide comprising at least one extracellular target receptor-binding domain, a transmembrane domain and an intracellular domain, wherein said intracellular domain is not capable of transducing an immune cell activating signal and wherein said target receptor is associated with said disease or disorder; and
  c. administering said immune cell expressing said chimeric transmembrane polypeptide to said subject;
thereby treating said subject suffering from a disease or disorder.

By another aspect, there is provided a method of treating a subject suffering from a disease or disorder, the method comprising:
  a. Providing a cell capable of homing to a site of said disease or disorder;
  b. expressing in said cell a chimeric transmembrane polypeptide comprising at least one extracellular target receptor-binding domain, a transmembrane domain and an intracellular domain, wherein said intracellular domain is inert and wherein said target receptor is associated with said disease or disorder; and
  c. administering said cell expressing said chimeric transmembrane polypeptide to said subject;
thereby treating said subject suffering from a disease or disorder.

By another aspect, there is provided a chimeric transmembrane polypeptide comprising at least one extracellular target receptor-binding domain, a transmembrane domain and an intracellular domain, wherein the intracellular domain is not capable of transducing an immune cell activating signal. In some embodiments, the intracellular domain is not capable of transducing any signal.

As used herein, the term "signaling" refers to intracellular signal transduction. Signal transduction is well known in the art, and refers to transmission of a signal through a series of molecular events to effect a physiological change in a cell. In some embodiments, the signaling comprises a signaling cascade within the target cell. In some embodiments, signal transduction comprises phosphorylation of signaling proteins. In some embodiments, inducing signaling comprises phosphorylation of a residue within a signaling domain of the target receptor. In some embodiments, inducing signaling comprises phosphorylation of a residue within a signaling domain of a protein of the signaling cascade. In some embodiments, the phosphorylated residue is a tyrosine residue. In some embodiments, inducing signaling comprises upregulation of a level of a downstream target of the target receptor. In some embodiments, inhibiting signaling comprises down-regulation of a level of a downstream target of the target receptor.

In some embodiments, inducing signaling comprises at least a 10%, 20%, 30%, 40%, 50%, 60%, 70%, 80%, 90%, or 100% increase in signaling. Each possibility represents a separate embodiment of the invention. In some embodiments, inhibiting signaling comprises at least a 10%, 20%, 30%, 40%, 50%, 60%, 70%, 80%, 90%, 95% or 100% reduction in signaling. Each possibility represents a separate embodiment of the invention.

Measuring changes in signaling is well known in the art and any method of confirming alterations in signaling may be used to perform the methods of the invention. Such methods of measuring include but are not limited to, measuring phosphorylation of a signaling domain of the target receptor or another signaling protein known to be downstream of the receptor in a signaling cascade. Measuring expression levels of proteins known to be up- or down-regulated by signaling may also be employed. Example of such molecules include, but are not limited to cytokines, transcription factors, and effector proteins.

In some embodiments, the target cell is a cell of a diseased tissue. In some embodiments, the tissue is selected from: the brain, a muscle, the heart, the lungs, the pancreas, the skin, the liver, the reproductive system, the digestive system and the secretory system. In some embodiments, the target cell is a hematological cell. In some embodiments, the target cell is an immunological cell. In some embodiments, the target cell is selected from: a neuron, a muscle cell, a bone cell, a blood cell, a lymph cell, a fibroblast, an immune cell, an insulin-producing cell and a cardiac cell.

In some embodiments, the target cell is in culture. In some embodiments, the target cell is in a subject. In some embodiments, the target cell is in a subject and the modified cell is allogenic to the subject. In some embodiments, the target cell is in a subject and the modified cell is autologous to the subject. In some embodiments, the target cell is in a subject and the modified cell is further modified to not elicit an immune response or elicit a reduced immune response upon administration to the subject.

In some embodiments, the target receptor is a receptor associated with a disease or disorder. In some embodiments, the target receptor is on a diseased cell or diseased tissue of a subject. In some embodiments, activation of the target receptor treats or ameliorates the disease or disorder, and the extracellular receptor-binding domain comprises an agonist of the target receptor. In some embodiments, inhibition of the target receptor treats or ameliorates the disease or disorder, and the extracellular receptor-binding domain comprises an antagonist of the target receptor.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

Modified Cells

By another aspect, there is provided a modified cell comprising a chimeric transmembrane polypeptide comprising at least one extracellular target receptor-binding domain, a transmembrane domain and an intracellular domain, wherein the intracellular domain is not capable of transducing an immune cell activating signal. In some embodiments, the intracellular domain is not capable of transducing any signal. In some embodiments, the intracellular domain is inert. In some embodiments, the methods of the invention are performed by contacting a target cell with a modified cell of the invention. In some embodiments, the methods of the invention are performed by administering to a subject in need thereof, a modified cell of the invention.

In some embodiments, the modified cell of the invention is any cell which can home to a desired location or target cell in a body. In some embodiments, the modified cell of the invention is any cell which can home to a site of disease in the body. In some embodiments, the cells are fibroblasts. In some embodiments, the cells are mesenchymal stem cells (MSCs). In some embodiments, the cells are embryonic stem cells (ESCs) or induced pluripotent stem cells (IPSCs). In some embodiments, the cells are pluripotent stem cells (PSCs). In some embodiments, the cells are immune cells. In some embodiments, the immune cell is selected from a T-cell, a natural killer (NK) cell, a B-cell, a myeloid cell, a macrophage, a monocyte, a neutrophil, an antigen presenting cell and a dendritic cell. In some embodiments, the immune cell is a T-cell. In some embodiments, the T-cell is a CD4+ or a CD8+ T-cell. In some embodiment, the immune cell is partially activated to facilitate homing and synapse formation. In some embodiments, the immune cell is capable of crossing the blood brain barrier (BBB). In some embodiments, the immune cell is capable of crossing the blood testes barrier (BTB).

Cell homing may depend on the location or tissue of a target cell or diseased cell. In embodiments wherein the target cell is at a wound, the modified cell may be a fibroblast. In embodiments wherein the target cell is in the brain, the modified cell may be a CD4+ T-cell. In embodiments wherein the target cell is in the pancreas, the modified cell may be a B-cell.

Modified cells of the present invention are genetically modified to express and anchor to their membrane an agonist or an antagonist or the target receptor. In some embodiments, the agonist/antagonist is a single chain antibody which has agonistic/antagonistic properties for a target receptor, referred hereafter as single chain agonist/antagonist antibody (SCAAB). The cells of the present invention are used as carrier cells which mediate the delivery of the agonist/antagonist to the desired target site in the body of a subject. In some embodiments, the carrier cells are introduced to the body of a subject where they migrate and accumulate at a desired organ and/or at a specific niche. It will be understood to one skilled in the art, that as the cells are carriers of the agonist and/or antagonist, cytotoxic activation of the modified cell is not required for the methods of the invention. Indeed, as activation of immune cell effector function initiates an immune response and/or renders the cell cytotoxic, activation of effector function in the cell is disadvantageous and not desired.

In some embodiments, the methods of the invention seek to activate or inhibit a target receptor on a target cell, and do not wish to kill the target cell as is likely to result if the immune cell becomes fully activated upon binding. As such the chimeric transmembrane polypeptides of the invention have intracellular regions that are not capable of transducing an immune cell activation signal, leading to harming target cells, and thus immune cells, such as CD8 T cells and NK cells, are not rendered cytotoxic upon binding to the target. In some embodiments, the modified immune cells of the invention are not cytotoxic. In some embodiments, the modified immune cells of the invention are not rendered cytotoxic by binding to the target receptor. In some embodiments, the modified immune cells of the invention do not secrete cytokines as a result of binding to the target receptor.

In some embodiments, the modified cells do not harm the target cell. In some embodiments, the modified cells do not kill the target cells. In some embodiments, the modified cells are not detrimental to the target cell.

In some embodiments, in which the modified cell is an immune cell the cytoplasmic domain is not capable of transducing an immune cell activating signal. In some embodiments, in which the modified cell is an immune cell the cytoplasmic domain is not capable of transducing any signal into the cell that would result is the modified cell harming the target cell. In some embodiments, in which the modified cell is an immune cell the cytoplasmic domain is not capable of transducing any signal into the cell. In some embodiments, in which the modified cell is another homing cell other than an immune cell the cytoplasmic domain is not capable of transducing any signal into the cell that would result in the modified cell harming the target cell. In some embodiments, in which the modified cell is another homing cell other than an immune cell the cytoplasmic domain is not capable of transducing any signal into the cell.

In some embodiments, the modified cell is a primary cell. In some embodiments, the modified cell is derived from a primary cell from a human donor, and wherein said modified primary human cell is suitable for use in human therapy. In some embodiments, the primary cell is cultured in cell culture media after removal from the human donor. In some embodiments, the modified cell is a daughter or descendant cell from the primary cell put in culture. Culturing primary cells for return to the donor is well known in the art, any culture condition that can be used to keep the cell healthy suitable for return to the donor is suitable. Instructions for primary cell culture can be obtained from ATCC, Sigma Aldrich as two non-limiting examples. In some embodiments, the primary cell is expanded in culture and the expanded modified cells are returned to the donor. In some embodiments, the providing comprises extracting a primary immune cell from the patient.

The term "cell culture medium" refers to any liquid medium which enables cells proliferation. Growth media are known in the art and can be selected depending of the type of cell to be grown. For example, a growth medium for use in growing mammalian cells is Dulbecco's Modified Eagle Medium (DMEM) which can be supplemented with heat inactivated fetal bovine serum.

In some embodiments, modified cells are cultured under effective conditions, which allow for the expression of high amounts of chimeric polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the chimeric polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

As used herein, the terms "peptide", "polypeptide" and "protein" are used interchangeably to refer to a polymer of amino acid residues. In another embodiment, the terms "peptide", "polypeptide" and "protein" as used herein encompass native peptides, peptidomimetics (typically including non-peptide bonds or other synthetic modifications) and the peptide analogues peptoids and semipeptoids or any combination thereof. In another embodiment, the peptides polypeptides and proteins described have modifications rendering them more stable while in the body or more capable of penetrating into cells. In one embodiment, the terms "peptide", "polypeptide" and "protein" apply to naturally occurring amino acid polymers. In another embodiment, the terms "peptide", "polypeptide" and "protein" apply to amino acid polymers in which one or more amino acid residue is an artificial chemical analogue of a corresponding naturally occurring amino acid.

As used herein, the term "chimeric" polypeptide refers to a polypeptide in which at least two fragments from distinct naturally occurring proteins have been combined into a single non-naturally occurring protein. Chimeric proteins are well known to one skilled in the art, and will have a distinct domain or fragment which can be identified as being derived for a known protein and at least one other distinct domain or fragment which can be identified as being derived from a second known protein. In some embodiments, a naturally occurring protein is not a chimeric protein. In some embodiments, a naturally occurring protein with a leader sequence or peptide from a different protein is not considered a chimeric peptide. It will be understood that as the leader sequence or peptide is not expressed in the mature protein, it cannot be considered to contribute to the polypeptide being chimeric. In some embodiments, the chimeric transmembrane polypeptide comprises an extracellular domain for a first protein and an intracellular domain from a second protein.

As used herein, a "fragment" refers to a portion of a protein which is of sufficient size or structure so as to still be recognizable as part of the whole protein. In some embodiments, a fragment is the entire protein. As used herein, the term "derived from" or "corresponding to" refers to construction of an amino acid sequence based on the knowledge of a sequence using any one of the suitable means known to one skilled in the art, e.g. chemical synthesis in accordance with standard protocols in the art.

As used herein, a "leader sequence" or "leader peptide" are synonymous and refer to the 15-30 mostly hydrophobic amino acids found that the N-terminus of proteins which are inserted into a membrane. Most commonly the leader sequence is cleaved from the mature protein after insertion into a membrane. These sequences are often required for proper insertion into the endoplasmic reticulum, correct orientation of transmembrane proteins and robust expression on the cell surface. Generally, the leader sequence from any transmembrane protein that is expressed on the cell surface may be exchanged with the leader sequence from any other transmembrane protein expressed on the cell surface and robust surface expression is still achieved. Leader peptides from proteins predominantly expressed intracellularly, such as mitochondrial proteins for example, should not ideally be used, but if surface expression is achieved are still optional. Examples of leader sequences which may be used for insertion of a chimeric transmembrane polypeptide of the invention into a cell membrane, and thus efficient cell surface expression, include but are not limited to, MDMRVPAQLLGLLLLWLSGARC (SEQ ID NO: 1), MDMRVPAQLLGLLLLWLSGARCQ (SEQ ID NO: 2), and MATGSRTSLLLAFGLLCLPWLQEGSQA (SEQ ID NO: 3).

As used herein, a "transmembrane polypeptide" refers to a protein that is anchored in and spans the plasma membrane. As such a transmembrane polypeptide must comprise at least extracellular amino acid, at least one intracellular amino acid and amino acid sequence which is within the plasma membrane. Transmembrane proteins are well known in the art, and it will be understood to one skilled in the art that a GPI anchored polypeptide is not a polypeptide of the invention as it is not "transmembrane" and does not have an intracellular domain.

In some embodiments, the modified cell of the invention comprises more than one chimeric transmembrane polypeptide. In some embodiments, a single chimeric transmembrane polypeptide comprises more than one target receptor-binding domain. In some embodiments, more than one target receptor-binding domain target the same receptor. In some embodiments, two distinct receptor-binding domains target different receptors. As such a single modified cell can have more than one target receptor and more than one target cell.

Extracellular Domain

In some embodiments, the extracellular domain comprises an agonist or antagonist of the target receptor. In some embodiments, the target receptor-binding domain comprises an antibody's antigen binding domain. In some embodiments, the extracellular domain contains more than one target receptor-binding domain. In some embodiments, the extracellular domain may bind to more than one target receptor. In some embodiments, the extracellular domain may comprise more than one agonist or antagonist for the target receptor. In some embodiments, the target receptor-binding domain comprises an immunoglobulin variable heavy chain domain (VH) and an immunoglobulin variable light chain domain (VL). In some embodiments, the extracellular domain comprises more than one antibody antigen binding domain. As the methods of the invention are for modulating a target receptor, it will be understood that extracellular domains that merely bind a target receptor but do not activate or inhibit that receptor are not embodiments of the invention. Further, target receptor-binding domains merely used for targeting of the modified cell to a target cell also would not modulate target receptor signaling and also are not embodiments of the invention.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. An antibody may be from any species. The term antibody also includes binding fragments, including, but not limited to Fv, Fab, Fab', F(ab')2 single stranded antibody (svFC), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)–Fc fusions and scFv-scFv-Fc fusions.

In some embodiments, the VH and VL are connected by a peptide linker. In the design of antigen binding fragments for use as antibodies peptide linkers between the VH and VL are well known, and any linker effective in generating a binding pocket that successfully binds to the target receptor may be used. In some embodiments, the peptide linker comprises the amino acid sequence GGSSRSSSSGGGGSGGG (SEQ ID NO: 4) or GGGGSGGGGSGGGGSGGGGS (SEQ ID NO: 5).

In some embodiments, the target receptor-binding domain binds the target receptor with a dissociation constant (Kd) of at least 0.1, 0.2, 0.3, 0.4, 0.5, 1, 5, 10, 20, 30, 40, 50, 60, 70, 80, 90, or 100 pM. Each possibility represents a separate embodiment of the invention. In some embodiments, the target receptor-binding domain binds the target receptor with a Kd of between 0.1 and 100, 0.1 and 200, 0.1 and 300, 0.1 and 400, 0.1 and 500, 0.1 and 600, 0.1 and 700, 0.1 and 800, 0.1 and 900, 0.1 and 1000, 0.1 and 2000, 0.1 and 3000, 0.5 and 100, 0.5 and 200, 0.5 and 300, 0.5 and 400, 0.5 and 500, 0.5 and 600, 0.5 and 700, 0.5 and 800, 0.5 and 900, 0.5 and 1000, 0.5 and 2000, 0.5 and 3000, 1 and 100, 1 and 200, 1 and 300, 1 and 400, 1 and 500, 1 and 600, 1 and 700, 1 and 800, 1 and 900, 1 and 1000, 1 and 2000, or 1 and 3000 pM. Each possibility represents a separate embodiment of the invention.

In some embodiments, the target receptor-binding domain binds the target receptor with a half maximal effective concentration (EC50) of at least 0.1, 0.2, 0.3, 0.4, 0.5, 1, 5, 10, 20, 30, 40, 50, 60, 70, 80, 90, or 100 nM. Each possibility represents a separate embodiment of the invention. In some embodiments, the target receptor-binding domain binds the target receptor with a EC50 of between 0.1 and 100, 0.1 and 200, 0.1 and 300, 0.1 and 400, 0.1 and 500, 0.1 and 600, 0.1 and 700, 0.1 and 800, 0.1 and 900, 0.1 and 1000, 0.1 and 2000, 0.1 and 3000, 0.5 and 100, 0.5 and 200, 0.5 and 300, 0.5 and 400, 0.5 and 500, 0.5 and 600, 0.5 and 700, 0.5 and 800, 0.5 and 900, 0.5 and 1000, 0.5 and 2000, 0.5 and 3000, 1 and 100, 1 and 200, 1 and 300, 1 and 400, 1 and 500, 1 and 600, 1 and 700, 1 and 800, 1 and 900, 1 and 1000, 1 and 2000, or 1 and 3000 nM. Each possibility represents a separate embodiment of the invention.

Transmembrane Domain

Transmembrane domains are well known in the art and generally contain hydrophobic residues. In some embodiments, the transmembrane domain is a known transmembrane domain from a naturally occurring protein. In some embodiments, the transmembrane domain is from a murine transmembrane protein. In some embodiments, the transmembrane domain is from a human transmembrane protein. In some embodiments, the transmembrane domain is a synthetic transmembrane domain. The methods and compositions of the invention may be performed with any transmembrane domain that results in anchorage of the chimeric polypeptide of the invention in the plasma membrane with the target receptor-binding domain in the extracellular region and the intracellular region lacking the capability of transducing an immune cell activating signal.

In some embodiments, the transmembrane domain is a single-pass transmembrane domain. In some embodiments, the transmembrane domain comprises an odd number of transmembrane regions. Once skilled in the art will understand that if an even number of transmembrane regions are present in the protein than the intracellular region will be an intracellular loop found between two transmembrane regions. In some embodiments, the intracellular region is at the C-terminus of the protein. In some embodiments, the intracellular region is at the N-terminus of the protein. In some embodiments, the intracellular region is an intracellular loop between two transmembrane domains.

In some embodiments, the transmembrane domain comprises the CD3 transmembrane domain. In some embodiments, the transmembrane domain consists of the CD3 transmembrane domain. In some embodiments, the CD3 transmembrane domain comprises the sequence LCYLL-DGILFIYGVIITALYL (SEQ ID NO: 29). In some embodiments, the CD3 transmembrane domain consists of the sequence provided in SEQ ID NO: 29.

In some embodiments, the chimeric transmembrane polypeptide further comprises a hinge region. In some embodiments, the hinge region is an extracellular region. In some embodiments, the hinge region is membrane proximal. In some embodiments, the hinge region is an extracellular and membrane proximal region. In some embodiments, the hinge region comprises an immunoglobulin hinge region. Use of a hinge region in antibodies and chimeric proteins is well known in the art. In some embodiments, the hinge region links the VH and VL domains. In some embodiments, only polypeptides comprising VH and VL domains comprise a hinge domain.

In some embodiments, the hinge region comprises a CD-8 hinge region. In some embodiments, the hinge region consists of a CD-8 hinge region. In some embodiments, the CD-8 hinge region comprises the amino acid sequence ALSNSIMYFSHFVPVFLPAKPTTTPAPRPPTPAPTIA-SQPLSLRPEASRPAAGGAV HTRGLD (SEQ ID NO: 7). In some embodiments, the CD-8 hinge region consists of the amino acid sequence provided in SEQ ID NO: 7.

Intracellular Domain

In some embodiments, the intracellular domain of the chimeric transmembrane polypeptide of the invention is not capable of transducing an immune cell activating signal. In some embodiments, the intracellular domain of the chimeric transmembrane polypeptide of the invention is not capable of transducing any signal that results in the modified cell harming the target cell. In some embodiments, the intracellular domain of the chimeric transmembrane polypeptide of the invention is not capable of transducing any signal. In some embodiments, the intracellular domain of the chimeric transmembrane polypeptide of the invention is inert. As used herein, the term "inert" refers to the inability to the protein region to affect signaling in any way. An inert protein domain not only cannot transduce a signal, but it cannot regulate or modulate a signal. An inert cytoplasmic domain may still affect the proteins ability to migrate within the membrane or affect the proteins expression or orientation in the membrane.

In some embodiments, immune cell activation comprises effector function activation. In some embodiments, immune cell activation comprises at least one of secretion of cytokines, release of antibodies, activation of ZAP-10 kinase, immune cell proliferation and upregulation of surface expression at least one of CD69, CD71, CD25, HLA-DR and CTLA-4. In some embodiments, immune cell activation comprises secretion of IL-2. In some embodiments, an immune cell activating signal induces activation of ZAP-70 kinase. In some embodiments, an immune cell activating signal comprises phosphorylation of a residue within a signaling domain of an intracellular domain of a transmembrane protein. In some embodiments, the residue is a tyrosine residue. In some embodiments, an immune cell activating signal comprises activation of effector function. In some embodiments, an immune cell activating signal comprises phosphorylation of a tyrosine within a signaling domain of an intracellular domain of a protein of the T-cell receptor complex or a costimulatory protein. In some embodiments, the costimulatory protein is any one of CD28, OX-40, CD80 (B7-1) and CD86 (B7-2). In some embodiments, an immune cell activating signal comprises co-stimulation of the TCR by any one of CD28, OX-40, CD80 and CD86.

In some embodiments, transducing an immune cell activating signal comprises costimulatory signaling. In some embodiments, transducing an immune cell activating signal comprises any function that absent this function the signal would not be transduced, and the cell not activated. In some embodiments, transducing the signal comprises a kinase cascade. In some embodiments, transducing the signal comprises protein-protein binding of kinase molecules and costimulatory molecules.

In some embodiments, a cytoplasmic domain capable of transducing an immune cell activating signal comprises an immunoreceptor tyrosine-based activation motif (ITAM) domain. Immune cell activating receptors are well known in the art. Non-limiting examples of immune cell activating proteins, who comprise an ITAM domain, and whose signaling domains cannot be used in the cytoplasmic domain of the chimeric polypeptide of the invention without mutation to abolish signaling are provided in Table 1.

TABLE 1

| Symbol | Description | Gcid |
|---|---|---|
| SYK | Spleen Associated Tyrosine Kinase | GC09P090831 |
| NFAM1 | NFAT Activating Protein with ITAM Motif 1 | GC22M042380 |
| STAM2 | Signal Transducing Adaptor Molecule 2 | GC02M152116 |
| STAM | Signal Transducing Adaptor Molecule | GC10P017645 |
| ZAP70 | Zeta Chain Of T-Cell Receptor Associated Protein Kinase 70 | GC02P097696 |
| TYROBP | TYRO Protein Tyrosine Kinase Binding Protein | GC19M035904 |
| LCK | LCK Proto-Oncogene, Src Family Tyrosine Kinase | GC01P032251 |
| FLNA | Filamin A | GC0XM154348 |
| CD79A | CD79a Molecule | GC19P041877 |
| CD247 | CD247 Molecule | GC01M167399 |
| CARD9 | Caspase Recruitment Domain Family Member 9 | GC09M136361 |
| FCER1G | Fc Fragment of IgE Receptor Ig | GC01P161215 |
| CLEC4E | C-Type Lectin Domain Family 4 Member E | GC12M008535 |
| CD79B | CD79b Molecule | GC17M063928 |
| FCGR2A | Fc Fragment of IgG Receptor IIa | GC01P161505 |
| CD3E | CD3e Molecule | GC11P118304 |
| PIK3CB | Phosphatidylinositol-4,5-Bisphosphate 3-Kinase Catalytic Subunit Beta | GC03M138652 |
| RASGRP1 | RAS Guanyl Releasing Protein 1 | GC15M038488 |
| CD300LB | CD300 Molecule Like Family Member B | GC17M074520 |
| PILRB | Paired Immunoglobin-Like Type 2 Receptor Beta | GC07P100353 |
| GCSAM | Germinal Center Associated Signaling and Motility | GC03M112120 |
| BCR | BCR, RhoGEF And GTPase Activating Protein | GC22P023179 |
| CEACAM4 | Carcinoembryonic Antigen Related Cell Adhesion Molecule 4 | GC19M041618 |
| GP6 | Glycoprotein VI Platelet | GC19M055013 |
| GRB2 | Growth Factor Receptor Bound Protein 2 | GC17M075318 |
| SHC1 | SHC Adaptor Protein 1 | GC01M154962 |
| EZR | Ezrin | GC06M158765 |
| FCAR | Fc Fragment of IgA Receptor | GC19P054983 |
| CD300LD | CD300 Molecule Like Family Member D | GC17M074579 |
| LYN | LYN Proto-Oncogene, Src Family Tyrosine Kinase | GC08P055879 |
| PLCG2 | Phospholipase C Gamma 2 | GC16P081773 |
| OSCAR | Osteoclast Associated, Immunoglobulin-Like Receptor | GC19M054094 |

TABLE 1-continued

| Symbol | Description | Gcid |
|---|---|---|
| CD3D | CD3d Molecule | GC11M118338 |
| CD3G | CD3g Molecule | GC11P118344 |
| RHOH | Ras Homolog Family Member H | GC04P040192 |
| FCGR2C | Fc Fragment of IgG Receptor IIc (Gene/Pseudogene) | GC01P161551 |
| AKT1 | AKT Serine/Threonine Kinase 1 | GC14M104769 |
| BTK | Bruton Tyrosine Kinase | GC0XM101349 |
| STAT1 | Signal Transducer and Activator of Transcription 1 | GC02M190964 |
| EGF | Epidermal Growth Factor | GC04P109912 |
| ITGB2 | Integrin Subunit Beta 2 | GC21M044885 |
| CHUK | Conserved Helix-Loop-Helix Ubiquitous Kinase | GC10M100188 |
| TLR2 | Toll Like Receptor 2 | GC04P153684 |
| ICAM1 | Intercellular Adhesion Molecule 1 | GC19P010270 |
| FYN | FYN Proto-Oncogene, Src Family Tyrosine Kinase | GC06M111660 |
| PIK3R1 | Phosphoinositide-3-Kinase Regulatory Subunit 1 | GC05P068215 |
| ITGA2B | Integrin Subunit Alpha 2b | GC17M044373 |
| ITGB3 | Integrin Subunit Beta 3 | GC17P047254 |
| ITGAV | Integrin Subunit Alpha V | GC02P186589 |
| KRT18 | Keratin 18 | GC12P052948 |
| PTK2B | Protein Tyrosine Kinase 2 Beta | GC08P027311 |
| CREB1 | CAMP Responsive Element Binding Protein 1 | GC02P207529 |
| RDX | Radixin | GC11M110134 |
| STAT2 | Signal Transducer and Activator of Transcription 2 | GC12M056341 |
| NR4A1 | Nuclear Receptor Subfamily 4 Group A Member 1 | GC12P052022 |
| FCGR2B | Fc Fragment of IgG Receptor IIb | GC01P161663 |
| BLNK | B-Cell Linker | GC10M096191 |
| NLRP3 | NLR Family Pyrin Domain Containing 3 | GC01P247415 |
| NEDD4 | Neural Precursor Cell Expressed, Developmentally Down-Regulated 4, E3 Ubiquitin Protein Ligase | GC15M055826 |
| MSN | Moesin | GC0XP065588 |
| MS4A1 | Membrane Spanning 4-Domains A1 | GC11P060474 |
| LAT | Linker for Activation Of T-Cells | GC16P028998 |
| INPP5D | Inositol Polyphosphate-5-Phosphatase D | GC02P233059 |
| IL18R1 | Interleukin 18 Receptor 1 | GC02P102345 |
| LCP2 | Lymphocyte Cytosolic Protein 2 | GC05M170246 |
| S100A8 | S100 Calcium Binding Protein A8 | GC01M153391 |
| PTPRT | Protein Tyrosine Phosphatase, Receptor Type T | GC20M042072 |
| SELPLG | Selectin P Ligand | GC12M108621 |
| CD300A | CD300a Molecule | GC17P074466 |
| CD244 | CD244 Molecule | GC01M160799 |
| SLAMF6 | SLAM Family Member 6 | GC01M160454 |
| ETV5 | ETS Variant 5 | GC03M186046 |
| IFNA1 | Interferon Alpha 1 | GC09P021441 |
| NCR2 | Natural Cytotoxicity Triggering Receptor 2 | GC06P041303 |
| RASA2 | RAS P21 Protein Activator 2 | GC03P141487 |
| LAT2 | Linker for Activation Of T-Cells Family Member 2 | GC07P074199 |
| CD300C | CD300c Molecule | GC17P074544 |
| CLEC1B | C-Type Lectin Domain Family 1 Member B | GC12M011530 |
| FCRL3 | Fc Receptor Like 3 | GC01M157674 |
| FHOD1 | Formin Homology 2 Domain Containing 1 | GC16M067263 |
| TNIP3 | TNFAIP3 Interacting Protein 3 | GC04M121131 |
| PILRA | Paired Immunoglobin Like Type 2 Receptor Alpha | GC07P100367 |
| KLRF1 | Killer Cell Lectin Like Receptor F1 | GC12P009827 |
| SH2D4B | SH2 Domain Containing 4B | GC10P080914 |
| TARM1 | T-Cell-Interacting, Activating Receptor on Myeloid Cells 1 | GC19M054069 |

In some embodiments, the intracellular domain comprises an intracellular domain of a transmembrane protein not expressed in immune cells. In some embodiments, the intracellular domain comprises an intracellular domain of a transmembrane protein expressed in immune cells, but not involved in cellular activation. In some embodiments, the intracellular domain comprises an intracellular domain capable of transducing an immune cell activation signal which has been mutated to be unable to transduce this signal. In some embodiments, the intracellular domain comprises an artificial amino acid sequence.

One skilled in the art will appreciate that the intracellular domain has other functions beyond signaling. The length, charge, and amino acid motifs of the intracellular domain can modulate proper insertion in the membrane, surface expression, protein folding, protein recycling and longevity, and mobility with the membrane among other aspects of the proteins and membranes dynamics.

In some embodiments, the intracellular domain comprises at least 1, 3, 5, 10, 15, 20, 25, 30, 35, 40, 45, 50, 75 or 100 amino acids. Each possibility represents a separate embodiment of the invention. In some embodiments, the intracellular domain comprises at most 10, 15, 20, 25, 30, 40, 45, 50, 75, 100, 150, 200, 250, 300, 350, 400, 450 or 500 amino acids. Each possibility represents a separate embodiment of the invention.

In some embodiments, the intracellular domain comprises at least one positively charged amino acid. In some embodiments, the intracellular domain comprises at least one positively charged amino acid within 5 amino acids from the end of the transmembrane domain. Positively charged amino acids include lysine (K), arginine (R) and histidine (H), as well as positively charged synthetic amino acids. One skilled in the art will appreciate that positive charge may aid in proper orientation of the polypeptide within the membrane and robust surface expression.)

In some embodiments, the intracellular domain comprises an amino acid sequence of sufficient length and charge to allow for detectable expression of the chimeric transmembrane polypeptide on a surface of said modified cell. In some embodiments, detection of the chimeric transmembrane polypeptide on a surface of the modified cell comprises FACS. FACS is a well-known technique, and so long as no cell-permeabilization step is included, can be used to confirm surface expression of a protein. In some embodiments, the chimeric transmembrane polypeptide of the invention further comprises a tag. In some embodiments, the tag is in the extracellular region. In some embodiments, the tag is in the extracellular region and an antibody against the tag is used to confirm surface expression. In some embodiments, the tag is in the intracellular region. The tag may be positioned anywhere in the chimeric protein such that it does not interfere with receptor binding, does not interfere with robust surface expression and does not interfere with the mobility of the protein within the plasma membrane. In some embodiments, the tag is selected from a Myc tag and a fluorescent tag. In some embodiments, a Myc-tag comprises the amino acid sequence EQKLISEEDL (SEQ ID NO: 6). In some embodiments, the fluorescent tag is GFP. In some embodiments, the GFP tag is eGFP. In some embodiments, the GFP tag comprises the amino acid sequence MVSKGEELFTGVVPIL-VELDGDVNGHKFSVSGEGEGDATYGKLTLK-FICTTGKL PVPWPTLVT-TLTYGVQCFSRYPDHMKQHDFFKSAMPEGYVQERTI-FFKDDGNY KTRAEVKFEGDTLVNRIELKGIDFKEDGNILGHK-LEYNYNSHNVYIMADKQKN GIKVNFKIRHNIEDGSVQLADHYQQNT-

PIGDGPVLLPDNHYLSTQSALSKDPNE KRDHMVLLEFVTAAGITLGMDELYK (SEQ ID NO: 33).

In some embodiments, the intracellular domain comprises an amino acid sequence of sufficient length and charge to allow for mobility of the chimeric transmembrane polypeptide within a membrane of the modified cell. Lateral movement of a protein within a membrane can be regulated by many factors, among them the cytoplasmic region of the protein. Activation of the target receptor requires clustering of the chimeric protein at the synapse with the target cell. Thus, activation can be used to confirm that a chimeric protein is capable of lateral movement. Further tagged proteins may be visualized in vivo by the tag if the tag is fluorescent. Live field microscopy, and live cell imaging can be used to confirm lateral movement of the chimeric polypeptide within the membrane.

In some embodiments, the intracellular domain does not comprise an endoplasmic reticulum (ER) retention signal or mitochondrial-targeting motif. ER-retention signals are short motifs, usually only 3 amino acids long and comprising lysines and arginines, that cause a transmembrane protein to be retained in the ER and not be expressed on the cell surface. Mitochondrial targeting motifs are short amino acid sequences that target a protein to the mitochondria and not the plasma membrane. As the polypeptides of the invention must be expressed on the cell surface, motifs and signals that retain or target the polypeptide to any subcellular location or organelle other than the plasma membrane, should be avoided, although so long as some surface expression is achieved the intracellular domain may be used.

In some embodiments, the intracellular domain comprises an unmodified intracellular domain of any protein other than a protein that is capable of transducing an immune cell activation signal. In some embodiments, the intracellular domain comprises an unmodified intracellular domain of any protein other than CD3, CD28, OX-40 CD80, CD86 and a T-cell receptor (TCR). In some embodiments, the intracellular domain comprises an unmodified intracellular domain of any protein other than CD3, CD28, OX-40, CD80, and CD86. In some embodiments, the intracellular domain comprises an unmodified intracellular domain of any protein other than CD3. In some embodiments, the intracellular domain comprises an unmodified intracellular domain of any protein other than CD3 and CD80. In some embodiments, the intracellular domain comprises an unmodified intracellular domain of any protein other than CD3 and CD28. In some embodiments, the intracellular domain comprises an unmodified intracellular domain of any protein other than CD3, CD28 and CD80.

In some embodiments, the intracellular domain comprises a mutated intracellular domain of any protein capable of transducing an immune cell activation signal, wherein said mutating renders the intracellular domain unable to transduce an activating signal. In some embodiments, a mutated intracellular domain comprises mutation of at least one tyrosine residue of a signaling domain. In some embodiments, the signaling domain is an ITAM domain. In some embodiments, all tyrosines residues of the intracellular domain are mutated. In some embodiments, the tyrosine is mutated to an amino acid that cannot be phosphorylated. In some embodiments, the tyrosine is mutated to phenylalanine.

In some embodiments, the intracellular domain comprises a CD3 zeta chain mutated to be unable to transduce an activating signal. In some embodiments, CD3 Zeta chain comprises the amino acid sequence RAKFSRSAETAANLQDPNQLYNELNLGRREEYDVLEKK-RARDPEMGGKQQRR RNPQEGVYNALQKDK-MAEAYSEIGTKGERRRGKGHDGLYQGLSTATKD-TYDA LHMQTLAPR (SEQ ID NO: 30). In some embodiments, mutated CD3 zeta chain comprises the amino acid sequence RAKFSRSAETAANLQDPNQLFNELNLGR-REEFDVLEKKRARDPEMGGKQQRR RNPQEGVFNALQKDKMAEAFSEI-GTKGERRRGKGHDGLFQGLSTATKDTFDAL HMQTL-APR (SEQ ID NO: 31).

In some embodiments, the intracellular domain comprises a CD80 (B7-1) cytoplasmic tail mutated to be unable to transduce an activating signal. In some embodiments, the intracellular domain comprises a CD80 (B7-1) cytoplasmic tail mutated to be unable to co-stimulate the TCR. In some embodiments, the CD80 cytoplasmic tail comprises the amino acid sequence KCFCKHRSCFRRNEAS-RETNNSLTFGPEELALAEQTVFL (SEQ ID NO: 32). In some embodiments, mutated CD80 cytoplasmic tail comprises mutation of the RRNE motif at amino acids 11-14 of SEQ ID NO: 32. In some embodiments, the RRNE is mutated to AAAA. In some embodiments, mutated CD80 cytoplasmic tail comprises mutation of at least one serine of the cytoplasmic tail. In some embodiments, the serine is mutated to an alanine. In some embodiments, the serine at position 16 of SEQ ID NO: 32 is mutated. In some embodiments, the serine at position 22 of SEQ ID NO: 32 is mutated. In some embodiments the serine at position 16 and the serine at position 22 or SEQ ID NO: 32 are mutated. In some embodiments, the RRNE motif and at least one serine are mutated.

In some embodiments, the intracellular domain is inert. As used herein, an "inert" domain is not capable of any signaling. In some embodiments, an inert domain has no function. In some embodiments, the intracellular domain is not capable of any signaling. In some embodiments, the intracellular domain has been mutated so as to abrogate any signaling capability. In some embodiments, the intracellular domain is incapable of contributing to immune cell activation in any way.

The term "embryonic stem cell" refers to stem cells derived from the undifferentiated inner mass of a human embryo. Such cells are pluripotent, and capable of differentiating, or being differentiated by means known to one ordinary in the art, into cells of any lineage. In order for a hESC to be considered undifferentiated, it must continue to express stem cell markers or not express markers of differentiated cells.

ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, (University of California at San Francisco); and HI, H7, H9, HI 3, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g, mice, rats, hamster, primate, etc. (Thomson et al. (1998) Science 282:1145; Thomson et al. (1995) Proc. Natl. Acad. Sci USA 92:7844; Thomson et al, (1996) Biol. Reprod. 55:254; Shamblott et al., Proc. Natl. Acad. Sci. USA 95:13726, 1998). In culture, ESCs typically grow as flat colonies with large nucleocytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806. Methods for proliferating hESCs in the undifferentiated form are described in WO 99/20741, WO 01/51616, and WO 03/020920.

By "induced pluripotent stem cell" or "iPSC" it is meant a pluripotent stem cell (PSC) that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26al, TERT, and zfp42. Examples of methods of generating and characterizing iPSCs may be found in, for example, U.S. Patent Publication Nos. US20090047263, US20090068742, US20090191159, US20090227032, US20090246875, and US20090304646. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

The term PSC refers to pluripotent stem cells regardless of their derivation, the term PSC encompasses the terms ESC and iPSC, as well as the term embryonic germ stem cells (EGSC), which are another example of a PSC. By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235. PSCs may be in the form of an established cell line, they may be obtained directly from primary embryonic tissue, or they may be derived from a somatic cell. PSCs can be the modified cells of the methods described herein.

Target Receptors

In some embodiments, the target receptor is selected from: Growth Hormone Receptor (GHR), Glucagon-like peptide 1 receptor (GLP1R), Tyrosine receptor kinase B/Tropomyosin receptor kinase B (TrkB), and Programmed cell Death protein 1 (PD-1).

In some embodiments, the target receptor is TrkB and the target receptor-binding domain comprises a VL comprising the amino acid sequence DVVMTQLPLSLPVILGDQASISCRSSQSLIHSNGNTYLHWYLQKPGQSPKLLIYKVSNRFSGVPDRFSGSGSGTDFTLKISRVEAEDLGVYFCSQSTHVPFTFGSGTKLEI KRA (SEQ ID NO: 10). In some embodiments, the target receptor is TrkB and the target receptor-binding domain comprises a VH comprising the amino acid sequence QVQLQQSGPELVKPGASVKLSCKASGYTFTSYDINWVKQRPGQGLEWIGWIYPRDGSIKFNEKFKGKATLTVDTSSSTAYMELHSLTSEDSAAYFCARRGRLLLYGF AYWGQGTLVTVSA (SEQ ID NO: 11). In some embodiments, the target receptor is TrkB and the target receptor-binding domain comprises SEQ ID NO:10 and SEQ ID NO: 11. In some embodiments, the target receptor is TrkB and the target receptor-binding domain comprises a VL comprising the amino acid sequence DVVMTQTPLSLPVSLGDQASISCRSSQSLVHSNGNTYLHWYLQKPGQSPNLLIY KVSNRFSGVPDRFSGSGSGTDFTLKISRVEAEDLGVYFCSQGTHVPYTFGGGTK LEIKRA (SEQ ID NO: 12). In some embodiments, the target receptor is TrkB and the target receptor-binding domain comprises a VH comprising the amino acid sequence QVQLQQSGAELVRPGASVTLSCKASGYTFTDYEMIHWVKQTPVHGLEWIGTIDP ETAGTAYNNQKFKGKAILTAGKSSSTAYMELRSLTSEDSAVYYCTGVTTWFAY WGQGTLVTVSA (SEQ ID NO: 13). In some embodiments, the target receptor is TrkB and the target receptor-binding domain comprises SEQ ID NO:12 and SEQ ID NO: 13.

In some embodiments, the target receptor is TrkB and the target receptor-binding domain comprises an analog of any one of SEQ ID NO: 10, SEQ ID NO: 11, SEQ ID NO: 12 and SEQ ID NO: 13. In some embodiments, the target receptor is TrkB and the target receptor-binding domain comprises a homolog of any one of SEQ ID NO: 10, SEQ ID NO: 11, SEQ ID NO: 12 and SEQ ID NO: 13. In some embodiments, the target receptor is TrkB and the target receptor-binding domain comprises an amino acid sequence with at least 70%, 75%, 80%, 85%, 90%, 95%, 97%, or 99% identity to any one of SEQ ID NO: 10, SEQ ID NO: 11, SEQ ID NO: 12 and SEQ ID NO: 13 and is capable of binding TrkB. Each possibility represents a separate embodiment of the invention.

The term "analog" as used herein, refers to a polypeptide that is similar, but not identical, to the polypeptide of the invention that still is capable of binding the target receptor. An analog, may have deletions or mutations that result in an amino acids sequence that is different than the amino acid sequence of the polypeptide of the invention. It should be understood, that all analogs of the polypeptide of the invention would still be capable of binding the target receptor. Further, an analog may be analogous to a fragment of the polypeptide of the invention, however, in such a case the fragment must comprise at least 50 consecutive amino acids of the polypeptide of the invention. In some embodiments, the analog or homolog is a human analog or homolog of the murine antibodies or antigen binding fragments described herein.

In some embodiments, the target receptor is TrkB and the chimeric transmembrane polypeptide comprises the amino acid sequence DVVMTQLPLSLPVILGDQASISCRSSQSLIHSNGNTYLHWYLQKPGQSPKLLIYK VSNRFSGVPDRFSGSGSGTDFTLKISRVEAEDLGVYFCSQSTHVPFTFGSGTKLEI KRAGGSSRSSSSGGGGSGGGGQVQLQQSGPELVKPGASVKLSCKASGYTFTSY DINWVKQRPGQGLEWIGWIYPRDGSIKFNEKFKGKATLTVDTSSSTAYMELHS LTSEDSAAYFCARRGRLLLYGFAYWGQGTLVTVSAXXEQKLISEEDLALSNSIM YFSHFVPVFLPAKPTTTPAPRPPTPAPTIASQPLSLRPEASRPAAGGAVHTRGLDL CYLLDGILFIYGVIITALYLRAKFSRSAETAANLQDPNQLFNELNLGRREEFDVL EKKRARDPEMGGKQQRRRNPQEGVFNALQKDKMAEAFSEIGTKGERRRGKGH DGLFQGLSTATKDTFDALHMQTLAPR (SEQ ID NO: 18) or DVVMTQTPLSLPVSLGDQASISCRSSQSLVHSNGNTYLHWYLQKPGQSPNLLIY KVSNRFSGVPDRFSGSGSGTDFTLKISRVEAE-
DLGVYFCSQGTHVPYTFGGGTK
LEIKRAGGSSRSSSSGGGGSGGGGQVQLQQSGAEL-
VRPGASVTLSCKASGYTFT DYEMHWVKQTPVH-
GLEWIGTIDPETAGTAYNNQKFKGKAILT-
AGKSSSTAYM
ELRSLTSEDSAVYYCTGVTTW-
FAYWGQGTLVTVSAXXALSNSIMYFSHFVPVF LPAK-
PTTTPAPRPPTPAPTIASQPLSLRPEASR-
PAAGGAVHTRGLDLCYLLDGILF
IYGVIITALYLRAKFSRSAETAANLQDPNQLFNELNL-
GRREEFDVLEKKRARDPE
MGGKQQRRRNPQEGVFNALQKDKMAEAFSEI-
GTKGERRRGKGHDGLFQGLST ATKDTFDALHMQTL-
APREGRGSLLTCGDVEENPGPMVSK-
GEELFTGVVPILVE
LDGDVNGHKFSVSGEGEGDATYGKLTLK-
FICTTGKLPVPWPTLVTTLTYGVQC
FSRYPDHMKQHDFFKSAMPEGYVQERTI-
FFKDDGNYKTRAEVKFEGDTLVNRI ELKGIDFKEDG-
NILGHKLEYNYNSHNVYIMAD-
KQKNGIKVNFKIRHNIEDGSVQ
LADHYQQNTPIGDGPVLLPDNHYLSTQSALSKDP-
NEKRDHMVLLEFVTAAGIT LGMDELYK (SEQ ID NO: 20).

In some embodiments, the target receptor is GLP1R and the target receptor-binding domain comprises a VL comprising the amino acid sequence QIVLTQ-SPAIIVISASPGEKVTMTCSASSRVTYMHWYQQRSGT-SPKRWIYDTSKL
ASGVPARFSGSGSGTSYSLTISSMEAE-
DAATYYCQQWGNNPQYTFGGGTRLEIK R (SEQ ID NO: 14). In some embodiments, the target receptor is GLP1R and the target receptor-binding domain comprises a VH comprising the amino acid sequence QVTL-KESGPGILQPSQTLSLTCSFSGFSLST-
SGTGVGWIRQPSGKGLEWLSHIWW DDVKRYN-
PALKSRLTISRDTSYSQVFLRIASVDTADTATYYCA-
RILDGTGPMDY WGQGTSVTVSS (SEQ ID NO: 15). In some embodiments, the target receptor is GLP1R and the target receptor-binding domain comprises SEQ ID NO:14 and SEQ ID NO: 15.

In some embodiments, the target receptor is GLP1R and the target receptor-binding domain comprises an analog of any one of SEQ ID NO: 14 and SEQ ID NO: 15. In some embodiments, the target receptor is GLP1R and the target receptor-binding domain comprises a homolog of any one of SEQ ID NO: 14 and SEQ ID NO: 15. In some embodiments, the target receptor is GLP1R and the target receptor-binding domain comprises an amino acid sequence with at least 70%, 75%, 80%, 85%, 90%, 95%, 97%, or 99% identity to any one of SEQ ID NO: 14 and SEQ ID NO: 15 and is capable of binding GLP1R. Each possibility represents a separate embodiment of the invention.

In some embodiments, the target receptor is GLP1R and the chimeric transmembrane polypeptide comprises the amino acid sequence IVLTQ-SPAIIVISASPGEKVTMTCSASSRVTYMHWYQQRSGT-SPKRWIYDTSKLAS GVPARFSGSGSGTSYSLTISSME-
AEDAATYYCQQWGNNPQYTFGGGTRLEIKR
GGGGSGGGGSGGGGSGGGGSQVTLKESGPGILQP-
SQTLSLTCSFSGFSLSTSGTG VGWIRQPSGKGLEW-
LSHIWWDDVKRYNPALKSRLTISRDTSYSQVFL-
RIASVDT
ADTATYY-
CARILDGTGPMDYWGQGTSVTVSSXXEQKLISEED-
LALSNSIMYFS HFVPVFLPAKPTTTPAPRPPTPAPTIA-
SQPLSLRPEASRPAAGGAVHTRGLDLCY
LLDGILFIYGVIITALYLRAKFSR-
SAETAANLQDPNQLFNELNLGRREEFDVLEK
KRARDPEMGGKQQRRRNPQEGVFNALQKDK-
MAEAFSEIGTKGERRRGKGHD GLFQGL-
STATKDTFDALHMQTLAPR (SEQ ID NO: 22).

In some embodiments, the target receptor is GHR and the target receptor-binding domain comprises a Growth Hormone (GH). In some embodiments, the GH is human GH (hGH). In some embodiments, hGh comprises the amino acid sequence EGSADYKDHDGDYKDHDI-
DYKDDDDKFPTIPLSRLFDNAMLRAHRLHQLAFD
TYQEFEEAYIPKEQKYSFLQNPQTSLCFSESIPTPSN-
REETQQKSNLELLRISLLLI
QSWLEPVQFLRSVFANSLVYGASDSN-
VYDLLKDLEEGIQTLMGRLEDGSPRTG QIFKQ-
TYSKFDTNSHNDDALLKNYGLLYCFRKDMDKVET-
FLRIVQCRSVEGSC GF (SEQ ID NO: 16). In some embodiments, the GH is a fragment, homolog, analog or derivative of hGH that is capable of binding GHR. In some embodiments, the GH comprises an amino acid sequence with at least 70%, 75%, 80%, 85%, 90%, 95%, 97%, or 99% identity to SEQ ID NO: 16.

The term "derivative" as used herein, refers to any polypeptide that is based off the polypeptide of the invention and is still capable of binding the target receptor. A derivative is not merely a fragment of the polypeptide, nor does it have amino acids replaced or removed (an analog), rather it may have additional modification made to the polypeptide, such as a post-translational modification. Further, a derivative may be a derivative of a fragment of the polypeptide of the invention, however, in such a case the fragment must comprise at least 50 consecutive amino acids of the polypeptide of the invention. In some embodiments, the chimeric transmembrane polypeptides of the invention are derivatives of the polypeptides described herein. In some embodiments, the derivatives comprise glycosylation of the polypeptide. One skilled in the art will appreciate that glycosylation of the polypeptide may be necessary for robust surface expression.

In some embodiments, the target receptor is GHR and the chimeric transmembrane polypeptide comprises the amino acid sequence EGSADYKDHDGDYKDHDI-
DYKDDDDKFPTIPLSRLFDNAMLRAHRLHQLAFD
TYQEFEEAYIPKEQKYSFLQNPQTSLCFSESIPTPSN-
REETQQKSNLELLRISLLLI
QSWLEPVQFLRSVFANSLVYGASDSN-
VYDLLKDLEEGIQTLMGRLEDGSPRTG QIFKQ-
TYSKFDTNSHNDDALLKNYGLLYCFRKDMDKVET-
FLRIVQCRSVEGSC
GFXXEQKLISEEDLALSNSIMYFSHFVPVFLPAK-
PTTTPAPRPPTPAPTIASQPLSL RPEASR-
PAAGGAVHTRGLDLCYLLDGILFIYGVIITALYL-
RAKFSRSAETAANLQ
DPNQLFNELNLGRREEFDVLEKK-
RARDPEMGGKQQRRRNPQEGVFNALQKDK
MAEAFSEIGTKGERRRGKGHDGLFQGL-
STATKDTFDALHMQTLAPR (SEQ ID NO: 24).

In some embodiments, the target receptor is PD-1 and the target receptor-binding domain comprises a VL comprising the amino acid sequence EIVLTQSPATLSLSPGER-
ATLSCRASKGVSTSGY-
SYLHWYQQKPGQAPRLLIYLA
SYLESGVPARFSGSGSGTDFTLTISSLEPED-
FAVYYCQHSRDLPLTFGGGTKVEI
KRTVAAPSVFIFPPSDEQLKSGTASVVCLLNNFY-
PREAKVQWKVDNALQSGNS QESVTEQDSKDSTYS-
LSSTLTLSKADYEKHKVYACE-
VTHQGLSSPVTKSFNRGE C (SEQ ID NO: 25). In some embodiments, the target receptor is PD-1 and the target receptor-binding domain comprises a VH comprising the amino acid sequence QVQLVQSGVEVKKP-GASVKVSCKASGYTFTNYYMYWVRQAPGQ-GLEWMGGI NPSNGGTNFNEKFKNRVTLTTDSSTT-TAYMELKSLQFDDTAVYYCARRDYRFD MGFDYWGQGTTVTVSSASTKGPSVFPLAPCSRSTS-ESTAALGCLVKDYFPEPVT VSWNSGALT-SGVHTFPAVLQSSGLYS-LSSVVTVPSSSLGTKTYTCNVDHKPSNT KVDKRVESKYGPPCPPCPAPE-FLGGPSVFLEPPKPKDTLMISRTPEVTCVVVDVS QEDPEVQFNWYVDGVEVHNAKTKPREEQFN-STYRVVSVLTVLHQDWLNGKE YKCKVSNKGLPSSIEKTISKAKGQPREPQVYTLPP-SQEEMTKNQVSLTCLVKGF YPSDIAVEWESNGQPEN-NYKTTPPVLDSDGSFFLYSRLTVDKSRWQEGNVFSCS VMHEALHNHYTQKSLSLSLGK (SEQ ID NO: 26). In some embodiments, the target receptor is PD-1 and the target receptor-binding domain comprises SEQ ID NO:25 and SEQ ID NO: 26.

In some embodiments, the target receptor is PD-1 and the target receptor-binding domain comprises an analog of any one of SEQ ID NO: 25 and SEQ ID NO: 26. In some embodiments, the target receptor is PD-1 and the target receptor-binding domain comprises a homolog of any one of SEQ ID NO: 25 and SEQ ID NO: 26. In some embodiments, the target receptor is PD-1 and the target receptor-binding domain comprises an amino acid sequence with at least 70%, 75%, 80%, 85%, 90%, 95%, 97%, or 99% identity to any one of SEQ ID NO: 25 and SEQ ID NO: 26 and is capable of binding PD-1. Each possibility represents a separate embodiment of the invention.

In some embodiments, the target receptor is PD-1 and the chimeric transmembrane polypeptide comprises the amino acid sequence QVQLVQSGVEVKKPGASVKVSCK-ASGYTFTNYYMYWVRQAPGQGLEWMGGI NPSNGGTNFNEKFKNRVTLTTDSSTT-TAYMELKSLQFDDTAVYYCARRDYRFD MGFDYWGQGTTVTVSSASTKGPSVFPLAPCSRSTS-ESTAALGCLVKDYFPEPVT VSWNSGALT-SGVHTFPAVLQSSGLYS-LSSVVTVPSSSLGTKTYTCNVDHKPSNT KVDKRVESKYGPPCPPCPAPE-FLGGPSVFLFPPKPKDTLMISRTPEVTCVVVDVS QEDPEVQFNWYVDGVEVHNAKTKPREEQFN-STYRVVSVLTVLHQDWLNGKE YKCKVSNKGLPSSIEKTISKAKGQPREPQVYTLPP-SQEEMTKNQVSLTCLVKGF YPSDIAVEWESNGQPEN-NYKTTPPVLDSDGSFFLYSRLTVDKSRWQEGNVFSCS VMHEALHN-HYTQKSLSLSLGKGGSSRSSSSGGGGSGGGGEIV-LTQSPATLSLSP GERATLSCRASKGVSTSGY-SYLHWYQQKPGQAPRLLIYLASYLESGVPARFSGS GSGTDFTLTISSLEPED-FAVYYCQHSRDLPLTFGGGTKVEIKRTVAAPSVFIFPPS DEQLKSGTASVVCLLNNFYPREAKVQWKVD-NALQSGNSQESVTEQDSKDSTY SLSSTLTL-SKADYEKHKVYACE-VTHQGLSSPVTKSFNRGECXXEQKLISEEDLA LSNSIMYFSHFVPVFLPAKPTTTPAPRPPTPAPTIA-SQPLSLRPEASRPAAGGAVH TRGLDLCYLLDGIL-FIYGVIITALYLRAKFSR-SAETAANLQDPNQLFNELNLGRR EEFDVLEKK-RARDPEMGGKQQRRRNPQEGVFNALQKDKMAEAF-SEIGTKGER RRGKGHDGLFQGL-STATKDTFDALHMQTLAPR (SEQ ID NO: 28).

The XX in all of the sequence may be any two amino acids, or no amino acids, as these amino acids are a result of a restriction enzyme site in the coding sequence of the chimeric protein and have no functional role. In some embodiments, the XX is valine-aspartic acid.

In some embodiments, the chimeric transmembrane polypeptides of the invention further comprise a leader peptide at their N-terminus. In some embodiments, the leader peptide comprises or consists of the sequence MDMRVPAQLLGLLLLWLSGARCQ (SEQ ID NO: 2).

In some embodiments, the chimeric transmembrane polypeptide has at least 70%, 75%, 80%, 85%, 90%, 95%, 97%, or 99% homology or identity to an amino acid sequence of any one of SEQ ID NOs: 18, 20, 22, 24 or 28 and is not capable of transducing an immune cell activating signal. Each possibility represents a separate embodiment of the invention. In some embodiments, the chimeric transmembrane polypeptide is a derivative or analog of any one of SEQ ID NOs: 18, 20, 22, 24 or 28. Each possibility represents a separate embodiment of the invention.

Pharmaceutical Compositions

By another aspect, there is provided a pharmaceutical composition comprising any of the modified cells of the invention and a pharmaceutically acceptable carrier, excipient, or adjuvant. In some embodiments, the pharmaceutical composition comprises a therapeutically effective amount of the modified cells of the invention.

As used herein, the term "carrier," "adjuvant" or "excipient" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

The term "therapeutically effective amount" refers to a number of cells effective to treat a disease or disorder in a mammal. The term "a therapeutically effective amount" refers to an amount effective, at dosages and for periods of time necessary, to achieve the desired therapeutic or prophylactic result. The exact dosage form and regimen would be determined by the physician according to the patient's condition.

In some embodiments, the pharmaceutical composition comprises at least 1 million, 2 million, 3 million, 5 million, 10 million, 50 million or 100 million immune cells. Each possibility represents a separate embodiment of the invention.

Methods of Treatment

In some embodiments, the providing comprises extracting a primary cell from the subject. In some embodiments, extracting a primary cell from a subject comprises drawing a blood or serum sample. In some embodiments, extracting a primary cell from a subject comprises drawing a lymph sample. In some embodiments, a primary cell is isolation using a kit. Such kits are common in the art and include, but are not limited to, Miltenyi cell isolation and cell separation kits, CD4+ magnetic bead kits, CD8+ magnetic bead kits, and the like. In some embodiments, the primary cell is isolated using an antibody conjugated column. In some embodiments, a primary cell is isolated using FACS sorting. Any suitable FACS antibody that identifies are target cell may be used for the cell sorting.

Expression of heterologous proteins in a target cell is well known in the art. Any method whereby the chimeric transmembrane proteins of the invention are expressed in the cell may be used to perform the methods of the invention.

The term "expression" as used herein refers to the biosynthesis of a protein including translation of said gene product. Thus, expression of a protein may refer to transcription of the nucleic acid fragment (e.g., transcription resulting in mRNA or other functional RNA) and/or translation of RNA into a precursor or mature protein (polypeptide). In some embodiments, expression is expression on the cell surface. In some embodiments, expression is expression of a precursor protein comprising a leader peptide, cleavage of that peptide and surface expression of the mature protein.

Expressing of a heterologous transcript within a cell is well known to one skilled in the art. It can be carried out by, among many methods, transfection, viral infection, or direct alteration of the cell's genome. In some embodiments, the heterologous transcript is in an expression vector such as plasmid or viral vector.

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the heterologous transcript is operably linked to a promoter. The term "operably linked" is intended to mean that the nucleotide sequence of interest is linked to the regulatory element or elements in a manner that allows for expression of the nucleotide sequence (e.g. in an in vitro transcription/translation system or in a host cell when the vector is introduced into the host cell).

In some embodiments, the vector is introduced into the cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like.

The term "promoter" as used herein refers to a group of transcriptional control modules that are clustered around the initiation site for an RNA polymerase i.e., RNA polymerase II. Promoters are composed of discrete functional modules, each consisting of approximately 7-20 bp of DNA, and containing one or more recognition sites for transcriptional activator or repressor proteins.

In some embodiments, nucleic acid sequences are transcribed by RNA polymerase II (RNAP II and Pol II). RNAP II is an enzyme found in eukaryotic cells. It catalyzes the transcription of DNA to synthesize precursors of mRNA and most snRNA and microRNA.

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

It will be appreciated that other than containing the necessary elements for the transcription and translation of the inserted coding sequence (encoding the chimeric transmembrane polypeptide), the expression construct of the present invention can also include sequences engineered to optimize stability, production, purification, yield or activity of the expressed polypeptide.

By another aspect, there is provided an artificial expression vector that encodes a chimeric transmembrane protein of the invention.

As used herein, the terms "administering," "administration," and like terms refer to any method which, in sound medical practice, delivers a composition containing an active agent to a subject in such a manner as to provide a therapeutic effect. Other suitable routes of administration can include parenteral, subcutaneous, intravenous, intramuscular, intracranial, intracerebroventricular, intrathecal, or intraperitoneal. It will be understood by one skilled in the art that due to the homing capabilities of immune cells systemic administration is sufficient for treatment of even local aliments. In some embodiments, administration is performed directly to the site of disease. Non-limiting examples of such are intracranial administration for a brain disease, topical administration for a skin disease, and intramuscular administration for a muscle disease.

The dosage administered will be dependent upon the age, health, and weight of the recipient, kind of concurrent treatment, if any, frequency of treatment, and the nature of the effect desired.

In some embodiments, the modified cell is administered to the subject. In some embodiments, a therapeutically effective amount of modified cells is administered to the subject. In some embodiments, a pharmaceutical composition comprising a therapeutically effective amount of modified cells is administered to the subject.

In some embodiments, the methods of the invention may be used to treat any disease, disorder or condition for which a target molecule is known to be associated and wherein activation or inhibition of that molecule is known to have a positive effect on the disease, disorder or condition. In some embodiments, a positive effect is any improvement in a symptom of that disease, disorder or condition. In some embodiments, a positive effect is any reduction in the severity, or longevity of a symptom. In some embodiments, a positive effect is any improvement in the quality of life of the subject.

In some embodiments, the target receptor is TrkB and the disease or disorder is a neurological disease or disorder. In some embodiments, the neurological disease or disorder is selected from: Alzheimer's disease, depression, memory loss, amyotrophic lateral sclerosis (ALS), epilepsy and brain cancer. In some embodiments, the neurological disease or disorder is a Brain-Derived Neurotrophic Factor (BDNF)-associated disease or disorder. In some embodiments, the target receptor-binding domain comprises an anti-TrkB antigen binding domain. In some embodiments, the TrkB antigen binding domain is from a commercially available anti-TrkB antibody.

In some embodiments, the target receptor is GLP1R and the disease or disorder is a metabolic or cardiovascular disease or disorder. In some embodiments, a metabolic disease or disorder is selected from: diabetes, obesity, glycogen storage disease, Parkinson's disease and mitochondrial myopathy. In some embodiments, a metabolic disease or disorder is a mitochondrial disease or disorder. In some embodiments, the metabolic disease is a disease of glucose homeostasis. In some embodiments, the cardiovascular disease or disorder is selected from: stroke, myocardial infarction, cardiac ischemia, and coronary artery disease. In some embodiments, the target receptor-binding domain comprises an anti-GLP1R antigen binding domain. In some embodiments, the GLP1R antigen binding domain is from a commercially available anti-GLP1R antibody.

In some embodiments, the target receptor is GHR and the disease or disorder is a growth disease or disorder. In some embodiments, the growth disease or disorder is selected from: acromegaly, growth hormone deficiency, cancer, Turner syndrome, and Prader-Willi syndrome. In some embodiments, the growth disease or disorder is any disease or disorder which can be treated with administration of hGH. In some embodiments, the disease which can be treated with hGH is a muscle disease. In some embodiments, the muscle disease is selected from a muscle wasting disease and a muscular dystrophy. In some embodiments, the muscle wasting disease is selected from multiple sclerosis, cachexia and sarcopenia. In some embodiments, the muscular dystrophy is selected from Deschene's muscular dystrophy, Becker muscular dystrophy, myotonic dystrophy, and facioscapulohumeral muscular dystrophy. In some embodiments, the target receptor-binding domain comprises a GH. In some embodiments, the GH is hGH.

In some embodiments, the target receptor is PD-1 and the disease or disorder is an immune disease or disorder or cancer. In some embodiments, the immune disease or disorder is selected from: lupus, rheumatoid arthritis, psoriasis, Graves' disease, immune-mediated inflammation, and celiac disease. In some embodiments, the disease or disorder is cancer and the target receptor-binding domain comprises a PD-1 antagonist. In some embodiments, the target receptor-binding domain comprises an anti-PD-1 antigen binding domain. In some embodiments, the PD-1 antigen binding domain is from a commercially available anti-PD-1 antibody.

Non-limiting examples for GLP1-R agonist antibodies that can be used as a source for GLP1-R variable heavy and light chains are described in US patent application numbers: 2014/0911910, 2014/0775074, 2013/0650469, 20150965841, 2009/0392244, 2007/0374569 and U.S. Pat. Nos. 9,358,287; 8,501,693 and 9,328,154 incorporated herein by reference.

Non-limiting examples for TrkB agonist antibodies that can be used as a source for TrkB variable heavy and light chains are described in US patent application numbers: 2007/0516187, 2008/0682505, 2010/0697983 and U.S. Pat. Nos. 7,459,156; 7,750,122; 8,642,035; 9,028,820 incorporated herein by reference.

Non-limiting examples for PD-1 or PD-L1 agonist antibodies that can be used as a source for variable heavy and light chains are described in U.S. Pat. Nos. 7,427,665; 7,722,868; 7,595,048; 7,488,802; 8,008,449; 7,943,743; 9,181,342 and 8,617,546 incorporated herein by reference.

Non-limiting examples for CTLA4 agonist antibodies that can be used as a source for CTLA4 variable heavy and light chains are described in U.S. Pat. Nos. 7,592,007; 7,109,003; 7,034,121; 7,605,238; 7,452,535 incorporated herein by reference.

In some embodiments, the methods of the invention further comprise partially activating the modified cell. In some embodiments, partial activation comprises homing ability and/or the ability to synapse with the target cell. In some embodiments, partial activation does not comprise effector function activation and/or activation of cytotoxicity.

In some embodiments, the methods of the invention further comprise determining modulation of signaling in the target cell. In some embodiments, the methods of the invention further comprise determining modulation of the target receptor. In some embodiments, the methods of the invention further comprise determining the modified cell is not cytotoxic. In some embodiments, the methods of the invention further comprise determining the modified immune cell is not activated.

In some embodiments, the determining comprises determining phosphorylation of at least one signaling protein. In some embodiments, the determining comprises determining phosphorylation of a residue within a signaling domain of the target receptor. In some embodiments, the determining comprises determining phosphorylation of a residue within a signaling domain of a protein of a signaling cascade. In some embodiments, the phosphorylated residue is a tyrosine residue. In some embodiments, the determining comprises determining upregulation of a level of a downstream target of the target receptor. In some embodiments, the determining comprises determining down-regulation of a level of a downstream target of the target receptor.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Cloning of Chimeric Transmembrane Proteins and Retroviral Transduction of BW5147 Cells Chimeric transmembrane (TM) protein sequences include leader peptide-VL-linker-VH-hinge-TM cytoplasmic part-GFP (TrkB-GFP-WT) and VL-linker-VH-hinge-mutated TM cytoplasmic part-GFP (TrkB-GFP-Mut) and VL-linker-VH-Myc-hinge-TM cytoplasmic part (TrkB-Myc-WT) and VL-linker-VH-Myc-hinge-mutated TM cytoplasmic part (TrkB-Myc-Mut) were synthesized for anti-TrkB. Two chimeric transmembrane protein sequences include leader peptide-VL-linker-VH-MYC+hinge-TM-cytoplasmic part were synthesized for GLP1R and PD-1.

The WT murine zeta TM-cytoplasmic sequence used is LCYLLDGILFIYGVIITALYLRAKFSR-SAETAANLQDPNQLYNELNLGRREEYDV LEKKRARDPEMGGKQQRRRNPQEGVYNALQKDKMAEAYSEIGTKGERRRGK GHDGLYQGLSTATKDTYDALHMQTLAPR (SEQ ID NO: 8). The mutant zeta TM-cytoplasmic sequence used is LCYLLDGILFIYGVIITALYLRAKFSR-SAETAANLQDPNQLFNELNLGRREEFDV LEKKRARDPEMGGKQQRRRNPQEGVFNALQKDKMAEAFSEIGTKGERRRGKG HDGLFQGLSTATKDTFDALHMQTLAPR (SEQ ID NO: 9).

The 8 sequences generated were the following, with an N-terminal leader peptide of MDMRVPAQLLGLLLLWLSGARCQ (SEQ ID NO: 2):

TrkB-Myc-WT:
(SEQ ID NO: 17)
DVVMTQLPLSLPVILGDQASISCRSSQSLIHSNGNTYLHWYLQKPGQS
PKLLIYKVSNRFSGVPDRFSGSGSGTDFTLKISRVEAEDLGVYFCSQS
THVPFTFGSGTKLEIKRAGGSSRSSSSGGGGSGGGGQVQLQQSGPELV
KPGASVKLSCKASGYTFTSYDINWVKQRPGQGLEWIGWIYPRDGSIKF
NEKFKGKATLTVDTSSSTAYMELHSLTSEDSAAYFCARRGRLLLYGFA
YWGQGTLVTVSAXXEQKLISEEDLALSNSIMYFSHFVPVFLPAKPTTT
PAPRPPTPAPTIASQPLSLRPEASRPAAGGAVHTRGLDLCYLLDGILF
IYGVIITALYLRAKFSRSAETAANLQDPNQLYNELNLGRREEYDVLEK
KRARDPEMGGKQQRRRNPQEGVYNALQKDKMAEAYSEIGTKGERRRGK
GHDGLYQGLSTATKDTYDALHMQTLAPR.

TrkB-Myc-Mut:
(SEQ ID NO: 18)
DVVMTQLPLSLPVILGDQASISCRSSQSLIHSNGNTYLHWYLQKPGQS
PKLLIYKVSNRFSGVPDRFSGSGSGTDFTLKISRVEAEDLGVYFCSQS
THVPFTFGSGTKLEIKRAGGSSRSSSSGGGGSGGGGQVQLQQSGPELV
KPGASVKLSCKASGYTFTSYDINWVKQRPGQGLEWIGWIYPRDGSIKF
NEKFKGKATLTVDTSSSTAYMELHSLTSEDSAAYFCARRGRLLLYGFA
YWGQGTLVTVSAXXEQKLISEEDLALSNSIMYFSHFVPVFLPAKPTTT
PAPRPPTPAPTIASQPLSLRPEASRPAAGGAVHTRGLDLCYLLDGILF
IYGVIITALYLRAKFSRSAETAANLQDPNQLFNELNLGRREEFDVLEK
KRARDPEMGGKQQRRRNPQEGVFNALQKDKMAEAFSEIGTKGERRRGK
GHDGLFQGLSTATKDTFDALHMQTLAPR.

TrkB-GFP-WT:
(SEQ ID NO: 19)
DVVMTQTPLSLPVSLGDQASISCRSSQSLVHSNGNTYLHWYLQKPGQS
PNLLIYKVSNRFSGVPDRFSGSGSGTDFTLKISRVEAEDLGVYFCSQG
THVPYTFGGGTKLEIKRAGGSSRSSSSGGGGSGGGGQVQLQQSGAELV
RPGASVTLSCKASGYTFTDYEMHWVKQTPVHGLEWIGTIDPETAGTAY
NNQKFKGKAILTAGKSSSTAYMELRSLTSEDSAVYYCTGVTTWFAYWG
QGTLVTVSAXXALSNSIMYFSHFVPVFLPAKPTTTPAPRPPTPAPTIA
SQPLSLRPEASRPAAGGAVHTRGLDLCYLLDGILFIYGVIITALYLRA
KFSRSAETAANLQDPNQLYNELNLGRREEYDVLEKKRARDPEMGGKQQ
RRRNPQEGVYNALQKDKMAEAYSEIGTKGERRRGKGHDGLYQGLSTAT
KDTYDALHMQTLAPREGRGSLLTCGDVEENPGPMVSKGEELFTGVVPI
LVELDGDVNGHKFSVSGEGEGDATYGKLTLKFICTTGKLPVPWPTLVT
TLTYGVQCFSRYPDHMKQHDFFKSAMPEGYVQERTIFFKDDGNYKTRA
EVKFEGDTLVNRIELKGIDFKEDGNILGHKLEYNYNSHNVYIMADKQK
NGIKVNFKIRHNIEDGSVQLADHYQQNTPIGDGPVLLPDNHYLSTQSA
LSKDPNEKRDHMVLLEFVTAAGITLGMDELYK.

TrkB-GFP-Mut:
(SEQ ID NO: 20)
DVVMTQTPLSLPVSLGDQASISCRSSQSLVHSNGNTYLHWYLQKPGQS
PNLLIYKVSNRFSGVPDRFSGSGSGTDFTLKISRVEAEDLGVYFCSQG
THVPYTFGGGTKLEIKRAGGSSRSSSSGGGGSGGGGQVQLQQSGAELV
RPGASVTLSCKASGYTFTDYEMHWVKQTPVHGLEWIGTIDPETAGTAY
NNQKFKGKAILTAGKSSSTAYMELRSLTSEDSAVYYCTGVTTWFAYWG
QGTLVTVSAXXALSNSIMYFSHFVPVFLPAKPTTTPAPRPPTPAPTIA
SQPLSLRPEASRPAAGGAVHTRGLDLCYLLDGILFIYGVIITALYLRA
KFSRSAETAANLQDPNQLFNELNLGRREEFDVLEKKRARDPEMGGKQQ
RRRNPQEGVFNALQKDKMAEAFSEIGTKGERRRGKGHDGLFQGLSTAT
KDTFDALHMQTLAPREGRGSLLTCGDVEENPGPMVSKGEELFTGVVPI
LVELDGDVNGHKFSVSGEGEGDATYGKLTLKFICTTGKLPVPWPTLVT
TLTYGVQCFSRYPDHMKQHDFFKSAMPEGYVQERTIFFKDDGNYKTRA
EVKFEGDTLVNRIELKGIDFKEDGNILGHKLEYNYNSHNVYIMADKQK
NGIKVNFKIRHNIEDGSVQLADHYQQNTPIGDGPVLLPDNHYLSTQSA
LSKDPNEKRDHMVLLEFVTAAGITLGMDELYK.

GLP1R-Myc-WT:
(SEQ ID NO: 21)
IVLTQSPAIMSASPGEKVTMTCSASSRVTYMHWYQQRSGTSPKRWIYD
TSKLASGVPARFSGSGSGTSYSLTISSMEAEDAATYYCQQWGNNPQYT

-continued

FGGGTRLEIKRGGGGSGGGGSGGGGSGGGGSQVTLKESGPGILQPSQT
LSLTCSFSGFSLSTSGTGVGWIRQPSGKGLEWLSHIWWDDVKRYNPAL
KSRLTISRDTSYSQVFLRIASVDTADTATYYCARILDGTGPMDYWGQG
TSVTVSSXXEQKLISEEDLALSNSIMYFSHFVPVFLPAKPTTTPAPRP
PTPAPTIASQPLSLRPEASRPAAGGAVHTRGLDLCYLLDGILFIYGVI
ITALYLRAKFSRSAETAANLQDPNQLYNELNLGRREEYDVLEKKRARD
PEMGGKQQRRRNPQEGVYNALQKDKMAEAYSEIGTKGERRRGKGHDGL
YQGLSTATKDTYDALHMQTLAPR.

GLP1R-Myc-Mut:
(SEQ ID NO: 22)
IVLTQSPAIMSASPGEKVTMTCSASSRVTYMHWYQQRSGTSPKRWIYD
TSKLASGVPARFSGSGSGTSYSLTISSMEAEDAATYYCQQWGNNPQYT
FGGGTRLEIKRGGGGSGGGGSGGGGSGGGGSQVTLKESGPGILQPSQT
LSLTCSFSGFSLSTSGTGVGWIRQPSGKGLEWLSHIWWDDVKRYNPAL
KSRLTISRDTSYSQVFLRIASVDTADTATYYCARILDGTGPMDYWGQG
TSVTVSSXXEQKLISEEDLALSNSIMYFSHFVPVFLPAKPTTTPAPRP
PTPAPTIASQPLSLRPEASRPAAGGAVHTRGLDLCYLLDGILFIYGVI
ITALYLRAKFSRSAETAANLQDPNQLFNELNLGRREEFDVLEKKRARD
PEMGGKQQRRRNPQEGVFNALQKDKMAEAFSEIGTKGERRRGKGHDGL
FQGLSTATKDTFDALHMQTLAPR.

PD-1-Myc-WT:
(SEQ ID NO: 27)
QVQLVQSGVEVKKPGASVKVSCKASGYTFTNYYMYWVRQAPGQGLEWM
GGINPSNGGTNFNEKFKNRVTLTTDSSTTTAYMELKSLQFDDTAVYYC
ARRDYRFDMGFDYWGQGTTVTVSSASTKGPSVFPLAPCSRSTSESTAA
LGCLVKDYFPEPVTVSWNSGALTSGVHTFPAVLQSSGLYSLSSVVTVP
SSSLGTKTYTCNVDHKPSNTKVDKRVESKYGPPCPPCPAPEFLGGPSV
FLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTI
SKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEAL
HNHYTQKSLSLSLGKGGSSRSSSSGGGGSGGGGEIVLTQSPATLSLSP
GERATLSCRASKGVSTSGYSYLHWYQQKPGQAPRLLIYLASYLESGVP
ARFSGSGSGTDFTLTISSLEPEDFAVYYCQHSRDLPLTFGGGTKVEIK
RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSS
PVTKSENRGECXXEQKLISEEDLALSNSIMYFSHEVPVFLPAKPTTTP
APRPPTPAPTIASQPLSLRPEASRPAAGGAVHTRGLDLCYLLDGILFI
YGVIITALYLRAKFSRSAETAANLQDPNQLYNELNLGRREEYDVLEKK
RARDPEMGGKQQRRRNPQEGVYNALQKDKMAEAYSEIGTKGERRRGKG
HDGLYQGLSTATKDTYDALHMQTLAPR

PD-1-Myc-Mut:
(SEQ ID NO: 28)
QVQLVQSGVEVKKPGASVKVSCKASGYTFTNYYMYWVRQAPGQGLEWM
GGINPSNGGTNFNEKFKNRVTLTTDSSTTTAYMELKSLQFDDTAVYYC
ARRDYRFDMGFDYWGQGTTVTVSSASTKGPSVFPLAPCSRSTSESTAA
LGCLVKDYFPEPVTVSWNSGALTSGVHTFPAVLQSSGLYSLSSVVTVP
SSSLGTKTYTCNVDHKPSNTKVDKRVESKYGPPCPPCPAPEFLGGPSV
FLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTI
SKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEAL
HNHYTQKSLSLSLGKGGSSRSSSSGGGGSGGGGEIVLTQSPATLSLSP
GERATLSCRASKGVSTSGYSYLHWYQQKPGQAPRLLIYLASYLESGVP
ARFSGSGSGTDFTLTISSLEPEDFAVYYCQHSRDLPLTFGGGTKVEIK
RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSS
PVTKSENRGECXXEQKLISEEDLALSNSIMYFSHEVPVFLPAKPTTTP
APRPPTPAPTIASQPLSLRPEASRPAAGGAVHTRGLDLCYLLDGILFI
YGVIITALYLRAKFSRSAETAANLQDPNQLFNELNLGRREEFDVLEKK
RARDPEMGGKQQRRRNPQEGVFNALQKDKMAEAFSEIGTKGERRRGKG
HDGLFQGLSTATKDTFDALHMQTLAPR.

Two more sequences were generated as above, with hGH amino acid sequence used in place of the VL and VH. The endogenous hGH leader peptide MATGSRTSLL-LAFGLLCLPWLQ (SEQ ID NO: 34) was used.

GHR-Myc-WT:
(SEQ ID NO: 23)
EGSADYKDHDGDYKDHDIDYKDDDDKFPTIPLSRLFDNAMLRAHRLHQ
LAFDTYQEFEEAYIPKEQKYSFLQNPQTSLCFSESIPTPSNREETQQK
SNLELLRISLLLIQSWLEPVQFLRSVFANSLVYGASDSNVYDLLKDLE
EGIQTLMGRLEDGSPRTGQIFKQTYSKFDTNSHNDDALLKNYGLLYCF
RKDMDKVETFLRIVQCRSVEGSCGFXXEQKLISEEDLALSNSIMYFSH
FVPVFLPAKPTTTPAPRPPTPAPTIASQPLSLRPEASRPAAGGAVHTR
GLDLCYLLDGILFIYGVIITALYLRAKFSRSAETAANLQDPNQLYNEL
NLGRREEYDVLEKKRARDPEMGGKQQRRRNPQEGVYNALQKDKMAEAY
SEIGTKGERRRGKGHDGLYQGLSTATKDTYDALHMQTLAPR.

GHR-Myc-MuT:
EGSADYKDHDGDYKDHDIDYKDDDDKFPTI-
PLSRLFDNAMLRAHRLHQLAFD TYQEFEEAY-
IPKEQKYSFLQNPQTSLCFSESIPTPSNREETQQKSN-
LELLRISLLLI
QSWLEPVQFLRSVFANSLVYGASDSN-
VYDLLKDLEEGIQTLMGRLEDGSPRTG QIFKQ-
TYSKFDTNSHNDDALLKNYGLLYCFRKDMDKVET-
FLRIVQCRSVEGSC
GFXXEQKLISEEDLALSNSIMYFSHFVPVFLPAK-
PTTTPAPRPPTPAPTIASQPLSL RPEASR-
PAAGGAVHTRGLDLCYLLDGILFIYGVIITALYL-
RAKFSRSAETAANLQ
DPNQLFNELNLGRREEFDVLEKK-

RARDPEMGGKQQRRRNPQEGVFNALQKDK
MAEAFSEIGTKGERRRGKGHDGLFQGL-
STATKDTFDALHMQTLAPR (SEQ ID NO: 24). In all of the above described sequences the XX maybe any amino acids or no amino acids. The XX result from a restriction enzyme site in the nucleic acid sequence that codes for the protein. In the actual proteins used the XX was valine-aspartic acid.

All 10 sequences were cloned into the retroviral vector pMP71-G-PRE. Plasmids were amplified using DH5alpha (Invitrogen) and purified with a Maxiprep Plasmid DNA Kit (Invitrogen). The packaging cell line Platinum-E (Cellbiolabs) was transfected in a 10 cm plate with 20 μg of plasmid DNA and 60 μL of PolyJet™ (SignaGen). After 16 hours, the medium was replaced to 10 ml of RPMI complete media. After 24 and 48 hours, the retrovirus supernatant was collected and filtered through a 0.45-μl m filter. BW5147 cells (1×10$^6$ cells/mL) were plated with virus supernatant and were spinoculated on RetroNectin-coated plates (12.5 μg/mL; TaKaRa, Clonthech) at 1500 g for 90 minutes at 32° C. with 4 μg/mL protamine sulfate (Sigma-Aldrich).

Cloning of TrkB-T2A and Retroviral Infection of RAW5147, 3T3 and HEK293 Cells.

Mouse TrkB cDNA (Sino Biological) was cloned in the pMP71-PRE expression vector with T2A-GFP. The packaging cell line Platinum-E (Cellbiolabs) was transfected in a 10 cm plate with 20 μg of plasmid DNA and 60 μL of PolyJet™ (SignaGen). After 16 hours, the medium was replaced to 10 ml of DMEM complete media. After 24 and 48 hours, the retrovirus supernatant was collected and filtered through a 0.45-μl m filter. Briefly, human embryonic kidney cells (HEK293T) cells, RAW 5147 and 3T3 cells were seeded in 24 well plates (NUNC). Next day cells were incubated with viral supernatant with 4 μg/mL protamine sulfate (Sigma-Aldrich). Transduced T cells were stained and analyzed 48-72 hours after sorting (FACS Aria cell sorter (BD biosciences, San Jose, CA, USA)

In Vitro Study of the Interaction Between TrkB Receptor and Chimeric-TrkB Antibody In cell-based binding assays, Raw264.7 cells expressing TrkB receptor were seeded on 12 well plates (Nunc) in DMEM based media (10% FBS, PSN). After reaching 85-95% confluency, cells were twice washed and DMEM media with 0.2% FBS was added for 4 hours. Then cells were washed and incubated during 1 h with DMEM without FBS before addition of neurotrophins or BW5147 cells. After that TrkB-expressing Raw 264.7 cells were incubated with BDNF (50 ng/ml) and BW5147 cells with chimeric receptors for 30 min and 1 h., Co-cultured cells were harvested and processed for Western blot analysis.

Western Blot Analysis

Cells were lysed in RIPA buffer (50 mM Tris-Cl, pH 8.0, 150 mM NaCl, 1% Triton, 0.5% sodium dodecyl sulphate) containing protease inhibitors (Sigma) and phosphatase inhibitors (Sigma). 30-50 μg of lysate was separated on 12% Tris-Glycine SDS-PAGE gels and then transferred to PVDF or nitrocellulose membranes. Membranes were incubated with antibodies against pTrkB (Tyr706/707), total TrkB (TrkB (80E3) from Cell Signaling and actin. WesternBright Quantum (Advansta) was used for visualization of the signal. The images were captured using a bioimaging analyzer (Fusion-FX; Vilber, France) and analyzed using ImageJ program. Quantification of the Western blots of phosphorylated TrkB. The integrated density value of the bands in Western blots was determined using densitometry (ImageJ), and data was normalized to actin and to total TrkB.

Cytokine ELISA

Raw264.7 cells expressing TrkB receptor and Raw264.7 cells were seeded on 96 well plates (Nunc) in DMEM based media (10% FBS, PSN). After reaching 85-95% confluency, cells were twice washed and 100 ul of DMEM media with 0.2% FBS was added for 4 hours. After 4 hours BW5147 cells in were added to the wells in 100 ul of DMEM media without FBS for ON. Supernatants were collected after 16 hours and analyzed for IL-2 with a sandwich ELISA (BioLegend), according to the manufacturer's instructions. Samples were analyzed with triplicates.

Statistical Analyses

All statistical analyses were performed with GraphPad Prism version 5.02 for Windows (GraphPad Software, San Diego, CA). All variables are expressed as means 6 SEM or SD, as indicated in figure legends. The p-values were calculated with one-way Anova test.

Figure 1B:
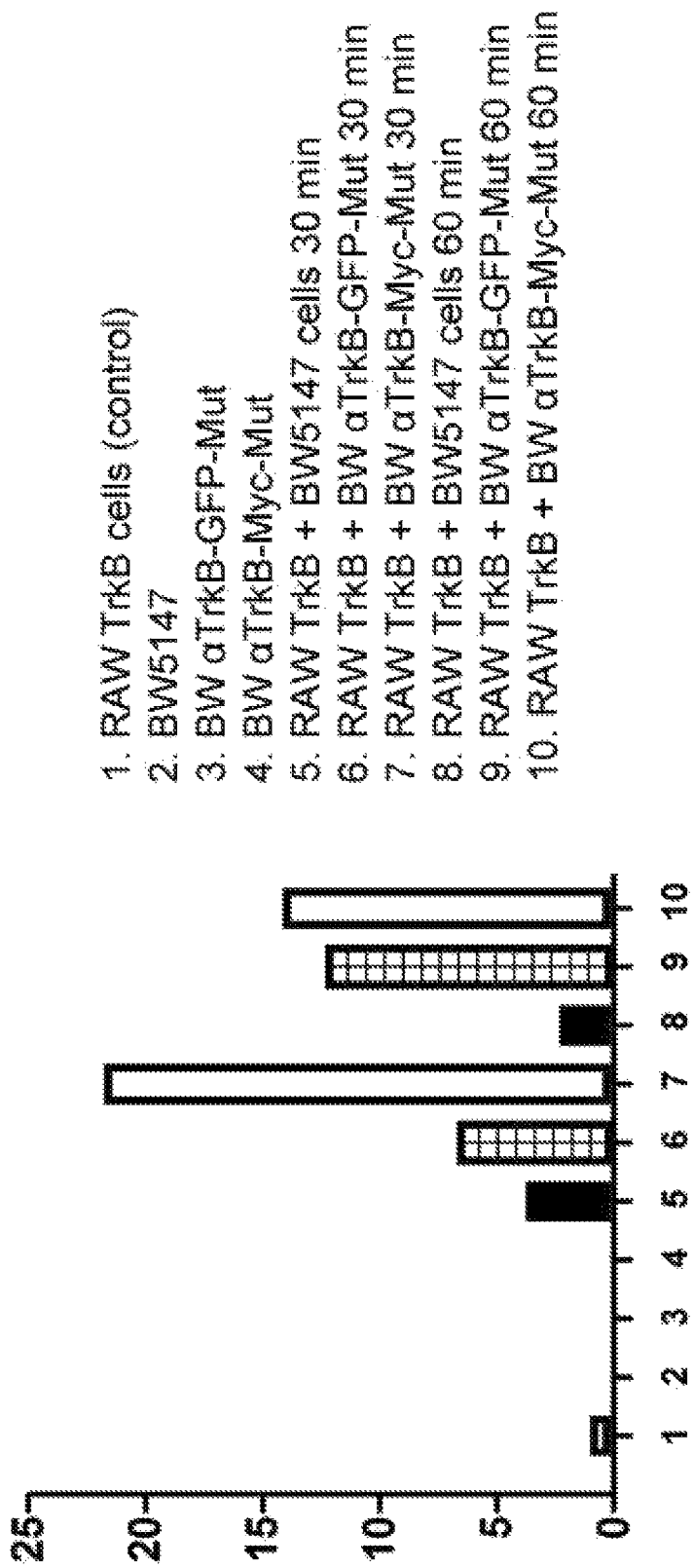
FIG. 1B is a bar graph summarizing the relative amounts of pTrkb presented in FIG. 1A. Acting and total TrkB are used to standardize the expression of the phosphorylated form.

Example 1. BW Cells Expressing αTrkB-Myc or αTrkB-GFP Chimeric Receptors Cells Induce the Phosphorylation of TrkB in Target RAW-TrkB Cells To test the ability of TRAMMICS expressing cells to induce phosphorylation of the tyrosine receptor kinase B (TrkB) receptor on target cells, the following experiment was performed. RAW 264.7 cells stably expressing TrkB were generated. These RAW-TrkB cells were incubated with untransformed BW5147, BW-αTrkB-GFP with mutant (Mut) zeta chain (SEQ ID NO: 20), and BW-αTrkB-Myc-Mut (SEQ ID NO: 18), for 30 and 60 min. The results of this experiment are presented in FIGS. 1A-B. The protein band at 145 kDa, corresponding to the phosphorylation of TrkB at tyrosine 706, can be seen in FIGS. 1A and 1s quantified in FIG. 1B. Coculture with BW-αTrkB-GFP-Mut (FIG. 1B, #6) and to a greater extent BW-αTrkB-Myc-Mut (FIG. 1B, #7) cells induced an increase in the level of phosphorylated TrkB (pTrkB) in RAW-TrkB cells as compared to coculture with unmodified BW5147 cells (FIG. 1B, #5) after 30 min of coculturing. Following 1 hour of coculturing, both BWαTrkB-GFP-Mut (FIG. 1B, #9) and BWαTrkB-Myc-Mut (FIG. 1B, #10) cells induced pTrkB in RAW-TrkB cells. The level of total TrkB receptor expression and the expression level of the actin loading control were used as references.

Example 2. Production of IL-2 by BW Cells Expressing the Chimeric Receptor Upon Binding to the TrkB Receptor of Target Cells Next, it was investigated whether BW cells expressing the chimeric receptor with a wild type or mutant ITAM regions, can be induced to secrete IL-2. Raw264.7 cells expressing TrkB receptor and WT Raw264.7 cells were seeded on 96 well plates in DMEM based media (10% FBS, PSN). After reaching 85-95% confluency, cells were twice washed and 100 ul of DMEM media with 0.2% FBS was added for 4 hours. After 4 hours, BW5147 cells were added to the wells in 100 ul of DMEM media without FBS for overnight incubation. Supernatants from co-cultured cells were collected after 16 hours and analyzed for IL-2 with a sandwich ELISA according to the manufacturer's instructions. Samples were analyzed in triplicates.

Figure 2:
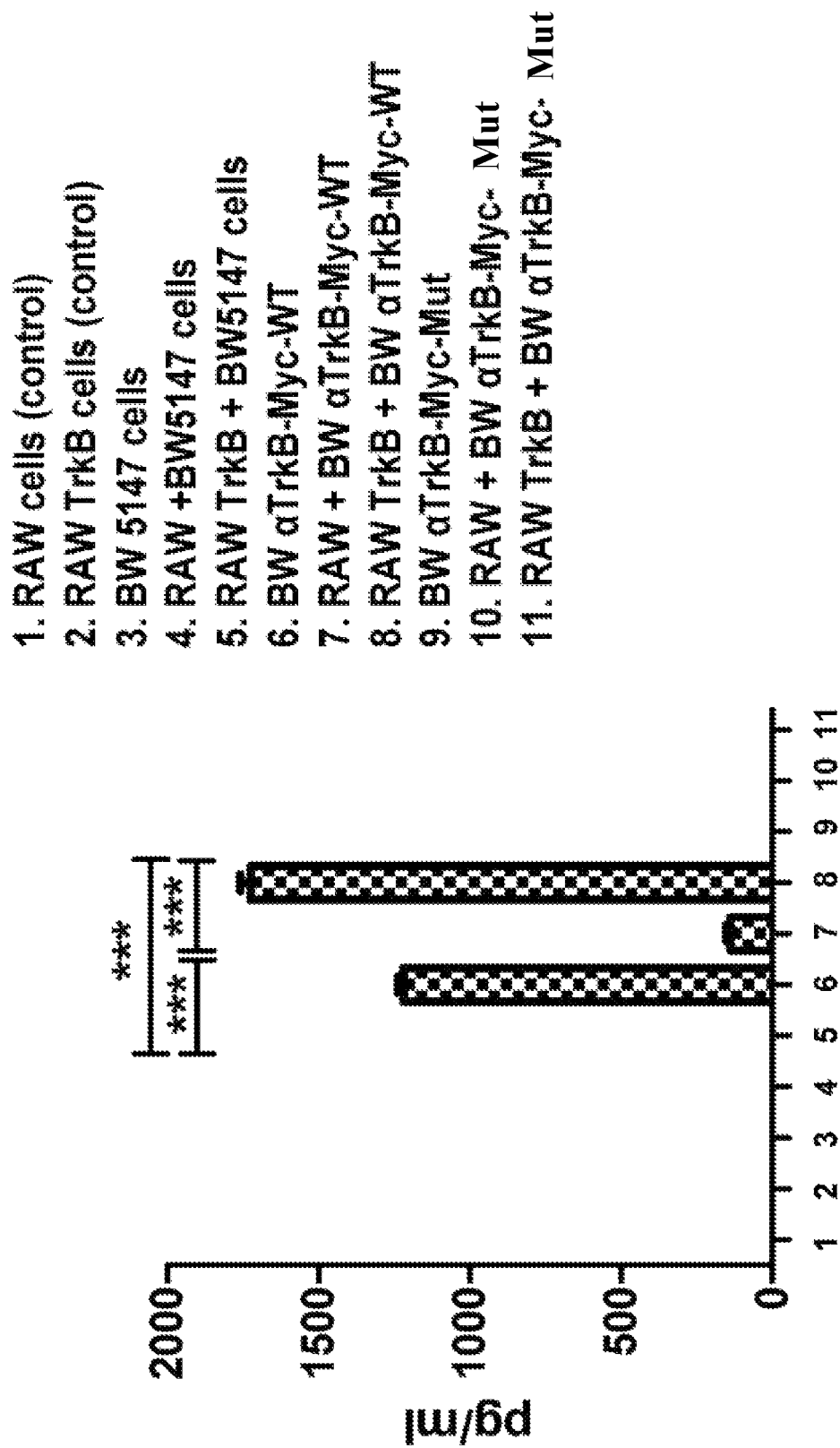
FIG. 2 is a bar graph showing the relative amount of IL-2 secreted from cultured cells. Results are shown as OD levels (650 wave length) from the IL-2 ELISA assay.
Figure 3A:
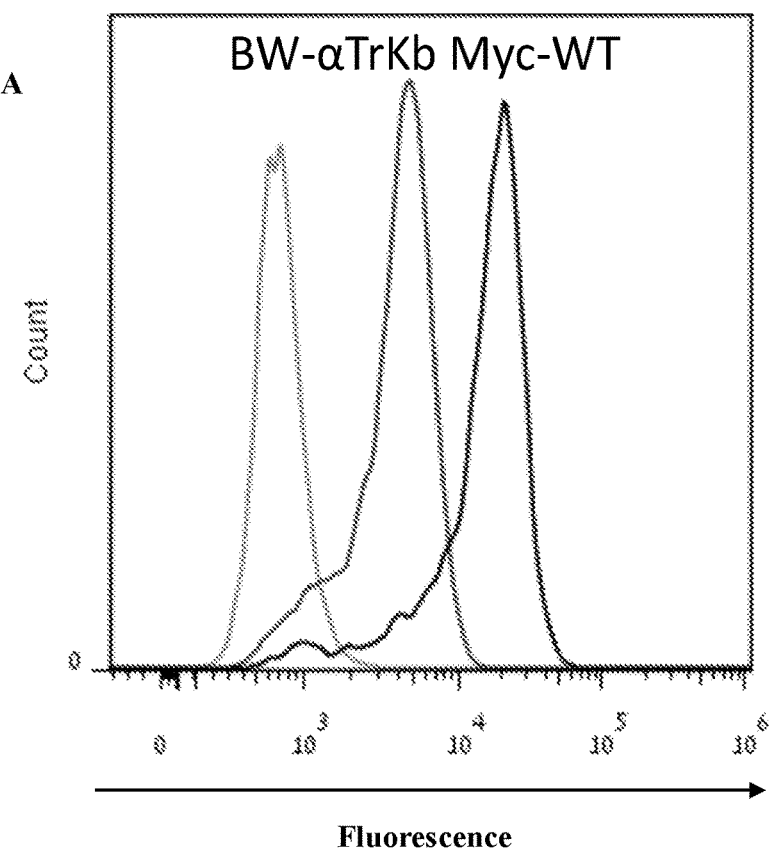
FIGS. 3A-3G are histograms of surface expression of Myc or GFP after viral transduction of (3A) αTrkB-Myc-WT, (3B) αTrkB-Myc-Mut, (3C) αTrkB-GFP-WT, (3D) αTrkB-GFP-Mut, (3E) αGLP1R-Myc-WT, and (3F) αGLP1R-Myc-Mut into BW cells and (3G) αGLP1R-Myc-Mut into primary murine T-helper cells. Light grey-unstained cells or non-transduced cells, grey—2nd antibody only control for Myc figures (anti-APC), black—Myc or GFP transduced cells.
Figure 3B:
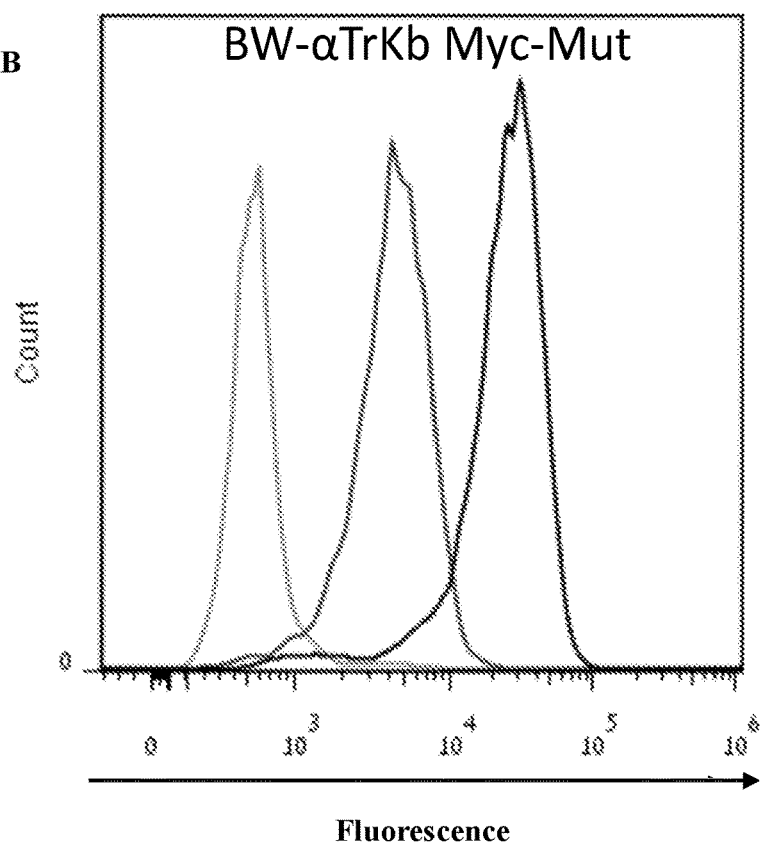
Figure 3C:
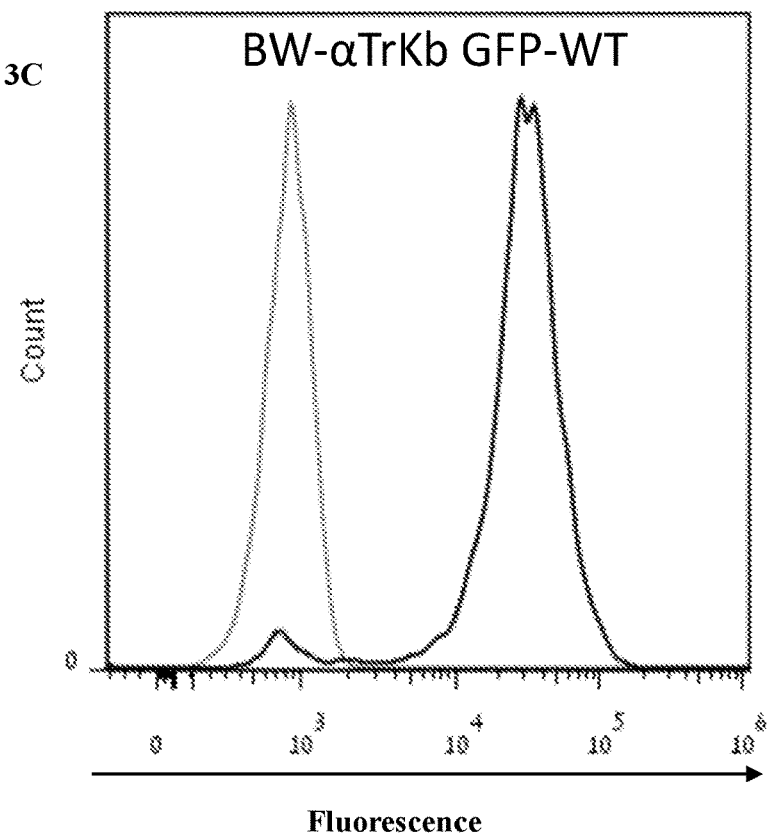
Figure 3D:
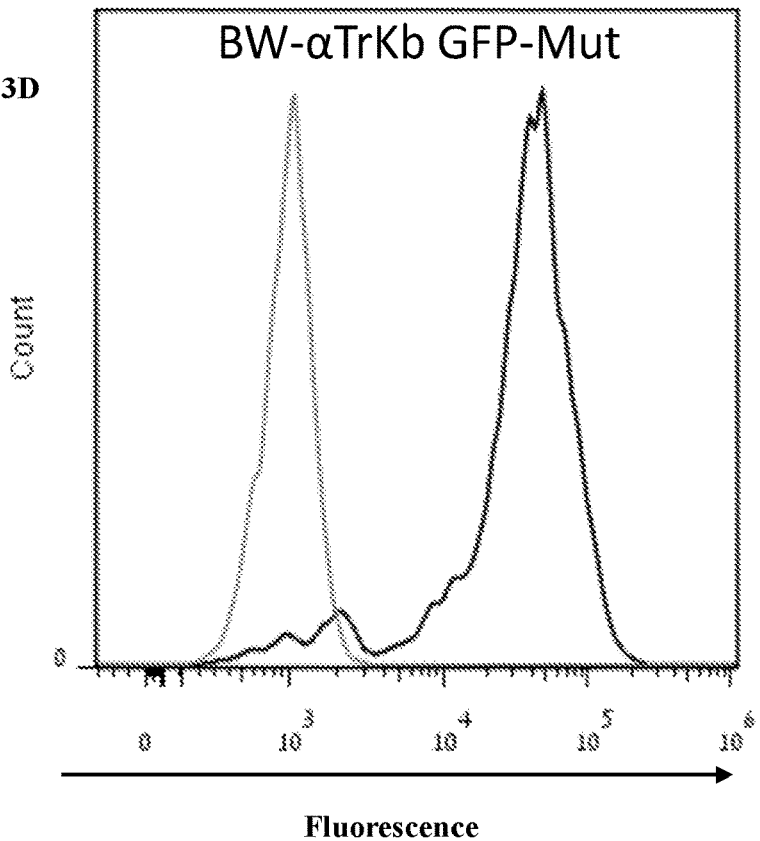
Figure 3E:
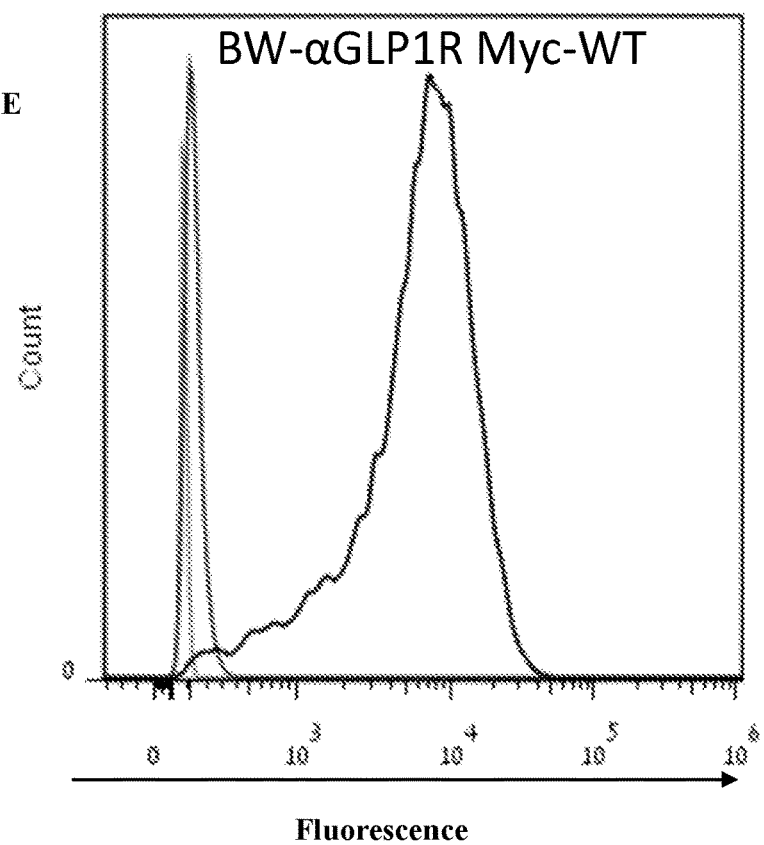
Figure 3F:
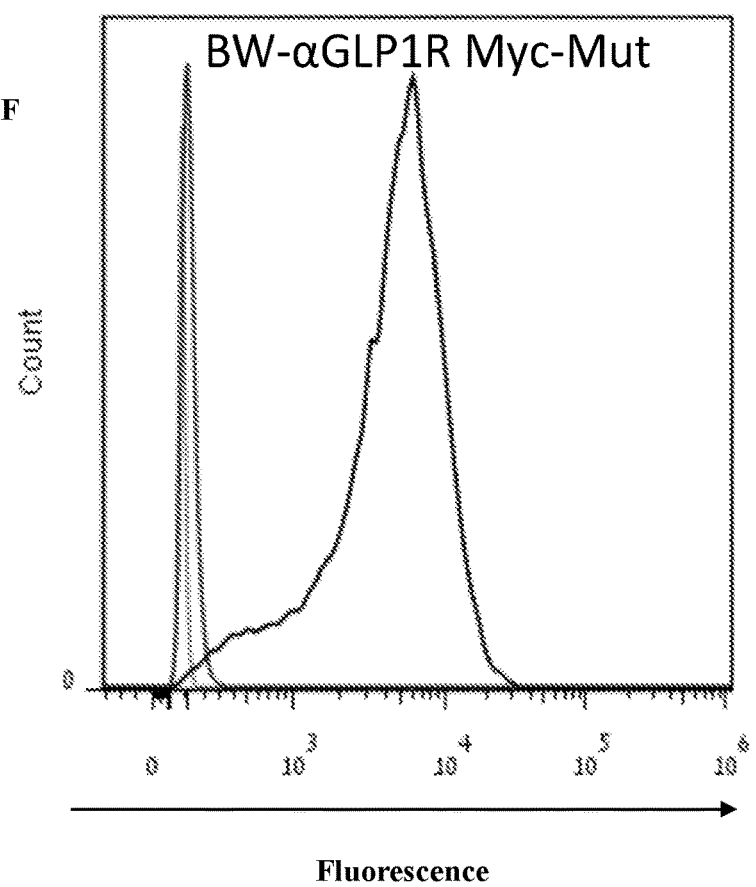
Figure 3G:
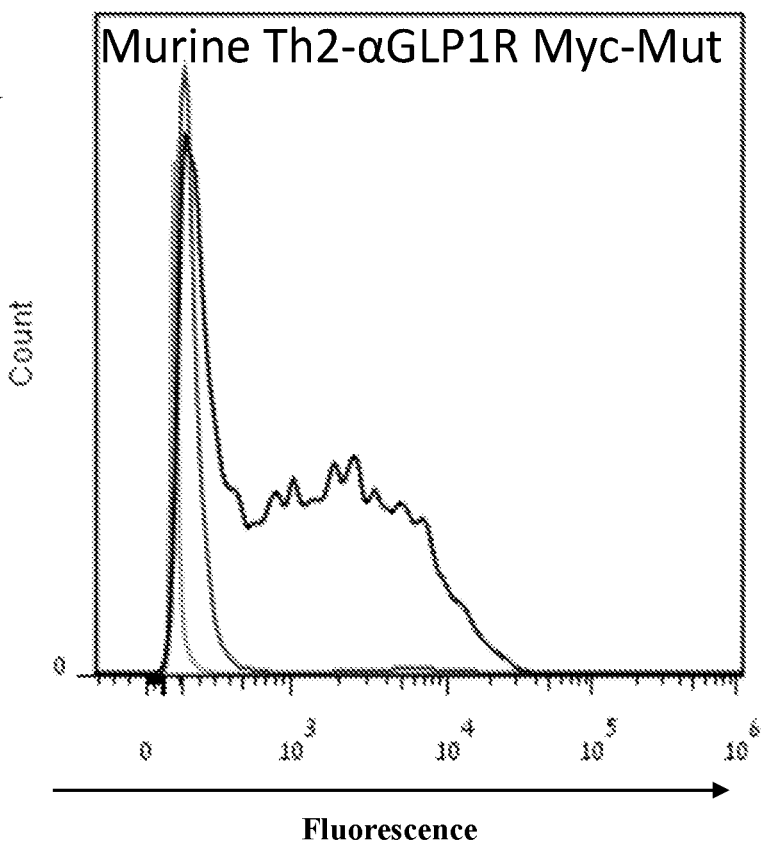

Only cells expressing BWαTrkB-Myc with wild type ITAM regions were able to produce IL-2 upon binding to RAW cells overexpressing TrkB receptor (FIG. 2, #8). Incubation with WT RAW cells, which endogenously express low amount of TrkB receptor, induced significantly lower level of IL-2 (FIG. 2, #7). No activation of BW cells was observed when the receptor contained mutated zeta chain, regardless of whether the incubation was with WT RAW cells (FIG. 2, #10) or RAW cells overexpressing TrkB receptor (FIG. 2, #11).

Example 3. Expression of Chimeric Receptor after Transfection into T Cells

In order to assess the membrane-associated expression of the chimeric receptors on T cells the murine T cell line BW5147.3 (ATCC® TIB-47) or primary murine T-helper cells were used. Cells were transduced with recombinant retroviral vectors encoding six different chimeric receptors. 48-72 hours following transduction, cells were sorted for receptor-positive-cells using either staining for Myc expression (when Myc Tag was part of the chimeric receptor) or for GFP expression (when GFP was part of the chimeric receptor) (FIG. 3A-G). Distinct high surface expression of the chimeric receptor was observed in all cases. Specifically, αTrkB-Myc-WT (FIG. 3A, SEQ ID NO: 17), αTrkB-Myc-Mut (FIG. 3B, SEQ ID NO: 18), αGLP1R-Myc-WT (FIG. 3E, SEQ ID NO: 21), αGLP1R-Myc-Mut (FIG. 3F, SEQ ID NO: 22), αTrkB-GFP-WT (FIG. 3C, SEQ ID NO: 19), and αTrkB-GFP-Mut (FIG. 3D, SEQ ID NO: 20), were highly expressed on the surface of BW cells. Further, αGLP1R-Myc-Mut (FIG. 3G, SEQ ID NO: 22) was also shown to be highly expressed on the surface of transduced murine T-helper cells.

Example 4. Activation of BW Cells Expressing the Chimeric Receptor with Plastic-Bound Anti-Myc Antibody In order to test whether plastic-bound anti-Myc antibody can activate T cells expressing the Myc containing chimeric proteins to secrete IL-2 the following experiment was performed. Six different Myc-containing constructs were expressed in BW cells: the four Myc containing constructs referenced in Example 3, as well as αGH-Myc-WT (SEQ ID NO: 23), αGH-Myc-Mut (SEQ ID NO: 24). The six resultant cell lines were incubated for 16-18 hours with titrated amounts (2500 to 4.8 ng/ml in the coating solution) of plastic-bound commercial anti-Myc Ab (50000 cells/96 plate well). Anti-CD16 (2500 ng/ml in coating sol.) was employed as negative control to anti-Myc. Following overnight incubation, mIL-2 levels in the supernatant were determined by commercial ELISA kit.

Figure 4:
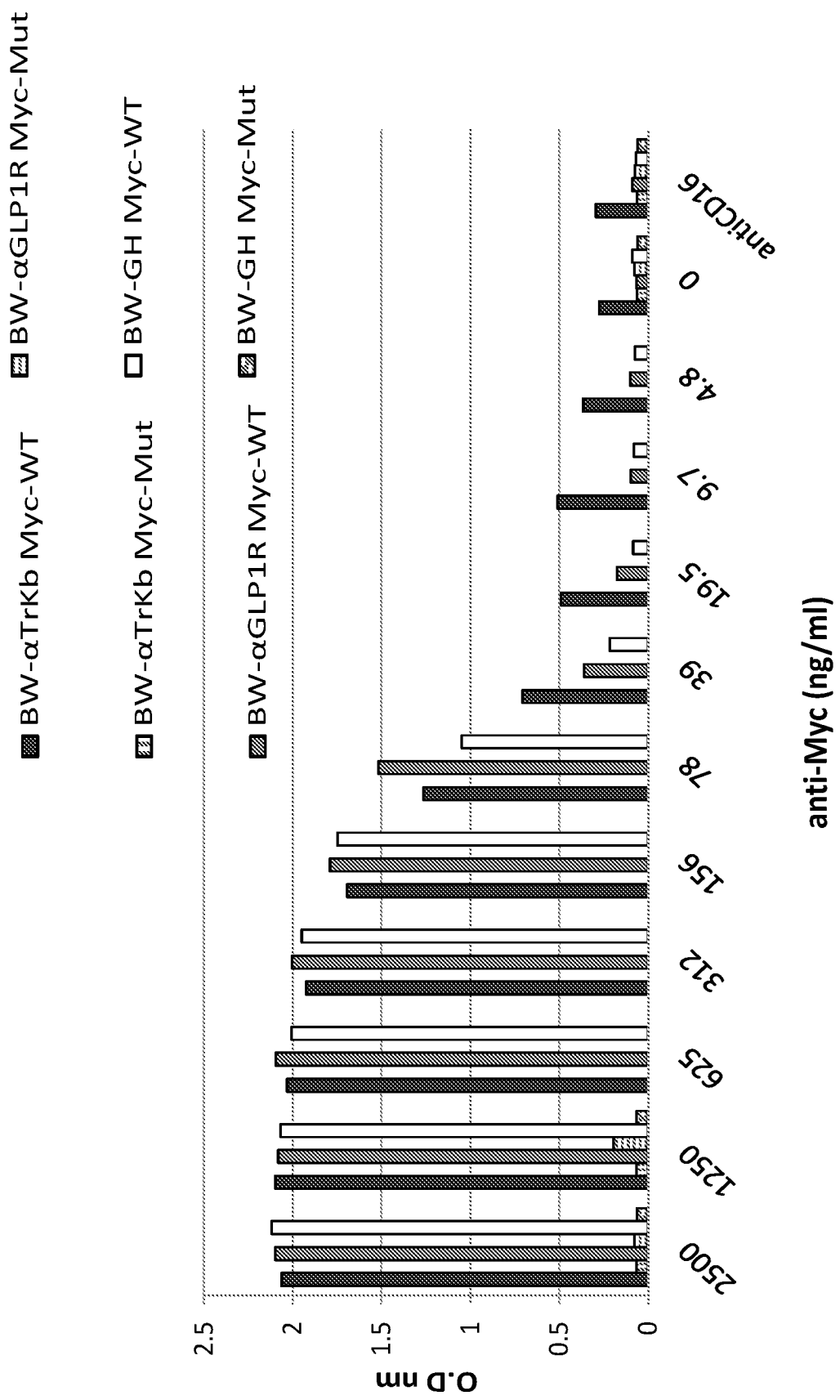
FIG. 4 is a bar graph showing the relative amount of IL-2 secreted from transduced cells expressing Myc-containing constructs after co-incubation with anti-Myc antibody. Results are shown as OD levels (650 wave length) from the IL-2 ELISA assay.

Clear activation (based on IL-2 secretion) was observed in all cells expressing constructs containing the WT zeta chain and further the intensity of 11-2 secretion was directly correlated with the amount of plastic-bound anti-Myc antibody employed (FIG. 4). No activation was observed when the expressed receptor contained a mutated zeta chain, even at the highest concentrations of the anti-Myc antibody used.

It was thus concluded that the chimeric receptors containing Myc-Tag and WT zeta chain combined with any one of the anti-TrkB $V_L$-linker-$V_H$ sequence, the anti GLP1R $V_L$-linker-$V_H$ sequence or the growth hormone (GH) sequence, are effectively activated by plastic-bound anti-Myc. This result shows that the chimeric receptor is functional and can be mobilized and aggregated on the membrane of the T cell to generate a functional synapse upon the presence of appropriate signal from the target side (mimicked here by plastic-bound anti-Myc antibody). Further, it is evident that the six tyrosine (Y) to phenylalanine (F) single amino acid mutations on the zeta chain are sufficient to prevent any activation by the T cell following interaction with the target.

Figure 5:
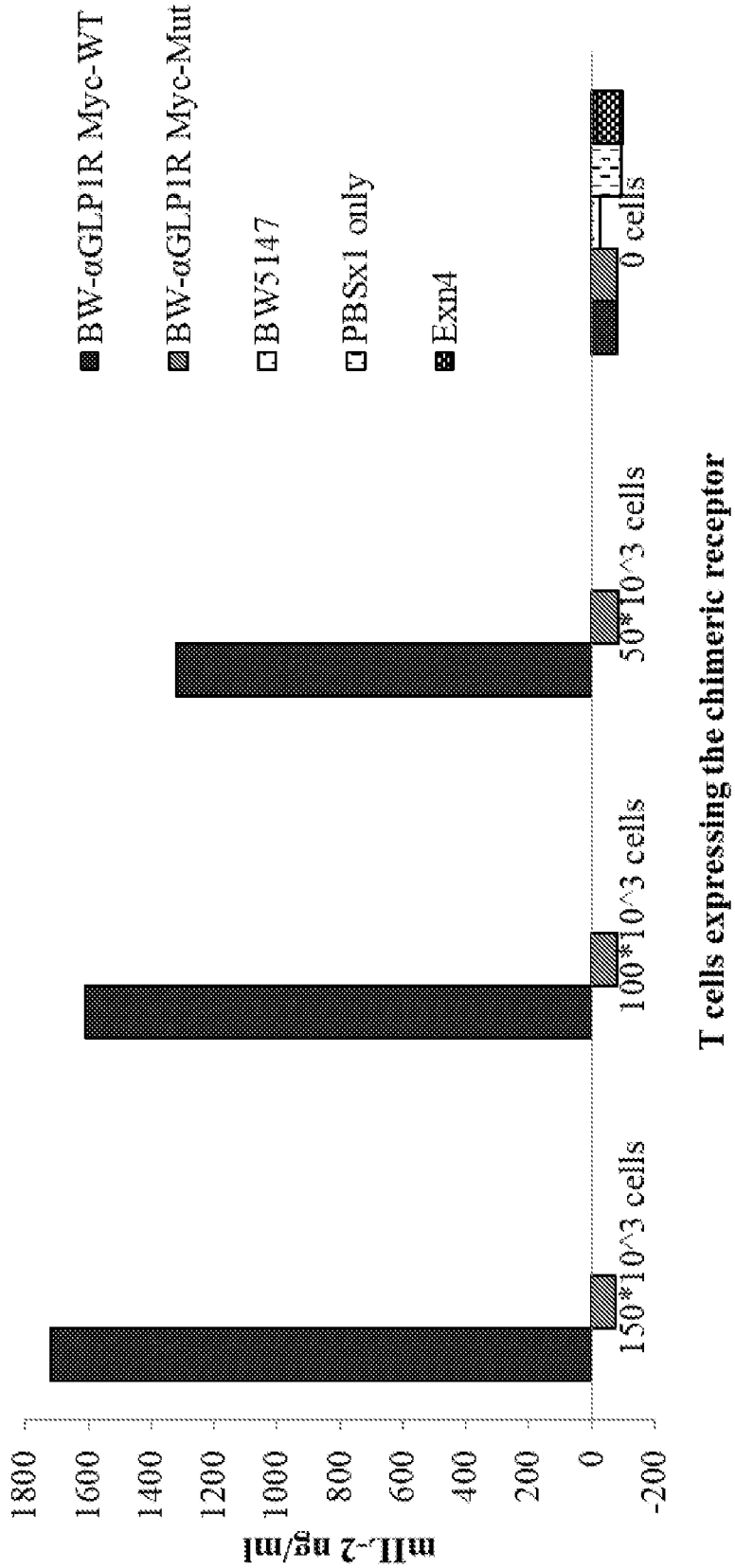
FIG. 5 is a bar graph showing the relative amount of IL-2 secreted from transduced cells expressing Myc-containing constructs after co-incubation with GLP1R expressing cells. Results are shown as OD levels (650 wave length) from the IL-2 ELISA assay.

Example 5. Activation of T Cells Expressing αGLP1R Chimeric Receptor with Target Cells Carrying GLP1R Next the ability of cells expressing GLP1R (CHO-GLP1R, Cat. No. MOO451, GenScript, Piscataway, NJ, USA), to activate T cells expressing the chimeric anti-GLP1R receptor to secrete IL-2 was examined. Shown in FIG. 5 are T cells expressing αGLP1R-Myc-WT or αGLP1R-Myc-Mut, T cells with no chimeric receptor (BW5147), and CHO-GLP1R with no T cells added (PBS). The GLP1R agonist Exendin 4 (Exn 4) was also added in place of T-cells as a control. First, commercial GLP1R-expressing CHO cells were pre-seeded and allowed to attach for 24 hours. Following incubation with T-cells or controls for 18 hours, supernatant was harvested, and murine IL-2 levels were determined by commercial ELISA kit.

Clear activation is observed (based on IL-2 secretion) only when the T cells were expressing αGLP1R-Myc-WT and this activation (IL-2 secretion) was directly correlated to the amount of T cells added (FIG. 4). No activation was measured for all other cases including the case in which T cells expressing the chimeric receptor αGLP1R-Myc-mut were added. These results corroborate the assertion that mutated zeta chain does not allow for activation of the T-cell regardless of the manner of engagement of the chimeric protein.

Figure 6:
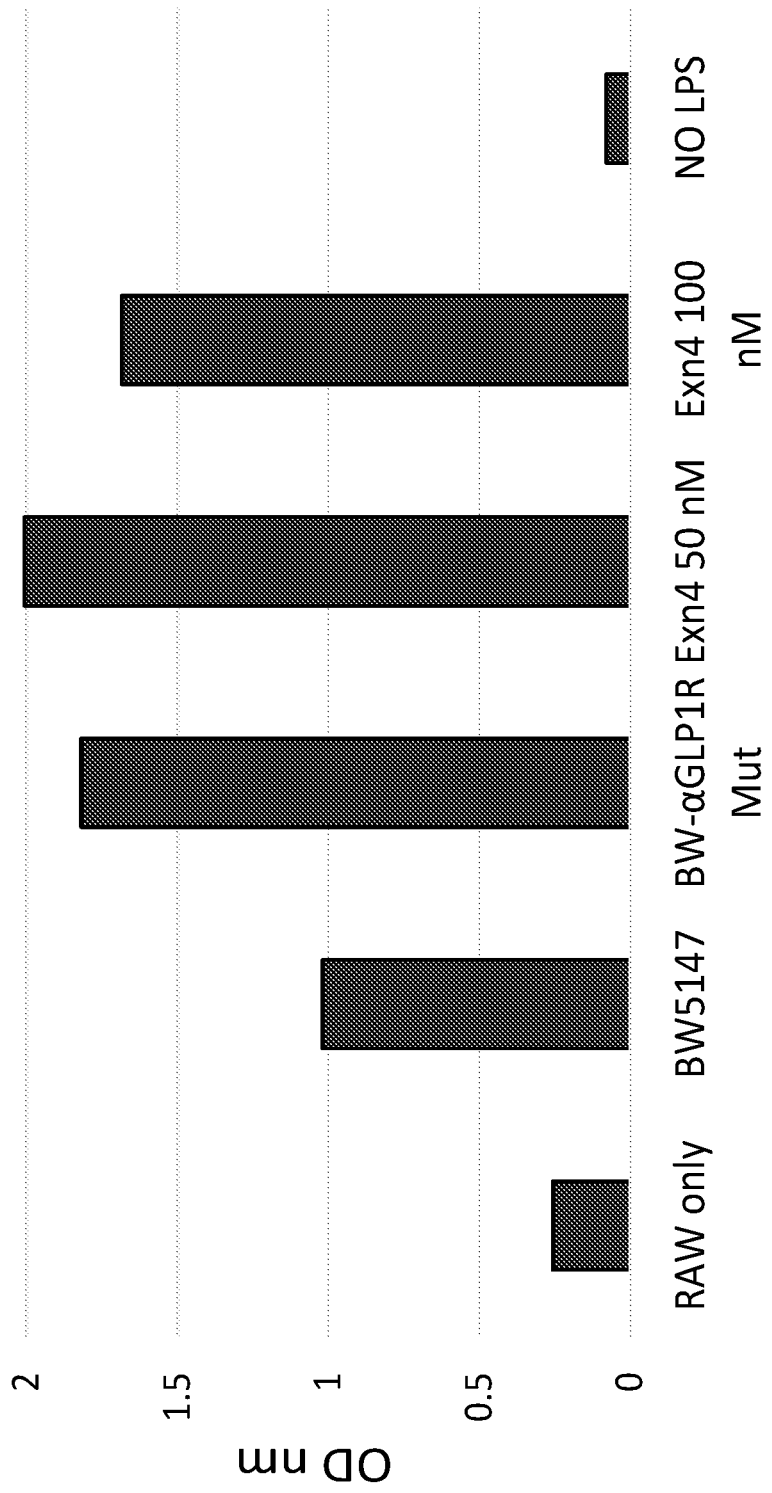
FIG. 6 is a bar graph showing the relative amount of TNF alpha secreted from Raw cells. Murine TNFα levels in the supernatant were determined by commercial ELISA kit. Results of ELISA assay are presented as OD-650.

Example 6. Expression of mTNFα from Target RAW Cells Incubated with Effector Cells Expressing the Appropriate Chimeric Receptor Knowing that BW cells expressing αGLP1R-Myc-Mut cannot be themselves activated, it was investigated whether these cells can activate cells expressing GLP1R to secret mTNFα. RAW264.7 cells (RAW 264.7 ATCC® TIB-71™) are a murine macrophage/monocyte cell line that naturally expresses the murine GLP1R. Activation of GLP1R is known to induce TNFα secretion by these RAW cells. Following co-incubation with WT BW cells, BW cells expressing the chimeric anti-GLP1R receptor, or the GLP1R agonist Exn4 supernatant from the Raw cells was harvested and murine TNFα levels in the supernatant were determined by commercial ELISA kit (FIG. 6).

Clear activation of target RAW cells was observed (based on mTNFα) only when T cells that are expressing the αGLP1R-Myc-Mut were co-incubated with the target RAW cells. Low activation level and no activation of RAW cells were observed when T cells were not added (Raw only (treated with low LPS concentration—1 ug/ml) and RAW with no LPS treatment (no-LPS) columns, respectively) Some activation was observed when T cells that do not express the receptor are added (BW5147), but it is significantly less as compared to addition of T cell expressing the anti-GLP1R receptor. A positive control in this experiment that proves the effectiveness of the setup, is the addition of GLP1R agonist Exendin4 (Exn4) which induces TNFα expression that is on par with the chimeric receptor.

Thus, it is concluded that T cells expressing chimeric anti-GLP1R receptor containing the mutant zeta chain are effective at activating target cells expressing the GLP1R receptor through the GLP1R receptor. This result proves that the chimeric receptor is functional, even with the zeta mutated, and is capable of inducing potent responses from target cells expressing the appropriate receptor.

Example 7. Blocking Negative Regulation of Immune Cells Using Anti PD-1 SCAAB

PD1-positive NK cells are incubated with immune cells expressing an anti-PD1 SCAAB (SEQ ID NO: 28). Next, PD-1L positive tumor cells are added and NK activation is measured. Alternatively, an antigen-mediated T-cell activation assay is used to assay NK cell activation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A pharmaceutical composition that does not kill cells not of the composition, consisting essentially of a modified cell wherein said cell is an immune cell selected from a CD4+ T-cell, a B-cell, and a dendritic cell, and wherein said cell comprises a chimeric antigen-recognizing receptor (CAR) wherein an intracellular domain of said CAR comprises a CD3 zeta chain in which all immunoreceptor tyrosine-based activation motif (ITAM) domains comprise a mutation of at least one tyrosine and said modified cell does not kill cells bound by said CAR; and a pharmaceutically acceptable carrier, excipient, or adjuvant, wherein said modified cell serves as a ligand that modulates signaling by a target receptor in a target cell.

2. The pharmaceutical composition of claim 1, wherein said composition comprises at least 1 million modified cells.

3. The pharmaceutical composition of claim 1, wherein said CAR further comprises an intracellular domain of a transmembrane protein selected from CD28, OX-40 CD80, CD86 and a T-cell receptor (TCR), wherein said intracellular domain of a transmembrane protein is devoid of an ITAM domain or comprises a mutation of at least one tyrosine in an ITAM domain.

4. The pharmaceutical composition of claim 1, wherein
  a. said intracellular domain comprises an intracellular domain of any transmembrane protein other than CD3, CD28, OX-40 CD80, CD86 and a T-cell receptor (TCR);
  b. said CAR comprises a CD3 transmembrane domain;
  c. said CAR comprises an extracellular hinge region, optionally wherein said hinge region comprises a CD-8 hinge region; or
  d. a combination thereof.

5. A method of modulating signaling by a target receptor in a target cell in a population of cells in which cells of said population of cells are not killed, the method comprising contacting said population of cells with a composition comprising a modified cell comprising a CAR wherein an intracellular domain of said CAR comprises a CD3 zeta chain in which all ITAM domains comprise a mutation of at least one tyrosine, and wherein the modified cell is an immune cell selected from a CD4+ T-cell, a B-cell, an antigen presenting cell and a dendritic cell and serves as a ligand and thereby modulates signaling by a target receptor in a target cell in a population without killing cells of said population bound by said CAR.

6. The method of claim 5, wherein said signaling by a target cell comprises a signaling cascade in said target cell.

7. The method of claim 5, wherein said modulating comprises inducing or inhibiting, and wherein at least one of:
  a. said inducing signaling comprises phosphorylation of a residue within a signaling domain of said target receptor;
  b. said inducing signaling comprises upregulation of a level of a downstream target of said target receptor; and
  c. said inhibiting signaling comprises down-regulation of a level of a downstream target of said target receptor.

8. The method of claim 5, wherein said CAR further comprises an intracellular domain of a transmembrane protein selected from CD28, OX-40 CD80, CD86 and a T-cell receptor (TCR), wherein said intracellular domain of a transmembrane protein is devoid of an ITAM domain or comprises a mutation of at least one tyrosine in an ITAM domain.

9. The method of claim 5, wherein said target receptor is at least one of:
  a. associated with a disease or disorder; and
  b. selected from GHR, GLP1R, TrkB, and PD-1.

10. The method of claim 5, wherein said modified cell is derived from a primary human cell from a human donor, and wherein said modified primary human cell is suitable for use in human therapy.

11. The method of claim 5, wherein said modulating treats a disease or disorder in a subject, said contacting comprises administering said cell expressing said CAR to said subject, and at least one of:
  a. said disease or disorder is selected from Alzheimer's disease, depression, and memory loss, said target receptor is TrkB and said CAR is an agonist of TrkB;
  b. said disease or disorder is selected from amyotrophic lateral sclerosis (ALS), epilepsy, brain cancer, said target receptor is TrkB and said CAR is an antagonist of TrkB;
  c. said disease or disorder is selected from, diabetes, obesity, glycogen storage disease, Parkinson's disease, mitochondrial myopathy, stroke, myocardial infarction, cardiac ischemia, and coronary artery disease, said target receptor is GLP1R and said CAR is an agonist of GLP1R;
  d. said disease or disorder is selected from growth hormone deficiency, Turner syndrome, and Prader-Willi syndrome, said target receptor is GHR and said CAR is an agonist of GHR;
  e. said disease or disorder is selected from acromegaly and GHR positive cancer, said target receptor is GHR and said CAR is an antagonist of GHR;
  f. said disease or disorder is selected from: rheumatoid arthritis, psoriasis, Graves' disease, immune-mediated inflammation, and celiac disease, said target receptor is PD-1 and said CAR is an agonist of PD-1; and
  g. said disease or disorder is selected from lupus and PD-L1 positive cancer, said target receptor is PD-1 and said CAR is an antagonist of PD-1.

12. The method of claim 11, wherein said provided cell is at least one of:
a. autologous to said subject;
b. allogenic to said subject;
c. derived from a primary human cell from a human donor, and wherein said modified primary human cell is suitable for use in human therapy; and
d. a primary cell extracted from said subject.

13. The method of claim 5, wherein
a. said intracellular domain comprises an intracellular domain of any transmembrane protein other than CD3, CD28, OX-40 CD80, CD86 and a T-cell receptor (TCR);
b. said CAR comprises a CD3 transmembrane domain;
c. said CAR comprises an extracellular hinge region, optionally wherein said hinge region comprises a CD-8 hinge region; or
d. a combination thereof.

14. The method of claim 5, wherein said composition consists of said modified cell and a pharmaceutically acceptable carrier, excipient, or adjuvant.

15. A method of producing an agent that modulates signaling by a target receptor in a target cell without killing said target cell, the method comprising:
a. providing a cell determined to not kill said target cell upon binding said target cell;
b. selecting at least one protein domain determined to bind to said target receptor;
c. generating a CAR comprising said selected at least one protein domain or a nucleic acid molecule encoding said CAR, wherein an intracellular domain of said CAR comprises a CD3 zeta chain comprising a mutation of at least one tyrosine in an ITAM domain;
d. expressing in a plasma membrane of said cell said generated CAR to produce a modified cell;
e. confirming binding of said modified cell to said target receptor on said target cell without killing said target cell upon binding; and
f. confirming modulation of signaling by said target receptor in said target cell;
thereby generating an agent that modulates signaling by a target receptor in a target cell without killing said target cell.

16. The method of claim 15, wherein step (b) comprises selecting at least one protein domain that upon binding modulates said target receptor and wherein said method further comprises confirming said agent modulates signaling by said target receptor.

17. The method of claim 15, wherein said cell determined not to kill said target cell upon binding said target cell is selected from a CD4+ T-cell, a B-cell, a myeloid cell, a macrophage, a monocyte, a neutrophil, an antigen presenting cell and a dendritic cell.

18. The method of claim 15, wherein said confirming binding without killing comprises measuring secretion of interleukin 2 (IL-2) or tumor necrosis factor alpha (TNFa) from said modified cell and confirming binding to said target receptor on said target cell does not increase secretion.

19. A pharmaceutical composition, consisting of a modified cell wherein said cell is selected from a mesenchymal stem cell, an embryonic stem cell, an induced pluripotent stem cell, a pluripotent stem cell and an immune cell selected from a CD4+ T-cell, a B-cell, an antigen presenting cell and a dendritic cell, and wherein said cell comprises a chimeric antigen-recognizing receptor (CAR) wherein an intracellular domain of said CAR comprises a CD3 zeta chain in which all immunoreceptor tyrosine-based activation motif (ITAM) domains comprise a mutation of at least one tyrosine and said modified cell does not kill cells bound by said CAR; and a pharmaceutically acceptable carrier, excipient, or adjuvant.

* * * * *